(12) United States Patent
Murata et al.

(10) Patent No.: US 8,329,913 B2
(45) Date of Patent: Dec. 11, 2012

(54) CARBAZOLE DERIVATIVE, SOLVATE THEREOF, OR PHARMACEUTICALLY ACCEPTABLE SALT THEREOF

(75) Inventors: Masakazu Murata, Tokyo (JP); Yoshihiko Itokazu, Tokyo (JP); Ryu Nakao, Tokyo (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 1132 days.

(21) Appl. No.: 11/666,631

(22) PCT Filed: Oct. 28, 2005

(86) PCT No.: PCT/JP2005/020250
§ 371 (c)(1),
(2), (4) Date: Sep. 10, 2007

(87) PCT Pub. No.: WO2006/046779
PCT Pub. Date: May 4, 2006

(65) Prior Publication Data
US 2010/0286210 A1     Nov. 11, 2010

(30) Foreign Application Priority Data
Oct. 29, 2004   (JP) ................................ 2004-316872

(51) Int. Cl.
*C07D 293/00* (2006.01)
(52) U.S. Cl. ........ 548/100; 514/339; 514/365; 514/374; 548/236; 548/181; 546/271.4
(58) Field of Classification Search .................. 514/358, 514/372, 384, 398, 401, 402, 339, 365, 374; 548/236, 184; 546/271.4
See application file for complete search history.

(56) References Cited

FOREIGN PATENT DOCUMENTS

| WO | WO-9603377 A1 | 2/1996 |
|---|---|---|
| WO | WO-98/18464 A1 | 5/1998 |
| WO | WO-01/26653 | 4/2001 |
| WO | WO-02/00255 | 1/2002 |
| WO | WO-02/00256 | 1/2002 |
| WO | WO-02/00257 | 1/2002 |
| WO | WO-02/074342 | 9/2002 |
| WO | WO-02/079154 A1 | 10/2002 |
| WO | WO-2004 024939 | 3/2004 |
| WO | WO-2004/048333 | 6/2004 |
| WO | WO-2004/048333 A1 | 6/2004 |

OTHER PUBLICATIONS

Martyn et al. ("Obesity-induced Insulin Resistance and Hyperglycemia: Etiologic Factors and Molecular Mechanisms"; 2008; Anesthesiology; Warner, et al., Eds.; 109:137-48.*
Uesugi et al "Comparative study on reduction of bone loss and lipid metabolism abnormality in ovarictomized Rats by soy isoflavones, daidzin, geinistin and glycitin", Biol. Pharm. Bull. vol. 24, No. 4, 2001, pp. 368-372.*
Kiyotaka "Reading of examination for lipid metabolism abornormality and cardiovascular risk", journal of the Japanese society of internal medicine, vol. 93, No. 4, pp. 683-689, 2004.*
Vippagunta et al. ("Crystalline solids"; 2001; Advanced Drug Delivery Reviews; 48: 3-26.*
Imoto et al "Studies on Non-Thiazolidinedione antidiabetic agents. 1. Discovery of novel oxyiminoacetic acid derivatives", Chem. Pharm. Bull vol. 50 No. 10, pp. 1349.*
King et al "Progress in Medicinal Chemistry", 2004, Book, ISBN:0-444-51143-1 (As per a phone conversation with Elsevier at 800-460-3110, the publication date is Apr. 15, 2004).*
Vippagunta et al. ("Crystalline solids"; 2001; Advanced Drug Delivery Reviews; 48: 3-26).*
International Preliminary Report on Patentability mailed May 10, 2007, in International Application No. PCT/JP2005/020250 (6 pages).

(Continued)

*Primary Examiner* — Brandon Fetterolf
*Assistant Examiner* — Jean Cornet
(74) *Attorney, Agent, or Firm* — Osha Liang LLP

(57) ABSTRACT

An object of the present invention is to provide novel carbazole derivatives, solvates thereof, or pharmaceutically acceptable salts thereof having an excellent adipose tissue weight reducing effect, hypoglycemic effect, and hypolipidemic effect, which are useful as a preventive and/or therapeutic agent for fatty liver, obesity, lipid metabolism abnormality, visceral adiposity, diabetes, hyperlipemia, impaired glucose tolerance, hypertension, non-alcoholic fatty liver disease, non-alcoholic steatohepatitis, and the like.

The above-mentioned object can be achieved by carbazole derivatives, solvates thereof, or pharmaceutically acceptable salts thereof, wherein the carbazole derivatives are represented by the following general formula (I):

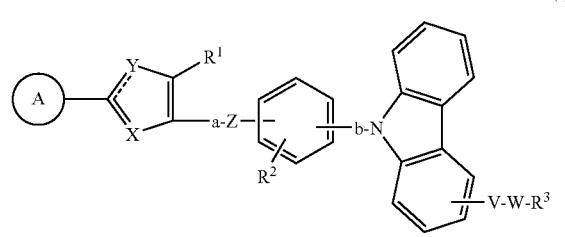

(I)

(In the formula (I), the ring A represents phenyl group or the like; X represents —O— or the like; Y represents =N— or the like; a and b represent methylene group or the like; both V and Z represent —O— or the like; W represents a $C_1$-$C_{10}$ alkylene group whose 1 or 2 hydrogen atoms may be substituted by a phenyl group or a $C_1$-$C_6$ alkyl group; 1,2-phenylene group; 1,3-cyclohexyl group; or the like; $R^1$ represents methyl group or the like; $R^2$ represents methoxy group or the like; and $R^3$ represents carboxy group or the like.).

23 Claims, No Drawings

OTHER PUBLICATIONS

Lehmann, Jurgen M., et al.; Communication "An Antidiabetic Thiazolidinedione Is a High Affinity Ligand for Peroxisome Proliferator-activated Receptor γ (PPARγ)"; The Journal of Biological Chemistry, vol. 270, No. 22, Issue of Jun. 2, 1995; by The American Society for Biochemistry and Molecular Biology, Inc. (USA); pp. 12953-12956 (4 pages).

Forman, Barry M., et al.; "15-Deoxy-$\Delta^{12, 14}$-Prostaglandin $J^2$ Is a Ligand for the Adipocyte Determination Factor PPARγ"; Cell, vol. 83; Dec. 1, 1995, by Cell Press; pp. 803-812 (10 pages).

Kliewer, Steven A., et al.; "A Prostaglandin $J^2$ Metabolite Binds Peroxisome Proliferator-Activated Receptor γ and Promotes Adipocyte Differentiation"; vol. 83, Dec. 1, 1995, by Cell Press; pp. 813-819 (7 pages).

Kubota, Naoto, et al.; "PPARγ Mediates High-Fat Diet-Induced Adipocyte Hypertrophy and Insulin Resistance"; Molecular Cell, vol. 4; Oct. 1999, by Cell Press; pp. 597-609 (13 pages).

De Vos, Piet, et al.; "Thiazolidinediones Repress *ob* Gene Expression in Rodents Via Activation of Peroxisome Proliferator-activated Receptor γ"; J. Clin. Invest., vol. 98, No. 4, Aug. 1996; The American Society for Clinical Investigation, Inc.; pp. 1004-1009 (6 pages).

Zhang, Bei, et al.; "Down-regulation of the Expression of the Obese Gene by an Antidiabetic Thiazolidinedione in Zucker Diabetic Fatty Rats and *db/db* Mice"; The Journal of Biological Chemistry, vol. 271, No. 16, Issue of Apr. 19, 1996, by The American Society for Biochemistry and Molecular Biology, Inc.; pp. 9455-9459 (USA) (5 pages).

International Search Report for PCT/JP2005/020250 mailed Dec. 20, 2005 with translation (4 pages).

Henke, Brad R., "Peroxisome Proliferator-Activated Receptor a/y Dual Agonists for the Treatment of Type 2 Diabetes"J. Med. Chem., 2004, vol. 47, No. 17, pp. 4118-4127 (10 pages).

United States Patent Application Publication No. US2004/0142921 A1, published Jul. 22, 2004; Inventor(s): Lu et al. Cited for Reference BA above (WO2004/048333), which is not available.

* cited by examiner

CARBAZOLE DERIVATIVE, SOLVATE THEREOF, OR PHARMACEUTICALLY ACCEPTABLE SALT THEREOF

TECHNICAL FIELD

The present invention relates to carbazole derivatives, solvates thereof, or pharmaceutically acceptable salts thereof, as well as medical compositions and medicines containing such compounds. To be more specific, the present invention relates to novel carbazole derivatives, solvates thereof, pharmaceutically acceptable salts thereof, and the like having an excellent adipose tissue weight reducing effect, hypoglycemic effect, and hypolipidemic effect, which are useful as a preventive and/or therapeutic agent for fatty liver, obesity, lipid metabolism abnormality, visceral adiposity, diabetes, hyperlipemia, impaired glucose tolerance, hypertension, non-alcoholic fatty liver disease, non-alcoholic steatohepatitis, and the like.

BACKGROUND ART

In recent years, lifestyle-related diseases such as obesity and diabetes are brought in question. Accordingly, transcription factors related to expression inductions of adipocyte differentiation marker genes are gaining attention. A peroxisome proliferator-activated receptor (hereinafter, also referred to as "PPAR") is known to be related to a lot of physiological and/or pathological phenomena such as fat metabolism, regulation of inflammation, cell differentiation, and functional regulation, thereby gaining special attention.

The PPAR is a nuclear receptor belonging to a steroid/retinoid receptor superfamily of ligand responsive transcription factors (Curr. Opin. Chem. Biol., (1997), 1, 235-241; Cell, (1995), 83, 841-850). cDNAs of PPAR are cloned from various animal species and several isoform genes of PPAR are found. Among mammals, three subtypes, PPARα, PPARγ, and PPARδ, are known (J. Steroid Biochem. Molec. Biol., (1994), 51, 157; Gene Expression, (1995), 4, 281; Biochem. Biophys. Res. Commun., (1996), 224, 431; Mol. Endocrinol., (1992), 6, 1634).

The PPARγ is known to be expressed mainly in the adipose tissue, immune organ, adrenal gland, spleen, small intestine, skeletal muscle, and liver. On the other hand, the PPARα is known to be expressed mainly in the liver, heart, kidney, adrenal gland, skeletal muscle, and retina. Also, the PPARδ is known to be universally expressed without tissue specificity. Each of the PPARs forms a stable heterodimer with a retinoid X receptor (RXR), and bind with a specific DNA recognition sequence (PPRE) of the target gene for control.

The PPARγ is induced at a very early phase of an adipocyte differentiation and plays an important role in the adipocyte differentiation as a key regulating (controlling) factor. The first chemical identified as a direct ligand of PPAR was BRL49653, the thiazolidinediones (TZDs) having an antidiabetic effect on type II diabetes. Also, pioglitazone and ciglitazone that are antidiabetic drugs for type II diabetes and are TZD-type (Lehmann, J. M., J. (1995) Biol. Chem. 270, 12953-12956 (non-patent document 1), as well as 15-deoxy-Δ12,14-prostaglandin J2 that is a kind of prostaglandin metabolite (Cell, (1995), 83, 803-812; Cell, (1995), 83, 813-819 (non-patent document 2)) are known as candidates for intrinsic ligands of PPARγ. Moreover, thiazolidinedione derivative that is an insulin sensitizer has been proved to increase the transcription activity of the PPARγ, and known to have an insulin resistance improving effect, hypoglycemic effect, and antihyperlipidemic effect.

Also, since adipocyte hypertrophy, fat accumulation and expression of insulin resistance are suppressed in a PPARγ hetero deficient mouse, a model that the PPARγ mediates adipocyte hypertrophy, fat accumulation and insulin resistance has been proposed (Mol. Cell, (1999), 4, 597 (non-patent document 3)). On the other hand, a thiazolidinedione (TZD) derivative that is a PPARγ agonist is reported to have adipocyte differentiation inductive effect and to increase the number of adipose cells and the weight of adipose tissues (J. Clin. Invest., (1996), 98, 1004-1009 (non-patent document 4)). Therefore, while the TZD derivative is useful as a curative medicine for diabetes, possibility of promoting obesity is a concern. Also, while leptin is known as an antiobesity factor, the expression level of leptin is reported to decrease when the TZD derivative is administered (J. Biol. Chem., (1996), 271, 9455-9459 (non-patent document 5)). Based on these backgrounds, the PPARγ antagonist is expected to control the differentiation of the adipose cell while simultaneously increasing the expression level of leptin, thereby acting as an antiobesity agent.

Compounds that are PPARγ receptor binder having the PPARγ antagonist effect are disclosed by WO01/30343, WO02/060388, WO03/000685, WO2004/024705, and the like. These compounds are supposed to have an antiobesity effect, an adipose tissue weight reducing effect, a hypoglycemic effect, a hypolipidemic effect, and the like.

On the other hand, WO01/26653, WO02/00255, WO02/00256, WO02/00257, and WO02/074342 (patent documents 1-5) disclose the following compound as a carbazole derivative. In these documents, the following compound is disclosed as a phospholipase A2 (sPLA2) inhibitor.

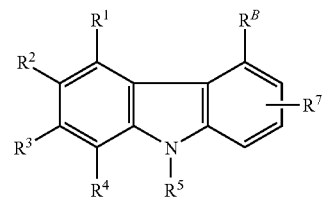

WO02/079154 (patent document 6) discloses the following compound as a sPLA2 inhibitor.

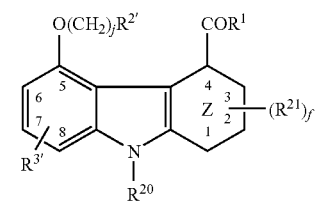

WO98/18464 (patent document 7) discloses the following compound as a sPLA2 inhibitor.

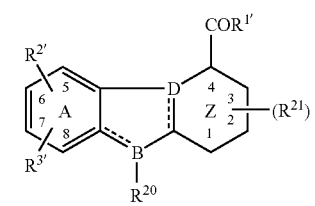

WO96/03377 (patent document 8) discloses the following compound as a muscarine receptor allosteric effector.

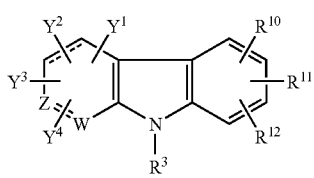

WO2004/048333 (patent document 9) discloses the following compound as a PPARγ agonist.

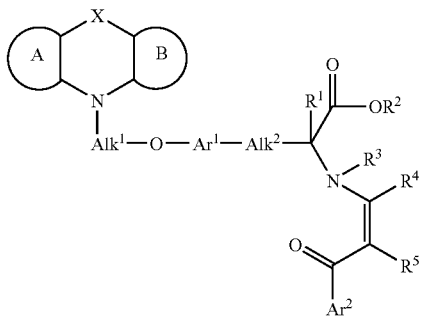

REFERENCES

Patent document 1: WO01/26653
Patent document 2: WO02/00255
Patent document 3: WO02/00256
Patent document 4: WO02/00257
Patent document 5: WO02/074342
Patent document 6: WO02/079154
Patent document 7: WO98/18464
Patent document 8: WO96/03377
Patent document 9: WO2004/048333
Non-patent document 1:
Lehmann, J. M., J. (1995) Biol. Chem. 270, 12953-12956
Non-patent document 2: Cell, (1995), 83, 803-812; Cell, (1995), 83, 813-819
Non-patent document 3: Mol. Cell, (1999), 4, 597
Non-patent document 4: J. Clin. Invest., (1996), 98, 1004-1009
Non-patent document 5: J. Biol. Chem., (1996), 271, 9455-9459

DISCLOSURE OF THE INVENTION

An object of the present invention is to provide novel carbazole derivatives, solvate thereof, or pharmaceutically acceptable salt thereof having an excellent fatty tissue weight reducing effect, hypoglycemic effect, and blood lipid reducing effect, which are useful as a preventive and/or therapeutic agent for fatty liver, obesity, lipid metabolism abnormality, visceral adiposity, diabetes, hyperlipemia, impaired glucose tolerance, hypertension, non-alcoholic fatty liver disease (NAFLD), non-alcoholic steatohepatitis (NASH), and the like.

Another object of the present invention is to provide novel carbazole derivative, solvate thereof, or pharmaceutically acceptable salt thereof that is a PPAR modulator. Another of the present invention is to provide a novel carbazole derivative, solvate thereof, or pharmaceutically acceptable salt thereof showing a PPARγ inhibitory effect or partial inhibitory effect (or partial agonistic effect). Another object of the present invention is to provide a novel carbazole derivative, solvate thereof, or pharmaceutically acceptable salt thereof showing a PPARγ inhibitory effect or partial inhibitory effect (or partial agonistic effect) and showing a PPARα agonistic effect.

Still another object of the present invention is to provide a preventive and/or therapeutic agent for metabolic syndrome and the like including a novel carbazole derivative, solvate thereof, or pharmaceutically acceptable salt thereof as an active ingredient.

Yet another object of the present invention is to provide a medical composition or medicine including the above mentioned novel compounds.

Further, yet another object of the present invention is to provide a novel intermediate compound useful for the preparation of the above-mentioned novel compounds.

In consideration of the above-mentioned circumstances, the present inventors have carried out careful studies and have consequently synthesized for the first time carbazole derivatives and salts thereof having the following structure. Moreover, the present inventors have found that these compounds control the PPAR and have preventive and/or therapeutic effect for disorders related to the PPAR, and have completed the present invention.

[1] Namely, the present invention relates to a carbazole derivative, solvate thereof, or pharmaceutically acceptable salt thereof represented by the following general formula (I):

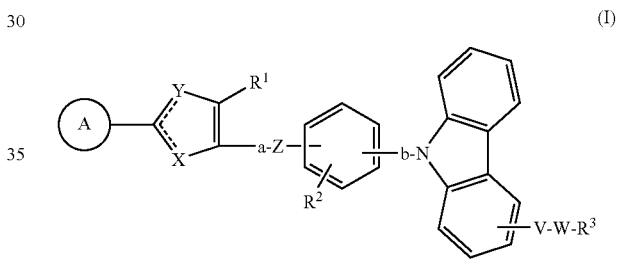

In the formula (I),
a ring A represents a $C_6$-$C_{10}$ aryl group which may have 1 to 3 substituent groups selected from a group A of substituent groups, or a 5- to 7-membered aromatic heterocyclic group which may have 1 to 3 substituent groups selected from the group A of substituent groups;
X represents =N—, =CH—, —O—, or —S—;
Y represents =N—, —O—, or —S—;
a and b may be same or different, and represent a $C_1$-$C_4$ alkylene group which may have a substituent group selected from the group A of substituent groups, a $C_2$-$C_4$ alkenylene group which may have a substituent group selected from the group A of substituent groups, or a $C_2$-$C_4$ alkynylene group which may have a substituent group selected from the group A of substituent groups;
V and Z may be same or different, and represent a methylene group, =N—, —NH—, —O—, —S—, —S(=O)—, —S(=O)$_2$—, —C(=O)—, —C(=O)NH—, or —NHC(=O)—;
W represents a $C_1$-$C_{10}$ alkylene group which may have a substituent group selected from the group A of substituent groups, a $C_2$-$C_{10}$ alkenylene group which may have a substituent group selected from the group A of substituent groups, a $C_2$-$C_{10}$ alkynylene group which may have a substituent group selected from the group A of substituent groups, a $C_3$-$C_7$ cycloaliphatic hydrocarbon group which may have 1 to 3 substituent groups selected from the group A of substituent groups, or a $C_6$-$C_{10}$ arylene group which may have 1 to 3 substituent groups selected from the group A of substituent groups;

$R^1$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, or a $C_1$-$C_4$ alkoxy group which may have a substituent group selected from the group A of substituent groups;

$R^2$ represents, a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups;

$R^3$ represents a hydrogen atom, a hydroxy group, a cyano group, —C(=O)$R^4$ ($R^4$ represents a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups), or —C(=O)$NR^5R^6$ ($R^5$ and $R^6$ may be same or different, and represent a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, a $C_1$-$C_4$ alkylsulfonyl group which may have a substituent group selected from the group A of substituent groups, or a $C_6$-$C_{12}$ arylsulfonyl group which may have a substituent group selected from the group A of substituent groups), the group A of substituent groups represents a group including:
halogen;
a hydroxy group;
a carboxy group;
a cyano group;
a $C_1$-$C_6$ alkyl group whose 1 to 3 hydrogen atoms may be substituted by halogen, a hydroxy group, a carboxy group, or a carbamoyl group;
a $C_2$-$C_6$ alkenyl group whose 1 to 3 hydrogen atoms may be substituted by halogen, a hydroxy group, a carboxy group, or a carbamoyl group;
a $C_2$-$C_6$ alkynyl group whose 1 to 3 hydrogen atoms may be substituted by halogen, a hydroxy group, a carboxy group, or a carbamoyl group;
a $C_1$-$C_6$ alkoxy group whose 1 to 3 hydrogen atoms may be substituted by halogen, a hydroxy group, a carboxy group, or a carbamoyl group;
a $C_1$-$C_6$ alkylthio group whose 1 to 3 hydrogen atoms may be substituted by halogen, a hydroxy group, a carboxy group, or a carbamoyl group;
a $C_3$-$C_7$ cycloaliphatic hydrocarbon group whose 1 to 3 hydrogen atoms may be substituted by halogen, a hydroxy group, a carboxy group, or a carbamoyl group;
a $C_7$-$C_{16}$ aralkyl group whose 1 to 3 hydrogen atoms may be substituted by halogen, a hydroxy group, a carboxy group, or a carbamoyl group;

a carbamoyl group which may be monosubstituted or disubstituted by a substituent group selected from a $C_1$-$C_4$ alkoxycarbonyl group, a $C_1$-$C_4$ alkyl group, a $C_1$-$C_4$ alkylsulfonyl group, and a $C_6$-$C_{10}$ arylsulfonyl group;

a $C_6$-$C_{10}$ aryl group whose 1 to 3 hydrogen atoms may be substituted by halogen, a hydroxy group, a carboxy group, or a carbamoyl group; and a 5- to 7-membered aromatic heterocyclic group whose 1 to 3 hydrogen atoms may be substituted by halogen, a hydroxy group, a carboxy group, or a carbamoyl group.

The above-mentioned novel compounds have a preferred PPARγ inhibitory activity, PPARγ partial inhibitory activity, or PPARα agonistic activity as confirmed by the examples that will be described later. Therefore, the above-mentioned novel compounds are useful for treatment and prevention of the PPAR involved disorders.

[2] A preferable carbazole derivative, solvate thereof, or pharmaceutically acceptable salt thereof among those represented by the general formula (I) is the carbazole derivative, solvate thereof, or pharmaceutically acceptable salt thereof represented by the following general formula (I'):

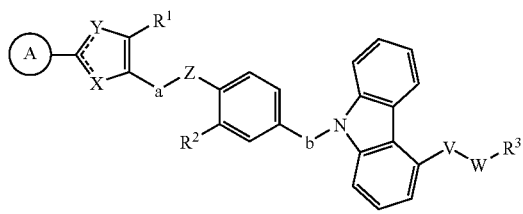

(I')

[3] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents {a phenyl group, an indenyl group, a 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups;

X represents =N—, —O—, or —S—;
Y represents =N—, —O—, or —S—;
a and b may be same or different, and represent a $C_1$-$C_4$ alkylene group whose 1 or 2 hydrogens are substituted by {halogen, a $C_1$-$C_4$ alkyl group, or a $C_1$-$C_4$ alkoxy group};

V and Z may be same or different, and represent a methylene group, —NH—, —O—, —S—, or —S(=O)—;

W represents a $C_1$-$C_{10}$ alkylene group which may have a substituent group selected from a group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by a substituent group selected from a group C of substituent groups, a $C_1$-$C_4$ alkoxy group whose 1 to 3 hydrogens may be substituted by a substituent group selected from the group C of substituent groups, or a $C_1$-$C_4$ alkylthio group whose 1 to 3 hydrogens may be substituted by a substituent group selected from the group C of substituent groups, where the group C of substituent groups represents a group including halogen, a $C_1$-$C_4$ alkyl group, a $C_1$-$C_4$ alkoxy group, and a $C_1$-$C_4$ haloalkyl group; and $R^3$ represents a hydrogen atom, a hydroxy group, a cyano group, or —C(=O)$R^4$ ($R^4$ represents a hydrogen atom, a hydroxy group, a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}.).

[4] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents {a phenyl group, an indenyl group, a 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups;

X represents =N—, —O—, or —S—;
Y represents =N—, —O—, or —S—;
a and b may be same or different, and represent a $C_1$-$C_4$ alkylene group whose 1 or 2 hydrogens may be substituted by {halogen, a $C_1$-$C_4$ alkyl group, or a $C_1$-$C_4$ alkoxy group};
V and Z may be same or different, and represent a methylene group, —NH—, —O—, —S—, or —S(=O)—;
W represents a $C_1$-$C_{10}$ alkylene group which may have a substituent group selected from the group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by {a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {a $C_1$-$C_4$ alkyl group, a $C_1$-$C_4$ alkoxy group, or a $C_1$-$C_4$ haloalkyl group}, or a $C_1$-$C_4$ alkylthio group whose 1 to 3 hydrogens may be substituted by {a $C_1$-$C_4$ alkyl group, a $C_1$-$C_4$ alkoxy group, or a $C_1$-$C_4$ haloalkyl group}; and $R^3$ represents a hydrogen atom, a hydroxy group, a cyano group, —C(=O)$R^4$ ($R^4$ represents a hydrogen atom, hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}.), or —C(=O)$NR^5R^6$ ($R^5$ and $R^6$ may be same or different, and represent a hydrogen atom, a hydroxy group, a $C_1$-$C_4$ alkyl group, a $C_1$-$C_4$ alkoxy group, a $C_1$-$C_4$ alkylsulfonyl group, or a $C_6$-$C_{12}$ arylsulfonyl group.).

[5] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X represents =N—, —O—, or —S—;
Y represents =N—, —O—, or —S—;
a and b may be same or different, and represent a $C_1$-$C_4$ alkylene group;
V and Z may be same or different, and represent a methylene group, —NH—, —O—, —S—, or —S(=O)—;
W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group};

$R^1$ represents a $C_1$-$C_4$ alkyl group, or a $C_1$-$C_4$ alkoxy group;

$R^2$ represents a hydrogen atom, a $C_1$-$C_4$ alkoxy group, or a $C_1$-$C_4$ alkylthio group; and $R^3$ represents a hydroxy group, or —C(=O)$R^4$ ($R^4$ represents a hydrogen atom, a hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}.).

[6] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X and Y represent any one of: (i) X representing —O— and Y representing =N—, (ii) X representing =N— and Y representing —O— or —S—, and (iii) X representing —S— and Y representing =N—;

a and b may be same or different, and represent a $C_1$-$C_4$ alkylene group;

V and Z may be same or different, and represent —NH—, —O—, —S—, or —S(=O)—;

W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group};

$R^1$ represents a $C_1$-$C_4$ alkyl group, or a $C_1$-$C_4$ alkoxy group;

$R^2$ represents, a hydrogen atom, a $C_1$-$C_4$ alkoxy group, or a $C_1$-$C_4$ alkylthio group; and $R^3$ represents —C(=O)$R^4$ ($R^4$ represents a hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}.).

[7] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents a phenyl group, a 2-furyl group, a 2-thienyl group, or a 4-pyridyl group;

X and Y represent any one of: (i) X representing —O— and Y representing =N—, (ii) X representing =N— and Y representing —O— or —S—, and (iii) X representing —S— and Y representing =N—;

both a and b represent a methylene group;

both V and Z represent —O—;

W represents a $C_1$-$C_{10}$ alkylene group whose 1 or 2 hydrogens may be substituted by a phenyl group or a $C_1$-$C_6$ alkyl group; a 1,2-phenylene group; or a 1,3-cyclohexyl group;

$R^1$ represents a methyl group;

$R^2$ represents a methoxy group; and $R^3$ represents a carboxy group.

[8] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents a phenyl group;

X represents —O—;

Y represents =N—;

both a and b represent a methylene group;

both V and Z represent —O—;

W represents a $C_1$-$C_4$ alkylene group whose 1 or 2 hydrogens may be substituted by a $C_1$-$C_4$ alkyl group;

$R^1$ represents a methyl group;

$R^2$ represents a methoxy group; and $R^3$ represents a carboxy group.

[9] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents a phenyl group;

X represents —O—;

Y represents =N—;

both a and b represent a methylene group;

both V and Z represent —O—;

W represents a methylene group, a methylmethylene group, a dimethylmethylene group, an ethylmethylene group, an isopropylmethylene group, an ethylene group, a methylethylene group, or an isopropylethylene group;

$R^1$ represents a methyl group;

$R^2$ represents a methoxy group; and $R^3$ represents a carboxy group.

[10] A more preferable carbazole derivative, solvate thereof, or pharmaceutically acceptable salt thereof among those represented by the general formula (I) or general formula (I') is the carbazole derivative, solvate thereof, or pharmaceutically acceptable salt thereof as described in the above-mentioned [1] or [2], wherein:

the ring A represents a phenyl group;

X represents =N—;

Y represents —O—;

a and b may be same or different, and represent a methylene group or an ethylene group;

both V and Z represent —O—;

W represents a $C_1$-$C_4$ alkylene group whose 1 or 2 hydrogens may be substituted by a $C_1$-$C_4$ alkyl group;

$R^1$ represents a methyl group;

$R^2$ represents a methoxy group; and $R^3$ represents a carboxy group.

[11] A more preferable carbazole derivative, solvate thereof, or pharmaceutically acceptable salt thereof among those represented by the general formula (I) is the carbazole derivative, solvate thereof, or pharmaceutically acceptable salt thereof as described in the above-mentioned [1], wherein the carbazole derivative represented by the formula (I) is one of:

{9-[3-methoxy-4-((5-methyl-2-phenyl-oxazole-4-yl)methoxy)-benzyl]-9H-carbazole-4-yloxy}acetic acid, {9-[4-((2-(furan-2-yl)-5-methyl-oxazole-4-yl)methoxy)-3-methoxy-benzyl]-9H-carbazole-4-yloxy}acetic acid, 2-{9-[3-methoxy-4-((5-methyl-2-phenyl-oxazole-4-yl)methoxy)-benzyl]-9H-carbazole-4-yloxy}-2-methyl-propionic acid, (±)-2-{9-[3-methoxy-4-((5-methyl-2-phenyl-oxazole-4-yl)methoxy)-benzyl]-9H-carbazole-4-yloxy}propionic acid, (±)-2-{9-[3-methoxy-4-((5-methyl-2-phenyl-oxazole-4-yl)methoxy)-benzyl]-9H-carbazole-4-yloxy}butyric acid, (±)-2-{9-[4-((2-(furan-2-yl)-5-methyl-oxazole-4-yl)methoxy)-3-methoxy-benzyl]-9H-carbazole-4-yloxy}-2-phenylacetic acid, 2-{9-[4-((2-furan-2-yl-5-methyl-oxazole-4-yl)methoxy)-3-methoxy-benzyl]-9H-carbazole-4-yloxy}2-methyl-propionic acid, 2-{9-[3-methoxy-4-((5-methyl-2-thiophene-2-yl-oxazole-4-yl)methoxy)-benzyl]-9H-carbazole-4-yloxy}-2-methyl-propionic acid, 2-{9-[3-methoxy-4-((5-methyl-2-pyridine-4-yl-oxazole-4-yl)methoxy)-benzyl]-9H-carbazole-4-yloxy}-2-methyl-propionic acid, (±)-2-{9-[3-methoxy-4-((5-methyl-2-phenyl-oxazole-4-yl)methoxy)-benzyl]-9H-carbazole-4-yloxy}-3-methyl-butyric acid, (±)-2-{9-[3-methoxy-4-((5-methyl-2-phenyl-oxazole-4-yl)methoxy)-benzyl]-9H-carbazole-4-yloxy}valeric acid, 4-{9-[3-methoxy-4-((5-methyl-2-phenyl-oxazole-4-yl)methoxy)-benzyl]-9H-carbazole-4-yloxy}butyric acid, 2-methyl-2-{9-[4-((5-methyl-2-phenyl-oxazole-4-yl)methoxy)-benzyl]-9H-carbazole-4-yloxy}propionic acid, 2-{9-[3-((2-(furan-2-yl)-5-methyl-oxazole-4-yl)methoxy)-4-methoxy-benzyl]-9H-carbazole-4-yloxy}-2-methyl-propionic acid, 2-{9-[3-methoxy-4-((5-methyl-2-phenyl-thiazole-4-yl)methoxy)-benzyl]-9H-carbazole-4-yloxy}-2-methyl-propionic acid, 2-{9-[3-methoxy-4-((4-methyl-2-phenyl-thiazole-5-yl)methoxy)-benzyl]-9H-carbazole-4-yloxy}-2-methyl-propionic acid, (±)-2-{9-[3-methoxy-4-((5-methyl-2-phenyl-oxazole-4-yl)methoxy)-benzyl]-9H-carbazole-4-yloxy}caproic acid, (±)-2-{9-[3-methoxy-4-((5-methyl-2-phenyl-oxazole-4-yl)methoxy)-benzyl]-9H-carbazole-4-yloxy}heptane acid, (±)-2-{9-[3-methoxy-4-((5-methyl-2-phenyl-oxazole-4-yl)methoxy)-benzyl]-9H-carbazole-4-yloxy}caprylic acid, 5-{9-[3-methoxy-4-((5-methyl-2-phenyl-oxazole-4-yl)methoxy)-benzyl]-9H-carbazole-4-yloxy}valeric acid, 6-{9-[3-methoxy-4-((5-methyl-2-phenyl-oxazole-4-yl)methoxy)-benzyl]-9H-carbazole-4-yloxy}caproic acid, 3-{9-[3-methoxy-4-((5-methyl-2-phenyl-oxazole-4-yl)methoxy)-benzyl]-9H-carbazole-4-yloxy}-2,2-dimethyl-propionic acid, 3-{9-[4-((2-(furan-2-yl)-5-methyl-oxazole-4-yl)methoxy)-3-methoxy-benzyl]-9H-carbazole-4-yloxy}-2,2-dimethyl-propionic acid, 3-{9-[3-methoxy-4-((5-methyl-2-(thiophene-2-yl)-oxazole-4-yl)methoxy)-benzyl]-9H-carbazole-4-yloxy}-2,2-dimethyl-propionic acid, 3-{9-[3-methoxy-4-((5-methyl-2-pyridine-4-yl-oxazole-4-yl)methoxy)-benzyl]-9H-carbazole-4-yloxy}-2,2-dimethyl-propionic acid, (±)-{9-[3-methoxy-4-((5-methyl-2-phenyl-oxazole-4-yl)methoxy)-benzyl]-9H-carbazole-4-yloxy}phenylacetic acid, (±)-4-{9-[3-methoxy-4-((5-methyl-2-phenyl-oxazole-4-yl)methoxy)-benzyl]-9H-carbazole-4-yloxy}-2-methyl-butyric acid, (S)-(+)-2-{9-[3-methoxy-4-((5-methyl-2-phenyl-oxazole-4-yl)methoxy)-benzyl]-9H-carbazole-4-yloxy}butyric acid, (S)-2-{9-[3-methoxy-4-((5-methyl-2-phenyl-oxazole-4-yl)methoxy)-benzyl]-9H-carbazole-4-yloxy}propionic acid, (S)-2-{9-[3-methoxy-4-((5-methyl-2-phenyl-oxazole-4-yl)methoxy)-benzyl]-9H-carbazole-4-yloxy}-3-methyl-butyric acid, (S)-2-{9-[3-methoxy-4-((5-methyl-2-phenyl-oxazole-4-yl)methoxy)-benzyl]-9H-carbazole-4-yloxy}valeric acid, (R)-2-{9-[3-methoxy-4-((5-methyl-2-phenyl-oxazole-4-yl)methoxy)-benzyl]-9H-carbazole-4-yloxy}butyric acid, (R)-2-{9-[3-methoxy-4-((5-methyl-2-phenyl-oxazole-4-yl)methoxy)-benzyl]-9H-carbazole-4-yloxy}propionic acid, (R)-2-{9-[3-methoxy-4-((5-methyl-2-phenyl-oxazole-4-yl)methoxy)-benzyl]-9H-carbazole-4-yloxy}-3-methyl-butyric acid, (R)-2-{9-[3-methoxy-4-((5-methyl-2-phenyl-oxazole-4-yl)methoxy)-benzyl]-9H-carbazole-4-yloxy}valeric acid, 4-((9-(4-((5-methyl-2-phenyloxazole-4-yl)methoxy)-3-methoxybenzyl)-9H-carbazole-5-yloxy)methyl)benzoic acid, 2-{9-[3-methoxy-4-((5-methyl-2-phenyloxazole-4-yl)methoxy)-benzyl]-9H-carbazole-4-yloxy}benzoic acid, 3-{9-[3-methoxy-4-((5-methyl-2-phenyloxazole-4-yl)methoxy)-benzyl]-9H-carbazole-4-yloxy}benzoic acid, 4-{9-[3-methoxy-4-((5-methyl-2-phenyloxazole-4-yl)methoxy)-benzyl]-9H-carbazole-4-yloxy}benzoic acid, (+)-2-{9-[3-methoxy-4-((5-methyl-2-phenyl-oxazole-4-yl)methoxy)-benzyl]-9H-carbazole-4-yloxy}-2-phenylacetic acid, (−)-2-{9-[3-methoxy-4-((5-methyl-2-phenyl-oxazole-4-yl)methoxy)-benzyl]-9H-carbazole-4-yloxy}-2-phenylacetic acid, (−)-4-{9-[3-methoxy-4-((5-methyl-2-phenyl-oxazole-4-yl)methoxy)-benzyl]-9H-carbazole-4-yloxy}-2-methyl-butyric acid, and (+)-4-{9-[3-methoxy-4-(5-methyl-2-phenyl-oxazole-4-yl-methoxy)-benzyl]-9H-carbazole-4-yloxy}-2-methyl-butyric acid.

[12] Another aspect of the present invention is a medical composition including the carbazole derivative, solvate thereof, or pharmaceutically acceptable salt thereof according to any one of the above-mentioned [1] to [11], and a pharmaceutically acceptable carrier. This medical composition is useful mainly as a medical composition involved in the function of the PPAR. This medical composition is used as a PPARγ antagonist and the like, and is useful for treatment or prevention of PPAR involved disorders.

[13] Another aspect of the present invention is a preventive agent and/or therapeutic agent for metabolic syndrome including the carbazole derivative, solvate thereof, or pharmaceutically acceptable salt thereof according to any one of the above-mentioned [1] to [11] as an active ingredient. In the present specification, the "preventive agent and/or therapeutic agent" denotes not only the preventive agent or the therapeutic agent but also an agent functioning as the preventive agent and the therapeutic agent. Prevention means to prevent or delay the symptoms from appearing. In the present invention, treatment means to relieve or cure the symptoms.

[14] Another aspect of the present invention is a preventive agent and/or therapeutic agent for fatty liver, obesity, lipid metabolism abnormality, visceral adiposity, diabetes, hyperlipemia, impaired glucose tolerance, hypertension, non-alcoholic fatty liver disease, or non-alcoholic steatohepatitis, the agent including the carbazole derivative, solvate thereof, or pharmaceutically acceptable salt thereof according to any one of the above-mentioned [1] to [11] as an active ingredient.

[15] Another aspect of the present invention is a preventive agent and/or therapeutic agent for fatty liver or obesity including the carbazole derivative, solvate thereof, or pharmaceutically acceptable salt thereof according to any one of the above-mentioned [1] to [11] as an active ingredient.

[16] Another aspect of the present invention is a PPAR modulator including the carbazole derivative, solvate thereof, or pharmaceutically acceptable salt thereof according to any one of the above-mentioned [1] to [11] as an active ingredient.

[17] Another aspect of the present invention is a PPARγ antagonist including the carbazole derivative, solvate thereof, or pharmaceutically acceptable salt thereof according to any one of the above-mentioned [1] to [11] as an active ingredient.

[18] Another aspect of the present invention is a usage of the carbazole derivative, solvate thereof, or pharmaceutically acceptable salt thereof according to any one of the above-mentioned [1] to [11] for the preparation of a preventive agent and/or therapeutic agent for fatty liver, obesity, lipid metabolism abnormality, visceral adiposity, diabetes, hyperlipemia, impaired glucose tolerance, hypertension, non-alcoholic fatty liver disease, or non-alcoholic steatohepatitis.

[19] Another aspect of the present invention is a carbazole derivative, solvate thereof, or pharmaceutically acceptable salt thereof, the carbazole derivative represented by the following general formula (I"): This aspect is related to an intermediate carbazole derivative represented by the general formula (I) or the general formula (I'). One whose T is —OH in the general formula (I") is an intermediate represented by a formula (VI) which will be described later, and can be effectively used when specifically producing a carbazole derivative represented by the general formula (I) or the general formula (I') according to a method B which will be described later. One whose T is —OP (P is a protecting group) in the general formula (I") is an intermediate represented by a formula (V) which will be described later, and can be effectively used when specifically producing a carbazole derivative represented by the general formula (I) or the general formula (I') according to the method B which will be described later. One whose T is —V—W—P' in the general formula (I") is an intermediate represented by a formula (VIII) which will be described later, and can be effectively used when specifically producing a carbazole derivative represented by the general formula (I) or the general formula (I') according to a method C which will be described later.

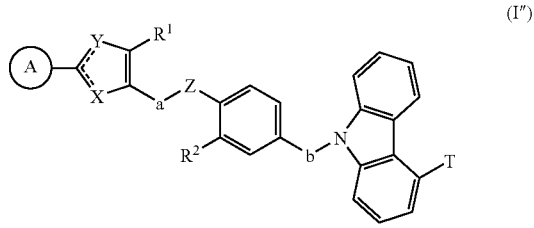

(I")

In the formula (I"), a ring A represents a $C_6$-$C_{10}$ aryl group which may have 1 to 3 substituent groups selected from the group A of substituent groups, or a 5- to 7-membered aromatic heterocyclic group which may have 1 to 3 substituent groups selected from the group A of substituent groups;

X represents =N—, =CH—, —O—, or —S—;

Y represents =N—, —O—, or —S—;

a and b may be same or different, and represent a $C_1$-$C_4$ alkylene group which may have a substituent group selected from the group A of substituent groups, a $C_2$-$C_4$ alkenylene group which may have a substituent group selected from the group A of substituent groups, or a $C_2$-$C_4$ alkynylene group which may have a substituent group selected from the group A of substituent groups;

Z represents a methylene group, =N—, —NH—, —O—, —S—, —S(=O)—, —S(=O)$_2$—, —C(=O)—, —C(=O) NH—, or —NHC(=O)—;

$R^1$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, or a $C_1$-$C_4$ alkoxy group which may have a substituent group selected from the group A of substituent groups;

$R^2$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups;

T represents —OH, —OP, or —V—W—P';

P represents a $C_1$-$C_4$ alkyl group which may have a substituent group selected from the group A of substituent groups, a $C_1$-$C_4$ aliphatic acyl group which may have a substituent group selected from the group A of substituent groups, or a $C_7$-$C_{11}$ aromatic acyl group which may have a substituent group selected from the group A of substituent groups;

V represents a methylene group, =N—, —NH—, —O—, —S—, —S(=O)—, —C(=O)—, —C(=O)NH—, or —NHC(=O)—;

W represents a $C_1$-$C_{10}$ alkylene group which may have a substituent group selected from the group A of substituent groups, a $C_2$-$C_{10}$ alkenylene group which may have, a substituent group selected from the group A of substituent groups, a $C_2$-$C_{10}$ alkynylene group which may have a substituent group selected from the group A of substituent groups, $C_3$-$C_7$ cycloaliphatic hydrocarbon group which may have 1 to 3 substituent groups selected from the group A of substituent groups, a $C_6$-$C_{10}$ arylene group which may have 1 to 3 substituent groups selected from the group A of substituent groups;

P' represents a $C_1$-$C_4$ alkyl group which may have a substituent group selected from the group A of substituent groups, a $C_1$-$C_4$ aliphatic acyl group which may have a substituent group selected from the group A of substituent groups, or a $C_7$-$C_{11}$ aromatic acyl group which may have a substituent group selected from the group A of substituent groups;

the group A of substituent groups represents a group including:

halogen;

a hydroxy group;

a carboxy group;

a cyano group;

a $C_1$-$C_6$ alkyl group whose 1 to 3 hydrogen atoms may be substituted by halogen, a hydroxy group, a carboxy group, or a carbamoyl group;

a $C_2$-$C_6$ alkenyl group whose 1 to 3 hydrogen atoms may be substituted by halogen, a hydroxy group, a carboxy group, or a carbamoyl group;

a $C_2$-$C_6$ alkynyl group whose 1 to 3 hydrogen atoms may be substituted by halogen, a hydroxy group, a carboxy group, or a carbamoyl group;

a $C_1$-$C_6$ alkoxy group whose 1 to 3 hydrogen atoms may be substituted by halogen, a hydroxy group, a carboxy group, or a carbamoyl group;

a $C_1$-$C_6$ alkylthio group whose 1 to 3 hydrogen atoms may be substituted by halogen, a hydroxy group, a carboxy group, or a carbamoyl group;

a $C_3$-$C_7$ cycloaliphatic hydrocarbon group whose 1 to 3 hydrogen atoms may be substituted by halogen, a hydroxy group, a carboxy group, or a carbamoyl group;

a $C_7$-$C_{16}$ aralkyl group whose 1 to 3 hydrogen atoms may be substituted by halogen, a hydroxy group, a carboxy group, or a carbamoyl group;

a carbamoyl group which may be monosubstituted or disubstituted by a substituent group selected from a $C_1$-$C_4$ alkoxycarbonyl group, a $C_1$-$C_4$ alkyl group, a alkylsulfonyl group, or a $C_6$-$C_{10}$ arylsulfonyl group;

a $C_6$-$C_{10}$ aryl group whose 1 to 3 hydrogen atoms may be substituted by halogen, a hydroxy group, a carboxy group, or a carbamoyl group; and a 5- to 7-membered aromatic heterocyclic group whose 1 to 3 hydrogen atoms may be substituted by halogen, a hydroxy group, a carboxy group, or a carbamoyl group.

[20] A preferable carbazole derivative, solvate thereof, or pharmaceutically acceptable salt thereof among those represented by the general formula (I″) is the carbazole derivative, solvate thereof, or pharmaceutically acceptable salt thereof as described in the above-mentioned [19], wherein in the formula (I″):

the ring A represents {phenyl group, indenyl group, 1-naphthyl group, or 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups;

X represents =N—, —O—, or —S—;

Y represents =N—, —O—, or —S—;

a and b may be same or different, and represent a $C_1$-$C_4$ alkylene group whose 1 or 2 hydrogens may be substituted by {halogen, a $C_1$-$C_4$ alkyl group, or a $C_1$-$C_4$ alkoxy group};

Z represents a methylene group, —NH—, —O—, —S—, or —S(=O)—;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by a substituent group selected from the group C of substituent groups, a $C_1$-$C_4$ alkoxy group whose 1 to 3 hydrogens may be substituted by a substituent group selected from the group C of substituent groups, or a $C_1$-$C_4$ alkylthio group whose 1 to 3 hydrogens may be substituted by a substituent group selected from the group C of substituent groups, where the group C of substituent groups represents a group including halogen, a $C_1$-$C_4$ alkyl group, a $C_1$-$C_4$ alkoxy group, and a $C_1$-$C_4$ haloalkyl group;

T represents —OH, —OP, or —V—W—P′

P represents a $C_1$-$C_4$ alkyl group, a $C_1$-$C_4$ aliphatic acyl group, or a $C_7$-$C_{11}$ aromatic acyl group;

V represents a methylene group, —NH—, —O—, —S—, or —S(=O)—;

W represents a $C_1$-$C_{10}$ alkylene group which may have a substituent group selected from the group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group;

P′ represents a $C_1$-$C_4$ alkyl group, a $C_1$-$C_4$ aliphatic acyl group, or a $C_7$-$C_{11}$ aromatic acyl group.

[21] A more preferable carbazole derivative, solvate thereof, or pharmaceutically acceptable salt thereof among those represented by the general formula (I″) is the carbazole derivative, solvate thereof, or pharmaceutically acceptable salt thereof as described in the above-mentioned [19], wherein in the formula (I″):

the ring A represents {a phenyl group, an indenyl group, 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or an azepinyl group} which may have 1 to 3 substituent groups selected from the group A of substituent groups;

X represents =N—, —O—, or —S—;

Y represents =N—, —O—, or —S—;

a and b may be same or different, and represent a $C_1$-$C_4$ alkylene group whose 1 or 2 hydrogens may be substituted by {halogen, a $C_1$-$C_4$ alkyl group, or a $C_1$-$C_4$ alkoxy group};

Z represents a methylene group, —NH—, —O—, —S—, or —S(=O)—;

R′ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by {a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {a $C_1$-$C_4$ alkyl group, a $C_1$-$C_4$ alkoxy group, or a $C_1$-$C_4$ haloalkyl group}, or a $C_1$-$C_4$ alkylthio group whose 1 to 3 hydrogens may be substituted by {a $C_1$-$C_4$ alkyl group, a $C_1$-$C_4$ alkoxy group, or a $C_1$-$C_4$ haloalkyl group};

T represents —OH, —OP, or —V—W—P′;

P represents a $C_1$-$C_4$ alkyl group, a $C_1$-$C_4$ aliphatic acyl group, or a $C_7$-$C_{11}$ aromatic acyl group;

V represents a methylene group, —NH—, —O—, —S—, or —S(=O)—;

W represents a $C_1$-$C_{10}$ alkylene group which may have a substituent group selected from the group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, a and $C_6$-$C_{10}$ aryl group; and P′ represents a $C_1$-$C_4$ alkyl group, a $C_1$-$C_4$ aliphatic acyl group, or a $C_7$-$C_{11}$ aromatic acyl group.

[22] A more preferable carbazole derivative, solvate thereof, or pharmaceutically acceptable salt thereof among those represented by the general formula (I″) is the carbazole derivative, solvate thereof, or pharmaceutically acceptable salt thereof as described in the above-mentioned [19], wherein in the formula (I″):

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, an thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X represents =N—, —O—, or —S—;
Y represents =N—, —O—, or —S—;
a and b may be same or different, and represent a $C_1$-$C_4$ alkylene group;
Z represents a methylene group, —NH—, —O—, —S—, or —S(=O)—;
$R^1$ represents a $C_1$-$C_4$ alkyl group, or a $C_1$-$C_4$ alkoxy group;
$R^2$ represents a hydrogen atom, a $C_1$-$C_4$ alkoxy group, or a $C_1$-$C_4$ alkylthio group;
T represents —OH, —OP, or —V—W—P′;
P represents an allyl group, a benzyl group, a methoxymethyl group, or a t-butyl group;
V represents a methylene group, —NH—, —O—, —S—, or —S(=O)—;
W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, or {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group}; and
P′ represents a $C_1$-$C_4$ alkyl group, an allyl group, a benzyl group, or a methoxymethyl group.

[23] A more preferable carbazole derivative, solvate thereof, or pharmaceutically acceptable salt thereof among those represented by the general formula (I″) is the carbazole derivative, solvate thereof, or pharmaceutically acceptable salt thereof as described in the above-mentioned [19], wherein in the formula (I″):

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X and Y represent any one of: (i) X representing —O— and Y representing =N—, (ii) X representing =N— and Y representing —O— or —S—, and (iii) X representing —S— and Y representing =N—;
a and b may be same or different, and represent a $C_1$-$C_4$ alkylene group;
Z represents —NH—, —O—, —S—, or —S(=O)—;
$R^1$ represents a $C_1$-$C_4$ alkyl group, or a $C_1$-$C_4$ alkoxy group;
$R^2$ represents a hydrogen atom, a $C_1$-$C_4$ alkoxy group, or a $C_1$-$C_4$ alkylthio group;
T represents —OH, —OP, or —V—W—P′;
P represents an allyl group, a benzyl group, a methoxymethyl group, or a t-butyl group;
V represents —NH—, —O—, —S—, or —S(=O)—;
W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, or {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group}; and
P′ represents a $C_1$-$C_4$ alkyl group, an allyl group, a benzyl group, or a methoxymethyl group.

The compounds of the present invention show an extremely excellent inhibitory effect or partial inhibitory effect (or partial agonistic effect) against the PPARγ. Also, the compounds of the present invention include ones that show a PPARα agonistic effect. Hence, the compounds of the present invention can be described as compounds having a PPAR modulator activity. Therefore, the compounds of the present invention can be used to regulate the PPAR, so that they are effective for prevention and/or therapy of the PPAR involved disorders. Specifically, the compounds of the present invention are effective for prevention and/or therapy of metabolic syndrome. Also, medical compositions or medicines of the present invention including the compounds of the present invention as active ingredients have an adipose tissue weight reducing effect, hypoglycemic effect, and hypolipidemic effect, so that they are effective as therapeutic agents and/or preventive agents for various disorders such as fatty liver, lipid metabolism abnormality, obesity, visceral adiposity, diabetes, hyperlipemia, impaired glucose tolerance, hypertension, non-alcoholic fatty liver disease, and non-alcoholic steatohepatitis.

According to the present invention, novel intermediate compounds for the preparation of the compounds of the present invention can be provided.

BEST MODE OF CARRYING OUT THE INVENTION

1. Carbazole Derivatives, Solvates Thereof, or Pharmaceutically Acceptable Salts Thereof Hereinafter, the carbazole derivatives, solvates thereof, or pharmaceutically acceptable salts thereof of the present invention (which may be referred to as "the compounds of the present invention") will be described. The carbazole derivative of the present invention is represented by the following general formula (I):

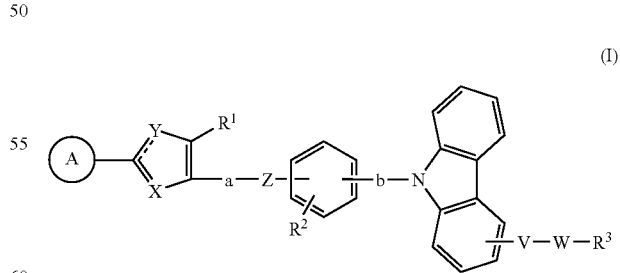

In the formula (I),
a ring A represents a $C_6$-$C_{10}$ aryl group which may have 1 to 3 substituent groups selected from a group A of substituent groups, or a 5- to 7-membered aromatic heterocyclic group which may have 1 to 3 substituent groups selected from the group A of substituent groups;

X represents =N—, =CH—, —O—, or —S—;

Y represents =N—, —O—, or —S—;

a and b may be same or different, and represent a $C_1$-$C_4$ alkylene group which may have a substituent group selected from the group A of substituent groups, a $C_2$-$C_4$ alkenylene group which may have a substituent group selected from the group A of substituent groups, or a $C_2$-$C_4$ alkynylene group which may have a substituent group selected from the group A of substituent groups;

V and Z may be same or different, and represent a methylene group, =N—, —NH—, —O—, —S—, —S(=O)—, —S(=O)$_2$—, —C(=O)—, —C(=O)NH—, or —NHC(=O)—;

W represents a $C_1$-$C_{10}$ alkylene group which may have a substituent group selected from the group A of substituent groups, a $C_2$-$C_{10}$ alkenylene group which may have a substituent group selected from the group A of substituent groups, a $C_2$-$C_{10}$ alkynylene group which may have a substituent group selected from the group A of substituent groups, a $C_3$-$C_7$ cycloaliphatic hydrocarbon group which may have 1 to 3 substituent groups selected from the group A of substituent groups, or a $C_6$-$C_{10}$ arylene group which may have 1 to 3 substituent groups selected from the group A of substituent groups;

$R^1$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, or a $C_1$-$C_4$ alkoxy group which may have a substituent group selected from the group A of substituent groups;

$R^2$ represents, a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups;

$R^3$ represents a hydrogen atom, a hydroxy group, a cyano group, —C(=O)$R^4$ ($R^4$ represents a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups), or —C(=O)$NR^5R^6$ ($R^5$ and $R^6$ may be same or different, and represent a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, a $C_1$-$C_4$ alkylsulfonyl group which may have a substituent group selected from the group A of substituent groups, or a $C_6$-$C_{12}$ arylsulfonyl group which may have a substituent group selected from the group A of substituent groups), the group A of substituent groups represents a group including:

halogen; a hydroxy group; a carboxy group; a cyano group;

a $C_1$-$C_6$ alkyl group whose 1 to 3 hydrogen atoms may be substituted by halogen, a hydroxy group, a carboxy group, or a carbamoyl group;

a $C_2$-$C_6$ alkenyl group whose 1 to 3 hydrogen atoms may be substituted by halogen, a hydroxy group, a carboxy group, or a carbamoyl group;

a $C_2$-$C_6$ alkynyl group whose 1 to 3 hydrogen atoms may be substituted by halogen, a hydroxy group, a carboxy group, or a carbamoyl group;

a $C_1$-$C_6$ alkoxy group whose 1 to 3 hydrogen atoms may be substituted by halogen, a hydroxy group, a carboxy group, or a carbamoyl group;

a $C_1$-$C_6$ alkylthio group whose 1 to 3 hydrogen atoms may be substituted by halogen, a hydroxy group, a carboxy group, or a carbamoyl group;

a $C_3$-$C_7$ cycloaliphatic hydrocarbon group whose 1 to 3 hydrogen atoms may be substituted by halogen, a hydroxy group; a carboxy group, or a carbamoyl group;

a $C_7$-$C_{16}$ aralkyl group whose 1 to 3 hydrogen atoms may be substituted by halogen, a hydroxy group, a carboxy group, or a carbamoyl group;

a carbamoyl group which may be monosubstituted or disubstituted by a substituent group selected from a $C_1$-$C_4$ alkoxycarbonyl group, a $C_1$-$C_4$ alkyl group, a $C_1$-$C_4$ alkylsulfonyl group, and a $C_6$-$C_{10}$ arylsulfonyl group;

a $C_6$-$C_{10}$ aryl group whose 1 to 3 hydrogen atoms may be substituted by halogen, a hydroxy group, a carboxy group, or a carbamoyl group; and a 5- to 7-membered aromatic heterocyclic group whose 1 to 3 hydrogen atoms may be substituted by halogen, a hydroxy group, a carboxy group, or a carbamoyl group. It is to be noted that the carbazole derivative represented by the formula (I) is preferably the carbazole derivative represented by the above-mentioned I').

In the present specification, the "$C_m$-$C_n$" implies that the carbon number is any number from m to n.

The "aryl group" is a univalent group derived from an aromatic hydrocarbon by removal of one hydrogen atom bonded to the ring. As the $C_6$-$C_{10}$ aryl group, a phenyl group, an indenyl group, a 1-naphthyl group, and a 2-naphthyl group can be mentioned.

The "aromatic heterocyclic group" is a heterocyclic group having within the ring 1 to 3 hetero atoms selected from a group including an oxygen atom, a nitrogen atom, and a sulfur atom. As the 5- to 7-membered aromatic heterocyclic group, a 5-membered aromatic heterocyclic group such as furyl, thienyl, pyrrolyl, pyrazolyl, imidazolyl, oxazolyl, isoxazolyl, thiazolyl, isothiazolyl, 1,2,3-oxadiazolyl, triazolyl, or thiadiazolyl; a 6-membered aromatic heterocyclic group such as pyranyl, pyridyl, pyridazinyl, pyrimidinyl, or pyrazinyl; or a 7-membered aromatic heterocyclic group such as azepinyl can be mentioned. As the aromatic heterocyclic group, the 5-membered aromatic heterocyclic group or the 6-membered aromatic heterocyclic group is preferable.

The "alkylene group" is a bivalent group derived by removal of two hydrogen atoms from a straight-chain or branched-chain aliphatic hydrocarbon. As the $C_1$-$C_{10}$ alkylene group, a methylene group, a methylmethylene group, an ethylene group, a propylene group, a trimethylene group, a 1-methylethylene group, a tetramethylene group, a 1-methyltrimethylene group, a 2-methyltrimethylene group, a 3-methyltrimethylene group, a 1-methylpropylene group, a 1,1-dimethylethylene group, a pentamethylene group, a 1-methyltetramethylene group, a 2-methyltetramethylene group, a 3-methyltetramethylene group, a 4-methyltetramethylene group, a 1,1-dimethyltrimethylene group, a 2,2-dimethyltrimethylene group, a 3,3-dimethyltrimethylene group, a hexamethylene group, a 1-methylpentamethylene group, a 2-methylpentamethylene group, a 3-methylpentamethylene group, a 4-methylpentamethylene group, a 5-methylpentamethylene group, a 1,1-dimethyltetramethylene group, a 2,2-dimethyltetramethylene group, a 3,3-dimethyltetramethylene group, a 4,4-dimethyltetramethylene group, a heptamethylene group, a 1-methylhexamethylene group, a 2-methylhexamethylene group, a 5-methylhexamethylene group, a 3-ethylpentamethylene group, an octamethylene group, a 2-methylheptamethylene group, a 5-methylheptamethylene group, a 2-ethylhexamethylene group, a 2-ethyl-3-methylpentamethylene group, and a 3-ethyl-2-methylpentamethylene group can be mentioned. As the alkylene group, the $C_1$-$C_4$ alkylene group is preferable, and the $C_1$-$C_2$ alkylene group is more preferable.

The "alkenylene group" is a bivalent group derived by removal of two hydrogen atoms from a straight-chain or branched-chain aliphatic hydrocarbon having a double bond. As the $C_2$-$C_{10}$ alkenylene group, an etenylene group, a 1-propenylene group, a 2-propenylene group, a 2-methyl-1-propenylene group, a 1-butenylene group, a 2-butenylene group, a 3-butenylene group, a 3-methyl-2-butenylene group, a 1-pentenylene group, a 2-pentenylene group, a 3-pentenylene group, a 4-pentenylene group, and a 1-hexenylene group can be mentioned.

The "alkynylene group" is a bivalent group derived by removal of two hydrogen atoms from a straight-chain or branched-chain aliphatic hydrocarbon having a triple bond. As the $C_2$-$C_{10}$ alkynylene group, an ethynylene group, a 1-propynylene group, a 2-propynylene group, a 2-methyl-1-propynylene group, a 1-butynylene group, a 2-butynylene group, a 3-butynylene group, a 3-methyl-2-butynylene group, a 1-pentynylene group, a 2-pentynylene group, a 3-pentynylene group, a 4-pentynylene group, and a 1-hexynylene group can be mentioned.

The "cycloaliphatic hydrocarbon group" means a saturated or unsaturated cycloaliphatic hydrocarbon group. As the $C_3$-$C_7$ cycloaliphatic hydrocarbon group, a cycloalkyl group such as a cyclopropyl group, a cyclobutyl group, cyclohexyl group, and cyclopentyl group; or a cycloalkenyl group such as a 2-cyclopentene-1-yl group, a 2-cyclohexene-1-yl group, and a 3-cyclohexene-1-yl group can be mentioned.

The "arylene group" is a bivalent group derived from an aromatic hydrocarbon by removal of two hydrogen atoms bonded to the ring. As a ring composing a $C_6$-$C_{10}$ arylene group, a benzene ring or a naphthalene ring can be mentioned.

The "alkyl group" is a univalent group derived by removal of one hydrogen atom from a straight-chain or branched-chain aliphatic hydrocarbon. As the $C_1$-$C_6$ alkyl group, a methyl group, an ethyl group, a propyl group, an isopropyl group, a butyl group, an isobutyl group, a sec-butyl group, a tert-butyl group, a pentyl group, an isopentyl group, a neopentyl group, a hexyl group, and an isohexyl group can be mentioned. As the $C_1$-$C_4$ alkyl group, a methyl group, an ethyl group, a propyl group, an isopropyl group, a butyl group, an isobutyl group, a sec-butyl group, and a tert-butyl group can be mentioned.

The "alkenyl group" is a univalent group derived by removal of one hydrogen atom from a straight-chain or branched-chain aliphatic hydrocarbon having a double bond. As the $C_2$-$C_6$ alkenyl group, an etenyl group, a 1-propenyl group, a 2-propenyl group, a 2-methyl-1-propenyl group, a 1-butenyl group, a 2-butenyl group, a 3-butenyl group, a 3-methyl-2-butenyl group, a 1-pentenyl group, a 2-pentenyl group, a 3-pentenyl group, a 4-pentenyl group, and a 1-hexenyl group can be mentioned. As the $C_2$-$C_4$ alkenyl group, an etenyl group, a 1-propenyl group, a 2-propenyl group, a 2-methyl-1-propenyl group, a 1-butenyl group, a 2-butenyl group, and a 3-butenyl group can be mentioned.

The "alkynyl group" is a univalent group derived by removal of one hydrogen atom from a straight-chain or branched-chain aliphatic hydrocarbon having a triple bond. As the $C_2$-$C_6$ alkynyl group, an ethynyl group, a 1-propynyl group, a 2-propynyl group, a 2-methyl-1-propynyl group, a 1-butynyl group, a 2-butynyl group, a 3-butynyl group, a 3-methyl-2-butynyl group, a 1-pentynyl group, a 2-pentynyl group, a 3-pentynyl group, a 4-pentynyl group, and a 1-hexynyl group can be mentioned. As the $C_2$-$C_4$ alkynyl group, an ethynyl group, a 1-propynyl group, a 2-propynyl group, a 2-methyl-1-propynyl group, a 1-butynyl group, a 2-butynyl group, and a 3-butynyl group can be mentioned.

The "alkoxy group" is a univalent group derived by removal of one hydrogen atom from a straight-chain or branched-chain hydroxy group of alcohols. As the $C_1$-$C_6$ alkoxy group, a methoxy group, an ethoxy group, a propoxy group, an isopropoxy group, a butoxy group, an isobutoxy group, a sec-butoxy group, a tert-butoxy group, a pentoxy group, an isopentoxy group, a 2-methylbutoxy group, a neopentoxy group, a 1-ethylpropoxy group, a hexyloxy group, a 4-methylpentoxy group, a 3-methylpentoxy group, a 2-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy, or a 2-ethylbutoxy can be mentioned. As the $C_1$-$C_4$ alkoxy group, a methoxy group, an ethoxy group, a propoxy group, an isopropoxy group, a butoxy group, an isobutoxy group, a sec-butoxy group, and a tert-butoxy group can be mentioned.

The "alkylthio group" is a group having sulfur substituted for oxygen of the alkoxy group. As the $C_1$-$C_6$ alkylthio group, a methylthio group, an ethylthio group, a propylthio group, an isopropylthio group, a butylthio group, an isobutylthio group, a sec-butylthio group, a tert-butylthio group, a pentylthio group, an isopentylthio group, a 2-methylbutylthio group, a neopentylthio group, a 4-methylpentylthio group, a 3-methylpentylthio group, a 2-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio, or a 2-ethylbutylthio can be mentioned. As the $C_1$-$C_4$ alkylthio group, a methylthio group, an ethylthio group, a propylthio group, an isopropylthio group, a butylthio group, an isobutylthio group, a sec-butylthio group, and a tert-butylthio group can be mentioned.

The "alkylsulfonyl group" is a univalent group having one hydrogen atom of the alkyl group substituted by a sulfonyl group. As the $C_1$-$C_4$ alkylsulfonyl group, a methylsulfonyl group, an ethylsulfonyl group, a propylsulfonyl group, an isopropylsulfonyl group, a butylsulfonyl group, an isobutylsulfonyl group, a sec-butylsulfonyl group, and a tert-butylsulfonyl group can be mentioned.

The "arylsulfonyl group" is a univalent group having one hydrogen atom of the aryl group substituted by a sulfonyl group. As the $C_6$-$C_{12}$ arylsulfonyl, a phenylsulfonyl group, an indenylsulfonyl group, a 1-napthylsulfonyl group, a 2-naphthylsulfonyl group, and the like can be mentioned.

As the halogen, fluorine, chlorine, bromine, and iodine can be mentioned.

The "halogenoalkyl group" is a univalent group having one or more hydrogen atoms of the alkyl group substituted by a halogen atom. As the $C_1$-$C_6$ halogenoalkyl group, a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, a 2-fluoroethyl group, a 2-iodoethyl group, a 3-chloropropyl group, a 4-fluorobutyl group, a 6-iodohexyl group, and a 2,2-dibromoethyl group can be mentioned.

The "aralkyl group" is a univalent group having one hydrogen atom from the alkyl group substituted by an aryl group. As the $C_7$-$C_{16}$ aralkyl group, a benzyl group, a napthylmethyl group, an indenylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group, a 1-naphthylpropyl group, a 2-naphthylpropyl group, a 3-naphthylpropyl group, a 1-phenylbutyl group, a 2-phenylbutyl group, a 3-phenylbutyl group, a 4-phenylbutyl group, a 1-naphthylbutyl group, a 2-naphthylbutyl group, a 3-naphthylbutyl group, a 4-naphthylbutyl group, a 5-phenylpentyl group, a 5-naphthylpentyl group, a 6-phenylhexyl group, and a 6-naphthylhexyl group can be mentioned.

The "alkoxycarbonyl group" is a group having a carbonyl group linked to an alkoxy group. As the $C_1$-$C_4$ alkoxycarbonyl group, a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, and a tert-butoxycarbonyl group can be mentioned.

The "aliphatic acyl group" means a group represented by (R—CO—) having a hydrogen atom removed from an aldehyde group of aldehyde. As the $C_1$-$C_4$ aliphatic acyl group, an alkanoyl group such as formyl, acetyl, propionyl, butyryl, or isobutyryl; an alkylcarbonyl halide group such as chloroacetyl, dichloroacetyl, trichloroacetyl, or trifluoroacetyl; a lower alkoxyalkylcarbonyl group such as methoxy acetyl; and an unsaturated alkylcarbonyl group such as acryloyl, propioloyl, or methacryloyl can be mentioned.

The "aromatic acyl group" means a group having a carbonyl group linked to aromatic. The $C_7$-$C_{11}$ aromatic acyl group means a group having the $C_7$-$C_{11}$ aromatic and a carbonyl group linked. As the $C_7$-$C_{11}$ aromatic acyl group, an arylcarbonyl group such as benzoyl, α-naphthoyl, or β-naphthoyl; an arylcarbonyl halide group such as 2-bromobenzoyl, or 4-chlorobenzoyl; a lower alkylated arylcarbonyl group such as 2,4,6-trimethylbenzoyl, or 4-toluoyl; a lower alkoxylated arylcarbonyl group such as 4-anysoyl; a nitrated arylcarbonyl group such as 4-nitro benzoyl, or 2-nitrobenzoyl; a lower alkoxycarbonylated arylcarbonyl group such as 2-(methoxycarbonyl)benzoyl; or an arylated arylcarbonyl group such as 4-phenylbenzoyl can be mentioned.

Hereinafter, each of the substituent groups used for the general formulas will be described. The ring A represents a $C_6$-$C_{10}$ aryl group which may have 1 to 3 substituent groups selected from the group A of substituent groups, or a 5- to 7-membered aromatic heterocyclic group which may have 1 to 3 substituent groups selected from the group A of substituent groups. The group A of substituent groups and preferable ones among the group A of substituent groups will be described later. The ring A preferably represents {a phenyl group, an indenyl group, a 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups; the ring A more preferably represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group}; and the ring A further more preferably represents a phenyl group, a 2-furyl group, a 2-thienyl group, or a 4-pyridyl group.

X represents =N—, =CH—, —O—, or —S—; preferably represents =N—, —O—, or —S—; and more preferably represents —O—. Y represents =N—, —O—, or —S—; and preferably represents =N—. As the combination of X and Y; (i) X representing —O— and Y representing =N—, (ii) X representing =N— and Y representing —O— or —S—, or (iii) X representing —S— and Y representing =N— can be mentioned, wherein (i) X representing —O— and Y representing =N— is preferable.

The linking groups a and b may be same or different, and represent a $C_1$-$C_4$ alkylene group which may have a substituent group selected from the group A of substituent groups, a $C_2$-$C_4$ alkenylene group which may have a substituent group selected from the group A of substituent groups, or a $C_2$-$C_4$ alkynylene group which may have a substituent group selected from the group A of substituent groups; the a and b preferably may be same or different, and represent a $C_1$-$C_4$ alkylene group whose 1 or 2 hydrogens are substituted by {halogen, a $C_1$-$C_4$ alkyl group, or a $C_1$-$C_4$ alkoxy group}; the a and b more preferably may be same or different, and represent a $C_1$-$C_4$ alkylene group; and the a and b further more preferably represent a methylene group.

The V represents a methylene group, =N—, —NH—, —O—, —S—, —S(=O)—, —S(=O)$_2$—, —C(=O)—, —C(=O)NH—, or —NHC(=O)—; more preferably represents =N—, —NH—, —O—, —S—, —S(=O)—, —S(=O)$_2$—, —C(=O)—, —C(=O)NH—, or —NHC(=O)—; further more preferably represents —NH—, —O—, —S—, —S(=O)—, or —C(=O)—; and especially preferably represents —O—.

The Z represents a methylene group, =N—, —NH—, —O—, —S—, —S(=O)—, —S(=O)$_2$—, —C(=O)—, —C(=O)NH—, or —NHC(=O)—; more preferably represents =N—, —NH—, —O—, —S—, —S(=O)—, —S(=O)$_2$—, —C(=O)—, —C(=O)NH—, or —NHC(=O)—; further more preferably represents —NH—, —O—, —S—, —S(=O)—, or —C(=O)—; and especially preferably represents —O—.

The W represents a $C_1$-$C_{10}$ alkylene group which may have a substituent group selected from the group A of substituent groups, a $C_2$-$C_{10}$ alkenylene group which may have a substituent group selected from the group A of substituent groups, a $C_2$-$C_{10}$ alkynylene group which may have a substituent group selected from the group A of substituent groups, a $C_3$-$C_7$ cycloaliphatic hydrocarbon group which may have 1 to 3 substituent groups selected from the group A of substituent groups, or a $C_6$-$C_{10}$ arylene group which may have 1 to 3 substituent groups selected from the group A of substituent groups. W preferably represents a $C_1$-$C_{10}$ alkylene group which may have a substituent group selected from the group B of substituent groups, a $C_2$-$C_6$ alkenylene group which may have a substituent group selected from a group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group. The W more preferably represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, or {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group}; and further more preferably represents a $C_1$-$C_{10}$ alkylene group whose 1 or 2 hydrogens may be substituted by a phenyl group or a $C_1$-$C_6$ alkyl group, a 1,2-phenylene group, or a 1,3-cyclohexyl group. The W more preferably represents a $C_1$-$C_4$ alkylene group whose 1 or 2 hydrogens may be substituted by a $C_1$-$C_4$ alkyl group. The W especially preferably represents a methylene group, a methylmethylene group, a dimethylmethylene group, an ethylmethylene group, an isopropylmethylene group, an ethylene group, a methylethylene group, or an isopropylethylene group.

The $R^1$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, or a $C_1$-$C_4$ alkoxy group which may have a substituent group selected from the group A of substituent groups; preferably represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}; more preferably represents a $C_1$-$C_4$ alkyl group, or a $C_1$-$C_4$ alkoxy group; and further more preferably represents a methyl group.

The $R^2$ represents, a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups; more preferably represents a hydrogen atom, a $C_1$-$C_4$ alkyl group whose 1 to 3 hydrogens may be substituted by a substituent group selected from a group C of substituent groups, a $C_1$-$C_4$ alkoxy group whose 1 to 3 hydrogens may be substituted by a substituent group selected from the group C of substituent groups, or a $C_1$-$C_4$ alkylthio group whose 1 to 3 hydrogens may be substituted by a substituent group selected from the group C of substituent groups, where the group C of substituent groups represents a group including halogen, a $C_1$-$C_4$ alkyl group, a $C_1$-$C_4$ alkoxy group, and a $C_1$-$C_4$ haloalkyl group; more preferably represents a hydrogen atom, a $C_1$-$C_4$ alkyl group whose 1 to 3 hydrogens may be substituted by {a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {a $C_1$-$C_4$ alkyl group, a $C_1$-$C_4$ alkoxy group, or a $C_1$-$C_4$ haloalkyl group}, or a $C_1$-$C_4$ alkylthio group whose 1 to 3 hydrogens may be substituted by {a $C_1$-$C_4$ alkyl group, a $C_1$-$C_4$ alkoxy group, or a $C_1$-$C_4$ haloalkyl group}; further more preferably represents a hydrogen atom, a $C_1$-$C_4$ alkoxy group, or a $C_1$-$C_4$ alkylthio group; and especially preferably represents a methoxy group.

The $R^3$ represents a hydrogen atom, a hydroxy group, a cyano group, —C(=O)$R^4$, or —C(=O)NR$^5$R$^6$; preferably represents a hydroxy group, or —C(=O)$R^4$; and more preferably represents a carboxy group.

In the above-mentioned —C(=O)$R^4$, the $R^4$ represents a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups; preferably represent a hydrogen atom, a hydroxy group, a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}; more preferably represents a hydrogen atom, hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}; and especially preferably represents a hydroxy group or a $C_1$-$C_4$ alkoxy group.

In the above-mentioned —C(=O)NR$^5$R$^6$, the $R^5$ and $R^6$ may be same or different, and represent a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, a $C_1$-$C_4$ alkylsulfonyl group which may have a substituent group selected from the group A of substituent groups, or a $C_6$,—$C_{1\text{-}2}$ arylsulfonyl group which may have a substituent group selected from the group A of substituent groups; preferably represent a hydrogen atom, a hydroxy group, a $C_1$-$C_4$ alkyl group, a $C_1$-$C_4$ alkoxy group, a $C_1$-$C_4$ alkylsulfonyl group, or a $C_6$,—$C_{1\text{-}2}$ arylsulfonyl group; and more preferably represent a hydrogen atom, a hydroxy group, a $C_1$-$C_4$ alkyl group, or a $C_1$-$C_4$ alkoxy group.

The group A of substituent groups represents a group including: halogen; a hydroxy group; a carboxy group; a cyano group; a $C_1$-$C_6$ alkyl group whose 1 to 3 hydrogen atoms may be substituted by halogen, a hydroxy group, a carboxy group, or a carbamoyl group; a $C_2$-$C_6$ alkenyl group whose 1 to 3 hydrogen atoms may be substituted by halogen, a hydroxy group, a carboxy group, or a carbamoyl group; a $C_2$-$C_6$ alkynyl group whose 1 to 3 hydrogen atoms may be substituted by halogen, a hydroxy group, a carboxy group, or a carbamoyl group; a $C_1$-$C_6$ alkoxy group whose 1 to 3 hydrogen atoms may be substituted by halogen, a hydroxy group, a carboxy group, or a carbamoyl group; a $C_1$-$C_6$ alkylthio group whose 1 to 3 hydrogen atoms may be substituted by halogen, a hydroxy group, a carboxy group, or a carbamoyl group; a $C_3$-$C_7$ cycloaliphatic hydrocarbon group whose 1 to 3 hydrogen atoms may be substituted by halogen, a hydroxy group, a carboxy group, or a carbamoyl group; a aralkyl group whose 1 to 3 hydrogen atoms may be substituted by halogen, a hydroxy group, a carboxy group, or a carbamoyl group; a carbamoyl group which may be monosubstituted or disubstituted by a substituent group selected from a $C_1$-$C_4$ alkoxycarbonyl group, a $C_1$-$C_4$ alkyl group, a $C_1$-$C_4$ alkylsulfonyl group, and a $C_6$-$C_{10}$ arylsulfonyl group; a $C_6$-$C_{10}$ aryl group whose 1 to 3 hydrogen atoms may be substituted by halogen, a hydroxy group, a carboxy group, or a carbamoyl group; and a 5- to 7-membered aromatic heterocyclic group whose 1 to 3 hydrogen atoms may be substituted by halogen, a hydroxy group, a carboxy group, or a carbamoyl group; preferably represents a group including: halogen; a hydroxy group; a carboxy group; a cyano group; halogen, a hydroxy group, a $C_1$-$C_6$ alkyl group; a $C_2$-$C_6$ alkenyl; a $C_2$-$C_6$ alkynyl group; a $C_1$-$C_6$ alkoxy group; a $C_1$-$C_6$ alkylthio group; a $C_3$-$C_7$ cycloaliphatic hydrocarbon group; a $C_7$-$C_{16}$ aralkyl group; a $C_1$-$C_4$ alkoxycarbonyl group, a carbamoyl group; a $C_6$-$C_{10}$ aryl group; and a 5- to 7-membered aromatic heterocyclic group; more preferably represents a group (group B of substituent groups) including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group; and further more preferably represents a group (group C of substituent groups) including halogen, a $C_1$-$C_4$ alkyl group, a $C_1$-$C_4$ alkoxy group, and a $C_1$-$C_4$ haloalkyl group.

The P represents a $C_1$-$C_4$ alkyl group which may have a substituent group selected from the group A of substituent groups, a $C_1$-$C_4$ aliphatic acyl group which may have a substituent group selected from the group A of substituent groups, or a $C_7$-$C_{11}$ aromatic acyl group which may have a substituent group selected from the group A of substituent groups; preferably represents a $C_1$-$C_4$ alkyl group which may have a substituent group selected from the group B of substituent groups, a $C_1$-$C_4$ aliphatic acyl group which may have a substituent group selected from the group B of substituent groups, or a $C_7$-$C_{11}$ aromatic acyl group which may have a substituent group selected from the group B of substituent groups; more preferably represents a $C_1$-$C_4$ alkyl group, a $C_1$-$C_4$ aliphatic acyl group, or a $C_7$-$C_{11}$ aromatic acyl group; and further more preferably represents an allyl group, a benzyl group, a methoxymethyl group, or a t-butyl group.

The P' represents a $C_1$-$C_4$ alkyl group which may have a substituent group selected from the group A of substituent groups, a $C_1$-$C_4$ aliphatic acyl group which may have a substituent group selected from the group A of substituent groups, or a $C_7$-$C_{11}$ aromatic acyl group which may have a substituent group selected from the group A of substituent groups; preferably represents a $C_1$-$C_4$ alkyl group which may have a substituent group selected from the group B of substituent groups, a $C_1$-$C_4$ aliphatic acyl group which may have a substituent group selected from the group B of substituent groups, or a $C_7$-$C_{11}$ aromatic acyl group which may have a substituent group selected from a group B; and more preferably represents a $C_1$-$C_4$ alkyl group, a $C_1$-$C_4$ aliphatic acyl group, or a $C_7$-$C_{11}$ aromatic acyl group; and more preferably represents a $C_1$-$C_4$ alkyl group, an allyl group, a benzyl group, or a methoxymethyl group.

The "solvate thereof" means a solvate of the carbazole derivative. As a solvate, a hydrate can be mentioned. Also, by being left in the atmosphere or recrystallized, the compounds of the present invention may absorb moisture, may have absorbed water attached thereto, or may become a hydrate. Even when such solvates are formed, they are included in the "solvate thereof".

The "salt thereof" in the "pharmaceutically acceptable salt thereof" means a salt of the carbazole derivative (I). It is to be noted that in the present specification, "pharmaceutically acceptable" means to be unharmful to the recipient. The carbazole derivative (I) of the present invention can be made into a salt by an ordinary method or by a method which will be described later. As the salt thereof, for example, alkali metal salt such as sodium salt, potassium salt, and lithium salt; alkaline earth metal salt such as calcium salt, and magnesium salt; metal salt such as aluminum salt, iron salt, zinc salt, copper salt, nickel salt, and cobalt salt; inorganic salt such as ammonium salt; amine salt such as organic salt such as t-octylamine salt, dibenzylamine salt, morpholine salt, glucosamine salt, phenylglycinealkylester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-N-phenethylamine salt, piperazine salt, tetramethylammonium salt, and tris(hydroxymethyl)aminomethane salt; hydrohalic acid salt such as hydrofluoric acid, hydrochloric acid, hydrobromic acid, and hydriodic acid; inorganic acid salt such as nitrate salt, perchlorate salt, sulfate salt, and phosphoric salt, or lower alkanesulfonic acid salt such as methanesulfonic acid, trifluoromethanesulfonic acid, and ethanesulfonic acid; aryl sulfonic acid salt such as benzenesulfonic acid, p-toluenesulfonic acid, and the like; amino acid salt such as glutamic acid, and asparatic acid; organic acid of carboxylic acid salt such as fumaric acid, succinic acid, citric acid, tartaric acid, oxalic acid, and maleic acid; and amino acid salt such as ornithine acid salt, glutamate, and aspartate can be mentioned. Among these, the alkali metal salt is preferable, while the sodium salt is more preferable.

In the compounds of the present invention, various isomers are included. For example, the carbazole derivative (I) of the above-mentioned general formula (I) includes an asymmetric carbon, and since there are cases where an asymmetric carbon is present on the substituent group, the optical isomer is included. For the compounds of the present invention, stereoisomers of an R configuration and S configuration exist. The compounds of the present invention include compounds including each of the stereoisomers or including the stereoisomers by arbitrary proportion. Such stereoisomers can be prepared by using optically-active ingredient to synthesize the compounds of the present invention or by optically resolving the prepared compounds of the present invention as desired by using a normal optical resolution method or separation method. More specifically, the optical resolution can be carried out by methods disclosed in the examples which will be described later. Moreover, geometric isomers such as cis forms and trans forms may be present in the compounds of the present invention. The compounds of the present invention include compounds including each of the geometric isomers or including the geometric isomers by arbitrary proportion.

Moreover, the compounds of the present invention include compounds that are metabolized within an organism and converted into the compounds of the present invention, so-called prodrugs.

2. Method for Preparation of the Compounds of the Present Invention

The compounds of the present invention represented by the general formula (I) can be prepared according to the following method A and method B, for example:

2.1. Method for Preparation of the Compounds of the Present Invention

Method A

Hereinafter, an example (method A) of the method for preparation of the compounds of the present invention represented by the general formula (I) will be described. The method A includes processes shown in the following process chart:

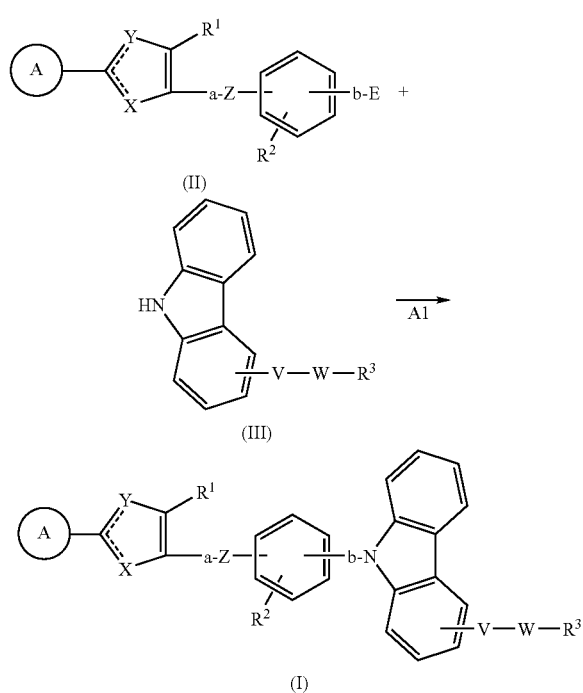

In the above-mentioned formulas, A, V, W, X, Y, Z, a, b, $R^1$, $R^2$, and $R^3$ respectively represent synonymous definition with those mentioned above. E represents a leaving group. As an example of E, a hydroxyl group, a halogen atom, or —$OSO_2R^7$ ($R^7$ is a methyl group, a trifluoromethyl group, a phenyl group, a tolyl group, or a nitrophenyl group.) can be mentioned. As a more specific E, a chlorine atom or a bromine atom can be mentioned.

As described above, the method A is a method for preparation of the compound (I) from the compound represented by the general formula (II) and the carbazole derivative represented by the general formula (III). The process A1 can be carried out according to a constantly carried out method in the field of organic synthesis and the like. The process A 1 is generally carried out in an inert solvent. The process A1 may be carried out under the presence of a catalyst. The process A1 may be carried out under the presence of a base. In such a case, the compound (II) should be dissolved in an inert solvent, a base may be added under stirring or without stirring, and then the compound (III) may be added under stirring or without stirring.

The compound represented by the general formula (II) can be prepared according to a publicly known production method such as one disclosed by WO01/38325, or a production method or the like which will be described later. Also, the compound represented by the general formula (III) can be prepared according to a publicly known production method such as one disclosed by DE2243574, or a production method or the like which will be described later.

The inert solvents used for the process A1 are not specifically limited as long as they are inactive against the above-mentioned reaction. As such inert solvents, ethers such as diethylether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidon; sulfoxides such as dimethylsulfoxide can be mentioned. These can be used singly or as a mixture of two or more kinds in appropriate proportions. Among these inert solvents, the amides such as the N,N-dimethylformamide are preferable.

As the bases used for the process A1, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, LiHMDS can be mentioned. Specifically when E in the formula is a halogen atom, alkali metal hydroxide, metal hydride, or metal alkoxide is preferable among these bases. As the amount of the base, 1-5 mol equivalent weight for the compound (III) can be mentioned.

While the reaction temperature in the process A1 may be adjusted according to the ingredient, the solvent, the base, and the like in the process A1, it is usually −40° C. to 150° C., and preferably −10° C. to 120° C. The reaction temperature in the process A1 may be 10° C. to 50° C.

While the reaction time in the process A1 may be adjusted according to the ingredient, the solvent, the base, and the like in the process A1, it is usually 0.5 hour to 24 hours and preferably 0.5 hour to 2 hours.

The compound (I) of the present invention is prepared from the reaction mixture after completing the process A1 according to a method generally used in the field of the organic synthesis. For example, when the target compound is an insoluble precipitate, the target compound can be prepared by filtration of the reaction mixture, followed by washing with a solvent. Also, when the target compound is not an insoluble precipitate, the target compound can be prepared by using nonmiscible liquids such as organic solvent and water for separation, separating an organic layer including the target compound, followed by washing with water or the like and drying (extraction).

The prepared target compound may be separated and/or purified as necessary. For such a separating and/or refining method, a method generally used in the field of organic synthesis may be adopted. As such a separating and/or refining method, a method can be mentioned where recrystallization, reprecipitation, chromatography, elution by the eluent, and the like are arbitrarily combined.

It is to be noted that the compound (I) of the present invention may be extracted after changing the carboxyl group at the end into salt such as alkali metal.

Also, in case the compound (I) of the present invention has optical isomers, they may be separated and/or synthesized by a publicly known method. For example, an optical active material may be prepared by using an optically-active intermediate. Also, at the final process of the synthesis or the like, the optical active material may be prepared by using an asymmetric reaction. Moreover, the optical active material may be prepared by performing an optical resolution to the mixture according to usual methods. It is to be noted that the above-mentioned optically-active intermediate can be prepared by utilizing chiral synthesis, asymmetric reaction, or optical resolution in the same way as mentioned above.

2.2. Method for Preparation of the Compounds of the Present Invention

Method B

Hereinafter, an example of a method (method B) for preparation of the compounds of the present invention represented by the general formula (I) which is different from the above-mentioned method will be described. The method B includes the processes shown in the following process chart.

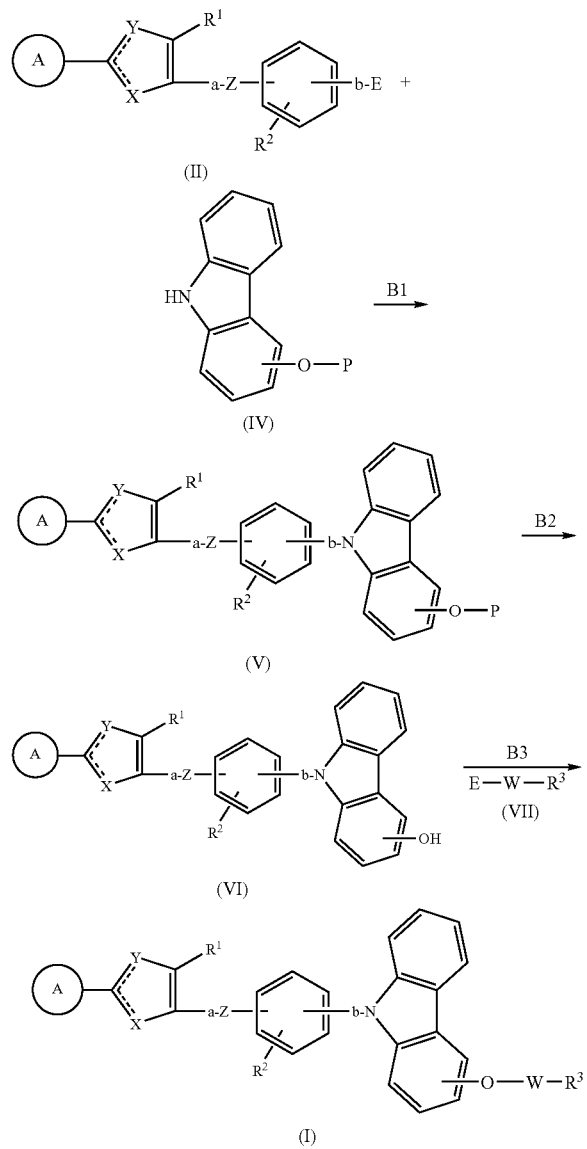

In the above-mentioned formulas, A, W, X, Y, Z, b, $R^1$, $R^2$, and $R^3$ respectively represent synonymous definition with those mentioned above. As an example of E, a hydroxyl group, a halogen atom, or —$OSO_2R^7$ ($R^7$ is a methyl group, a trifluoromethyl group, a phenyl group, a tolyl group, or a nitrophenyl group.) can be mentioned. As a more specific E, a chlorine atom or a bromine atom can be mentioned. P represents a protecting group. As P, a $C_1$-$C_4$ aliphatic acyl group, a $C_7$-$C_{11}$ aromatic acyl group, or a $C_1$-$C_4$ alkoxy-$C_1$-$C_4$ alkyl group can be mentioned. As a specific P, an allyl group, a benzyl group, a methoxymethyl group, a tert-butyl group, or the like can be mentioned. As a more specific P, an allyl group can be mentioned.

As described above, the method B is a method for preparation of the compound (I) from the compound represented by the general formula (II) and the carbazole derivative represented by the general formula (IV). The method B is a production method especially effective in case V is O (oxygen atom) in the general formula (I).

2.2.1. Process B1

The process B1 is a process for preparation of a compound represented by the general formula (V) from the compound represented by the general formula (II) and the carbazole derivative represented by the general formula (IV). The process B1 can be carried out according to a constantly carried out method in the field of organic synthesis and the like. The process B1 is generally carried out in an inert solvent. The process B1 may be carried out under the presence of a base. In such a case the compound (II) may be dissolved in an inert solvent, a base may be added under stirring or without stirring, and then the compound (IV) may be added under stirring or without stirring.

The inert solvents used for the process B1 are not specifically limited as long as they are inactive against the above-mentioned reaction. As such inert solvents, alcohols such as methanol, ethanol, and isopropanol; ethers such as diethylether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. These inert solvents can be used singly or as a mixture of two or more kinds. Among these inert solvents, amides are preferable.

As the bases used for the process B1, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, and LiHMDS can be mentioned. Among these bases, alkali metal hydroxide or metal hydride is preferable. Specifically, when the E is a halogen atom, sodium hydroxide, potassium hydroxide, or sodium hydride is preferable among these bases.

A preferable aspect of the process B1 is dissolving the compound (II) in the inert solvent while stirring the solution, followed by adding the base while stirring the solution, and further followed by adding the compound (IV). When dissolving the compound (II) in the inert solvent while stirring the solution, it is preferable to perform in a state where the solution is cooled in an ice bath.

While the reaction temperature in the process B1 may be adjusted according to the ingredient, the solvent, the base, and the like in the process B1, it is usually −40° C. to 150° C., and preferably −10° C. to 120° C. The reaction temperature in the process B1 may be −10° C. to 50° C., and the reaction under ice-cooling may be carried out.

While the reaction time in the process B1 may be adjusted according to the ingredient, the solvent, the base, and the like in the process B1, it is usually 0.5 hour to 24 hours and preferably 0.5 hour to 2 hours.

The target compound (V) is prepared from the reaction mixture after completing the process B1 according to a method generally used in the field of organic synthesis. For example, when the target compound is an insoluble precipitate, the target compound can be prepared by filtration of the reaction mixture, followed by washing with a solvent. Also, when the target compound is not an insoluble precipitate, the target compound can be prepared by using nonmiscible liquids such as organic solvent and water for separation, separating an organic layer including the target compound, followed by washing with water or the like and drying (extraction).

The prepared target compound may be separated and/or purified as necessary. For such a separating and/or refining method, a method generally used in the field of organic synthesis may be adopted. As such a separating and/or refining method, a method can be mentioned where recrystallization, reprecipitation, chromatography, elution by the eluent, and the like are arbitrarily combined.

2.2.2. Process B2

The process B2 is a process (process of protecting group removal reaction) for preparation of the compound represented by the general formula (VI) from the compound represented by the general formula (V). The process B2 can be carried out according to a constantly carried out method in the field of organic synthesis and the like. The process B2 is generally carried out in an inert solvent. The process B1 may be carried out under the presence of a catalyst. Also, the process B1 may be carried out under the presence of acid. In such a case the compound (V) may be dissolved in an inert solvent, acid may be added under stirring or without stirring. It is to be noted that the process B2 is preferable to be carried out by performing a reflux while adding the acid to the solution.

The inert solvents used for the process B2 are not specifically limited as long as they are inactive against the above-mentioned reaction. As such inert solvents, alcohols such as methanol, ethanol, and isopropanol; ethers such as diethylether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. These inert solvents can be used singly or as a mixture of two or more kinds. Among these inert solvents, ethers such as tetrahydrofuran or alcohols such as ethanol are preferable.

As the catalysts used for the process B2, palladium acetate, triphenylphosphine, palladium-carbon, Raney nickel, platinum oxide, platinum black, rhodium-aluminum-oxide, triphenylphosphine-rhodium chloride, and palladium-barium sulfate can be mentioned. The preferable catalyst among these is palladium acetate or triphenylphosphine.

As the acids used for the process B2, inorganic acid such as hydrochloric acid, hydrobromic acid, sulfuric acid, perchloric acid, and phosphoric acid; Bronsted acid such as organic acid such as acetic acid, formic acid, oxalic acid, methanesulfonic acid, p-toluenesulfonic acid, camphorsulfonic acid, trifluoroacetic acid, and trifluoromethanesulfonic acid; Lewis acid such as zinc chloride, tin tetrachloride, boron trichloride, boron trifluoride, and boron tribromide; or acidic ion-exchange resin can be mentioned. These acids can be used singly or as a mixture of two or more kinds. The preferable acid among these acids is the organic acid such as the formic acid.

While the reaction temperature in the process B2 may be adjusted according to the ingredient, the solvent, the base, and the like in the process B2, it is usually −40° C. to 150° C., and preferably −10° C. to 120° C. The reaction temperature in the process B2 may be 10° C. to 50° C.

While the reaction time in the process B2 may be adjusted according to the ingredient, the solvent, the base, and the like in the process B2, it is usually 0.5 hour to 24 hours and preferably 0.5 hour to 10 hours.

The target compound (VI) is prepared from the reaction mixture after completing the process B2 according to a method generally used in the field of organic synthesis. For example, when the target compound is an insoluble precipitate, the target compound can be prepared by filtration of the reaction mixture, followed by washing with a solvent. Also, when the target compound is not an insoluble precipitate, the target compound can be prepared by using nonmiscible liquids such as organic solvent and water for separation, separating an organic layer including the target compound, followed by washing with water or the like and drying (extraction).

The prepared target compound may be separated and/or purified as necessary. For such a separating and/or refining method, a method generally used in the field of organic synthesis may be adopted. As such a separating and/or refining method, a method can be mentioned where recrystallization, reprecipitation, chromatography, elution by the eluent, and the like are arbitrarily combined.

2.2.3. Process B3

The process B3 is a process for preparation of the compound represented by the general formula (I) by having a condensation reaction between the carbazole derivative represented by the general formula (VI) and the compound represented by the general formula (VII). The process B3 can be carried out according to a constantly carried out method in the field of organic synthesis and the like. The process B3 is generally carried out in an inert solvent. The process B3 may be carried out under the presence of a catalyst. Also, the process B3 may be carried out under the presence of a base. In such a case the compound (VI) may be dissolved in an inert solvent, a base may be added under stirring or without stirring, and then the compound (VII) may be added under stirring or without stirring. It is to be noted that when the W of the compound (VII) represents an aromatic hydrocarbon group, the reaction may be carried out under the presence of the catalyst according to the method reported in "Organic Letters, 2003, Volume 5, P 3799".

The inert solvents used for the process B3 are not specifically limited as long as they are inactive against the above-mentioned reaction. As such inert solvents, alcohols such as methanol, ethanol, and isopropanol; ethers such as diethylether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. Among these inert solvents, amides such as N,N-dimethylformamide or ethers such as dioxane are preferable.

As the bases used for the process B3, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, and LiHMDS can be mentioned. These can be used singly or as a mixture of two or more kinds. Among these bases, metal hydride such as sodium hydride, or alkali metal salt such as potassium carbonate is preferable. As the amount of base in the process B3, 1-5 mol equivalent weight for the compound (VI) can be mentioned.

As the catalysts used for the process B3, metal catalyst such as copper or palladium can be mentioned. Among these, copper catalyst is preferable, and copper iodide, copper bromide, copper chloride, copper dichloride, copper acetate, or copper sulfate can be specifically mentioned. It is to be noted that the process B3 may be carried out in the presence of amino acid such as N,N-dimethylaminoglycine. Use of the metal catalyst and the amino acid is a preferable aspect of the process B3.

While the reaction temperature in the process B3 may be adjusted according to the ingredient, the solvent, the base, and the like in the process B3, it is usually −40° C. to 150° C., and preferably −10° C. to 120° C. The reaction temperature in the process B3 may be 50° C. to 100° C.

While the reaction time in the process B3 may be adjusted according to the ingredient, the solvent, the base, and the like in the process B3, it is usually 0.5 hour to 24 hours and preferably 0.5 hour to 2 hours.

The target compound (V) is prepared from the reaction mixture after completing the process B3 according to a method generally used in the field of organic synthesis. For example, when the target compound is an insoluble precipitate, the target compound can be prepared by filtration of the reaction mixture, followed by washing with a solvent. Also, when the target compound is not an insoluble precipitate, the target compound can be prepared by using nonmiscible liquids such as organic solvent and water for separation, separating an organic layer including the target compound, followed by washing with water or the like and drying (extraction).

The prepared target compound may be separated and/or purified as necessary. For such a separating and/or refining method, a method generally used in the field of organic synthesis may be adopted. As such a separating and/or refining method, a method can be mentioned where recrystallization, reprecipitation, chromatography, elution by the eluent, and the like are arbitrarily combined.

2.3. Method for Preparation of the Compounds of the Present Invention

Method C

Hereinafter, an example of a method (method C) for preparation of the compounds of the present invention represented by the general formula (I) which is different from the above-mentioned method will be described. The method C is a method for preparation of the target compound by converting the substituent group such as a method for preparation of the target compound represented by the general formula (I) by converting the substituent group after producing a compound represented by the general formula (I). The method C is effectively used when the $R^3$ is a hydrogen atom. The method C includes the processes shown in the following process chart.

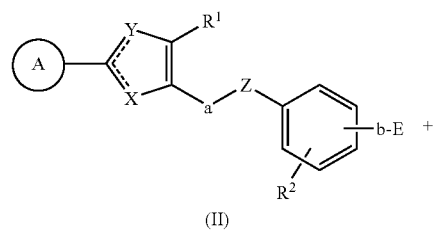

(II)

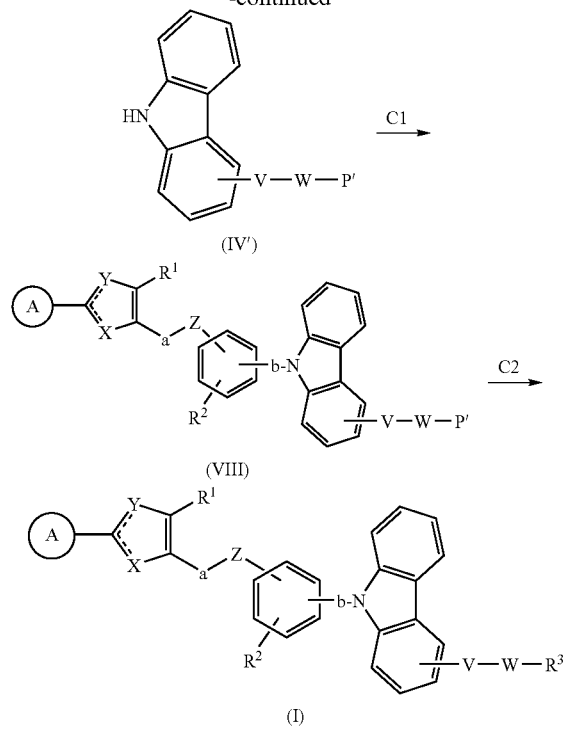

In the above-mentioned formulas, A, V, W, X, Y, Z, b, $R^1$, $R^2$, and $R^3$ respectively represent synonymous definition with those mentioned above. E represents a leaving group. As a specific example of E, a halogen atom can be mentioned, and a chlorine atom or a bromine atom can be mentioned more specifically. P' represents a protecting group. As a specific P', a methyl group, an ethyl group, a butyl group, an allyl group, a benzyl group, a methoxymethyl group, or a tert-butyl group can be mentioned.

2.3.1. Process C1

The process C1 is a process for preparation of the compound represented by the general formula (VIII) from the compound represented by the general formula (II) and the carbazole derivative represented by the general formula (IV'). The process C1 can be carried out according to a constantly carried out method in the field of organic synthesis and the like. The process C1 is generally carried out in an inert solvent. The process C1 may be carried out under the presence of a base. In such a case the compound (II) may be dissolved in an inert solvent, a base may be added under stirring or without stirring, and then the compound (IV') may be added under stirring or without stirring.

The inert solvents used for the process C1 are not specifically limited as long as they are inactive against the above-mentioned reaction. As such inert solvents, alcohols such as methanol, ethanol, and isopropanol; ethers such as diethylether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. These inert solvents can be used singly or as a mixture of two or more kinds. Among these inert solvents, amides are preferable.

As the bases used for the process C1, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, and LiHMDS can be mentioned. Among these bases, metal hydride is preferable. Specifically, when the E is a halogen atom, sodium hydride is preferable among these bases.

A preferable aspect of the process C1 is dissolving the compound (II) in the inert solvent while stirring the solution, followed by adding the base while stirring the solution, and further followed by adding the compound (IV'). When dissolving the compound (II) in the inert solvent while stirring the solution, it is preferable to perform in a state where the solution is cooled in an ice bath.

While the reaction temperature in the process C1 may be adjusted according to the ingredient, the solvent, the base, and the like in the process C1, it is usually −40° C. to 150° C., and preferably −10° C. to 120° C. The reaction temperature in the process C1 may be −10° C. to 50° C., and the reaction under ice-cooling may be carried out.

While the reaction time in the process C1 may be adjusted according to the ingredient, the solvent, the base, and the like in the process C1, it is usually 0.5 hour to 24 hours and preferably 0.5 hour to 2 hours.

The target compound (VIII) is prepared from the reaction mixture after completing the process C1 according to a method generally used in the field of organic synthesis. For example, when the target compound is an insoluble precipitate, the target compound can be prepared by filtration of the reaction mixture, followed by washing with a solvent. Also, when the target compound is not an insoluble precipitate, the target compound can be prepared by using nonmiscible liquids such as organic solvent and water for separation, separating an organic layer including the target compound, followed by washing with water or the like and drying (extraction).

The prepared target compound may be separated and/or purified as necessary. For such a separating and/or refining method, a method generally used in the field of organic synthesis may be adopted. As such a separating and/or refining method, a method can be mentioned where recrystallization, reprecipitation, chromatography, elution by the eluent, and the like are arbitrarily combined.

2.3.2. Process C2

The process C2 is a process for preparation of the carbazole derivative represented by the general formula (I) by deprotecting the compound represented by the general formula (VIII). Therefore, the method C is effectively used especially when the $R^3$ is a hydrogen atom. However, the method C is not limited to such a case. The process C2 can be carried out according to a constantly carried out method in the field of organic synthesis and the like. The process C2 is generally carried out in an inert solvent. The process C2 may be carried out under the presence of a base.

The inert solvents used for the process C2 are not specifically limited as long as they are inactive against the above-mentioned reaction. As such inert solvents, alcohols such as methanol, ethanol, and isopropanol; ethers such as diethylether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. These inert solvents can be used singly or as a mixture of two or more kinds. Among these inert solvents, ethers such as tetrahydrofuran or alcohols such as ethanol are preferable.

As the catalysts used for the process C2, palladium acetate, triphenylphosphine, palladium-carbon, Raney nickel, platinum oxide, platinum black, rhodium-aluminum-oxide, triphenylphosphine-rhodium chloride, and palladium-barium sulfate can be mentioned. The preferable catalyst among these is palladium acetate or triphenylphosphine.

As the bases used for the process C2, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, and LiHMDS can be mentioned. These can be used singly or as a mixture of two or more kinds. Among these bases, metal hydride such as sodium hydride, or alkali metal salt such as potassium carbonate is preferable. As the amount of the base in the process C2, 1-5 mol equivalent weight for the compound (VI) can be mentioned.

While the reaction temperature in the process C2 may be adjusted according to the ingredient, the solvent, the base, and the like in the process C2, it is usually −40° C. to 150° C., and preferably −10° C. to 120° C. The reaction temperature in the process C2 may be 10° C. to 50° C.

While the reaction time in the process C2 may be adjusted according to the ingredient, the solvent, the base, and the like in the process C2, it is usually 0.5 hour to 24 hours and preferably 0.5 hour to 10 hours.

The target compound (V) is prepared from the reaction mixture after completing the process C2 according to a method generally used in the field of the organic synthesis. For example, when the target compound is an insoluble precipitate, the target compound can be prepared by filtration of the reaction mixture, followed by washing with a solvent. Also, when the target compound is not an insoluble precipitate, the target compound can be prepared by using nonmiscible liquids such as organic solvent and water for separation, separating an organic layer including the target compound, followed by washing with water or the like and drying (extraction).

The prepared target compound may be separated and/or purified as necessary. For such a separating and/or refining method, a method generally used in the field of organic synthesis may be adopted. As such a separating and/or refining method, a method can be mentioned where recrystallization, reprecipitation, chromatography, elution by the eluent, and the like are arbitrarily combined.

2.4. Method for Preparation of the Compounds of the Present Invention

Method D

Hereinafter, an example of a method (method D) for preparation of the compounds of the present invention represented by the general formula (I) which is different from the above-mentioned method will be described. The method D is a method for preparation of the compounds represented by the general formula (I), followed by preparation of the salt thereof. According to this method, after the compound represented by the general formula (I) is dissolved in the inert solvent, the salt can be prepared by making alkali metal hydroxide such as sodium hydroxide and potassium hydroxide or organic acid salt such as sodium 2-ethyl hexanoate react therewith. As the inert solvents in the method D, alcohol such as ethanol and 2-propanol, ester such as ethyl acetate and isobutyl acetate, or ketone such as acetone and methyl isobutyl ketone can be mentioned. As the concentration of the hydroxide used, 0.1 N to 10 N can be mentioned, while it may be 0.5 N to 5 N. The hydroxide, or the organic acid salt used is added to the compound (I), for example, by 1 equivalent weight to 10 equivalent weight. The reaction temperature in the method D is usually −40° C. to 150° C., and preferably −10° C. to 120° C. The reaction time in the method D is usually 0.1 hour to 24 hours and preferably 0.5 hour to 2 hours.

2.5. Method for Preparation of the Compound (II)

The compound represented by the general formula (II) can be prepared according to the method described, for example, in WO01/38325 and the method shown below (method E).

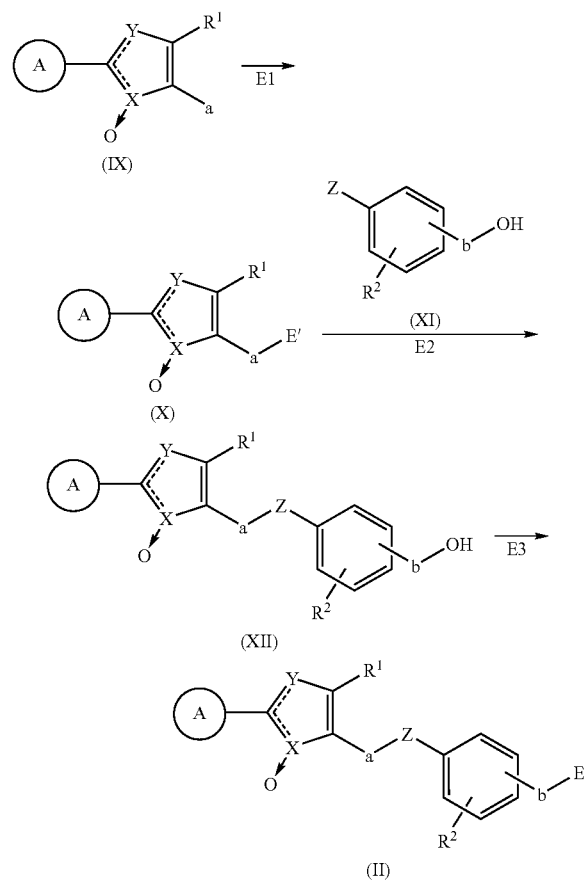

In the above-mentioned formulas, A, W, X, Y, Z, b, $R^1$, $R^2$, and $R^3$ respectively represent synonymous definition with those mentioned above. As an example of E or E', a hydroxyl group, a halogen atom, or —$OSO_2R^7$ ($R^7$ is a methyl group, a trifluoromethyl group, a phenyl group, a tolyl group, or a nitrophenyl group) can be mentioned. As a more specific E or E', a chlorine atom or a bromine atom can be mentioned.

2.5.1. Process E1

The process E1 is a process for preparation of a compound represented by the general formula (X) by halogenating an end group a of the compound represented by the general formula (IX). The process E1 can be carried out according to a constantly carried out method in the field of organic synthesis and the like. The process E1 is generally carried out in an inert solvent. In the process E1, the compound represented by the general formula (X) can be prepared by dissolving the compound represented by the general formula (IX) in solvent such as methylene chloride or chloroform, and adding chloride such as NaClO, $SOCl_2$ (thionyl chloride), $PCl_3$, or $POCl_3$ (phosphorous oxychloride) dropwise into the solution. As the solvent, chloroform can be mentioned, and as a chloride added dropwise, phosphorous oxychloride can be mentioned.

The compound (IX) can be prepared by purchasing commercialized products. Among the compounds (IX), specifically when the five-membered ring is an oxazole ring, it is preferable to prepare the compound (IX') by the following E1' process.

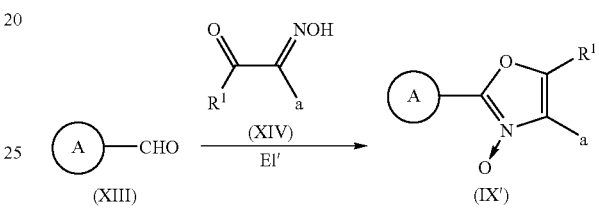

The E1' process is a process for the preparation of the compound (IX') whose five-membered ring is an oxazole ring from the compound (XIII) and the compound (XIV). The E1' process can be carried out by dissolving the compound (XIII) and compound (XIV) in acids, blowing in hydrochloride gas to be saturated, and further stirring. By the E1' process, the compound (IX') can be prepared not only when the A ring is a benzene ring or a naphthyl ring, but also when it is, for example, various aromatic hydrocarbon rings or aromatic heterocycles such as a furan ring, a thiophen ring, and a pyridine ring.

As the acids used for the E1' process, inorganic acid such as hydrochloric acid, hydrobromic acid, sulfuric acid, perchloric acid, and phosphoric acid; Bronsted acid such as organic acid such as acetic acid, formic acid, oxalic acid, methanesulfonic acid, p-toluenesulfonic acid, camphorsulfonic acid, trifluoro acetic acid, and trifluoro methanesulfonic acid; Lewis acid such as zinc chloride, tin tetrachloride, boron trichloride, boron trifluoride, and boron tribromide; or acidic ion-exchange resin can be mentioned. These acids can be used singly or as a mixture of two or more kinds. The preferable acid among these acids is the organic acid such as the acetic acid.

While the reaction temperature in the E1' process may be adjusted according to the ingredient, the solvent, the base, and the like in the E1' process, it is usually −40° C. to 150° C., and preferably −10° C. to 10° C. For example, the temperature at the time of blowing in the hydrochloride gas may be e.g. −10° C. to 20° C., and the temperature at the time of stirring may be 20° C. to 40° C. While the reaction time in the E1' process may be adjusted according to the ingredient, the solvent, the base, and the like in the E1' process, it is usually 0.5 hour to 24 hours and preferably 0.5 hour to 10 hours.

2.5.2. Process E2

The process E2 is a process for preparation of the compound represented by the general formula (XII) from the compound represented by the general formula (X) and the carbazole derivative represented by the general formula (XI). The process E2 can be carried out according to a constantly carried out method in the field of organic synthesis and the like. The process E2 is generally carried out in an inert solvent. The process E2 may be carried out under the presence of a base. In such a case the compound (II) may be dissolved in an inert solvent, a base may be added under stirring or without stirring, and then the compound (IV) may be added under stirring or without stirring.

The inert solvents used for the process E2 are not specifically limited as long as they are inactive against the above-mentioned reaction. As such inert solvents, alcohols such as methanol, ethanol, and isopropanol; ethers such as diethyl-ether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. Among these inert solvents, amides such as N,N-dimethylformamide or ethers such as dioxane are preferable.

As the bases used for the process E2, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, and LiHMDS can be mentioned. These bases can be used singly or as a mixture of two or more kinds. Among these bases, alkali metal such as sodium hydroxide, and potassium hydroxide, metal hydride such as sodium hydride, or alkali metal salt such as potassium carbonate is preferable. As the amount of base in the process E2, 1-5 mol equivalent weight for the compound (X) can be mentioned.

While the reaction temperature in the process E2 may be adjusted according to the ingredient, the solvent, the base, and the like in the process E2, it is usually −40° C. to 150° C., and preferably −10° C. to 120° C. The reaction temperature in the process E2 may be 10° C. to 50° C.

While the reaction time in the process E2 may be adjusted according to the ingredient, the solvent, the base, and the like in the process E2, it is usually 0.5 hour to 24 hours and preferably 0.5 hour to 10 hours.

2.5.3. Process E3

The process E3 is a process (process of halogenating hydroxyl group) for preparation of the compound represented by the general formula (II) from the compound represented by the general formula (XII). The process E3 can be carried out according to a constantly carried out method in the field of organic synthesis and the like. In the process E3, the compound represented by the general formula (X) can be prepared by dissolving the compound represented by the general formula (IX) in solvent such as methylene chloride or chloroform, and adding chloride such as NaClO, SOCl$_2$ (thionyl chloride), PCl$_3$, or POCl$_3$ (phosphorous oxychloride) dropwise into the solution. As the solvent, methylene chloride can be mentioned, and as a chloride added dropwise, thionyl chloride can be mentioned.

2.6. Method for Preparation of the Compound (III) and Compound (IV)

The compound represented by the general formula (III), and the compound represented by the general formula (IV) or general formula (IV') can be prepared according to the method described, for example, in DE2243574 and the method shown below (method F).

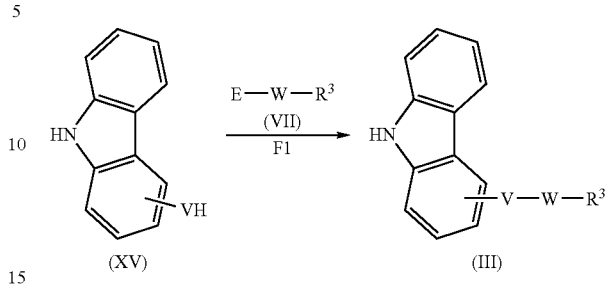

In the above-mentioned formula, V, W, and R$^3$ respectively represent synonymous definition with those mentioned above. As an example of E, a hydroxyl group, a halogen atom, or —OSO$_2$R$^7$ (R$^7$ is a methyl group, a trifluoromethyl group, a phenyl group, a tolyl group, or a nitrophenyl group) can be mentioned. As a more specific E, a chlorine atom or a bromine atom can be mentioned.

2.6.1. Process F1

The process F1 is a process for preparation of the compound represented by the general formula (III) from the compound represented by the general formula (XV) and the carbazole derivative represented by the general formula (VII). The process F1 can be carried out according to a constantly carried out method in the field of organic synthesis and the like. The process F1 is generally carried out in an inert solvent. The process F1 may be carried out under the presence of a base. In such a case the compound (XV) may be dissolved in an inert solvent, a base may be added under stirring or without stirring, and then the compound (VII) may be added under stirring or without stirring.

The inert solvents used for the process F1 are not specifically limited as long as they are inactive against the above-mentioned reaction. As such inert solvents, alcohols such as methanol, ethanol, and isopropanol; ethers such as diethyl-ether, tetrahydrofuran, and dioxane; halogenated hydrocarbons such as chloroform, and dichloromethane; aromatic hydrocarbons such as toluene, and xylene; amides such as N,N-dimethylformamide, N,N-dimethylacetamide, and N-methylpyrrolidone; sulfoxides such as dimethylsulfoxide; or water can be mentioned. These inert solvents can be used singly or as a mixture of two or more kinds. Among these inert solvents, amides are preferable.

As the bases used for the process F1, alkali metal hydroxide such as sodium hydroxide, and potassium hydroxide; alkali metal salt such as sodium carbonate, potassium carbonate, and cesium carbonate; metal hydride such as sodium hydride, and potassium hydride; metal alkoxide such as sodium methoxide, sodium ethoxide, and potassium tert-butoxide; or organic alkali metal salt such as LDA, NaHMDS, KHMDS, and LiHMDS can be mentioned. These bases can be used singly or as a mixture of two or more kinds. Among these bases, alkali metal hydroxide such as sodium hydroxide and potassium hydroxide, metal hydride such as sodium hydride, or alkali metal salt such as potassium carbonate is preferable. As the amount of the base in the process F1, 1-5 mol equivalent weight for the compound (XV) can be mentioned.

While the reaction temperature in the process F1 may be adjusted according to the ingredient, the solvent, the base, and the like in the process F1, it is usually −40° C. to 150° C., and preferably −10° C. to 120° C. The reaction temperature in the process F1 may be 50° C. to 100° C.

While the reaction time in the process F1 may be adjusted according to the ingredient, the solvent, the base, and the like in the process F1, it is usually 0.5 hour to 24 hours and preferably 3 hour to 10 hours.

3. Medicines and the Like

The compounds of the present invention are new substances for which various applications are expected. Moreover, the compounds of the present invention, as exemplified by the examples which will be described later, have excellent PPARγ inhibitory effect or PPARγ partial inhibitory effect, as well as PPARα agonistic effect, function as antagonists or partial antagonists of the PPARγ, and also function as agonists of the PPARα. The compounds of the present invention have an excellent adipose tissue weight reducing effect, hypoglycemic effect and hypolipidemic effect. Also, the compounds of the present invention are effective in suppression of body weight increase, improvement of insulin resistance, suppression of glucose tolerance reduction, suppression of insulin sensitivity reduction, and the like. Therefore, the compounds of the present invention are useful as preventive agents or therapeutic agents for fatty liver, obesity, lipid metabolism abnormality, visceral adiposity, diabetes, hyperlipemia, impaired glucose tolerance, hypertension, non-alcoholic fatty liver disease, non-alcoholic steatohepatitis, and the like. The compounds of the present invention are useful as preventive agents or therapeutic agents especially for disorders involving the PPAR such as fatty liver. The compounds of the present invention that function as the antagonist or partial antagonist of the PPARγ are useful as preventive agents or therapeutic agents especially for fatty liver, obesity, lipid metabolism abnormality, visceral adiposity, diabetes, or impaired glucose tolerance. Also, the compounds of the present invention that function as agonists of the PPARα are useful as preventive agents or therapeutic agents especially for hyperlipemia or hypertension.

The compounds of the present invention are useful as preventive agents or therapeutic agents for a series of clinical conditions based on insulin resistance, namely the metabolic syndrome. The "metabolic syndrome" represents a state where a series of clinical conditions such as type II diabetes based on insulin resistance, hyperlipemia, visceral obesity, fatty liver, and the like coexist, and is also called a syndrome X, insulin resistant syndrome, visceral obesity syndrome, or multiple risk factor syndrome.

It is known that partial agonists and partial antagonists in addition to agonists and antagonists are generally present in the nuclear receptor group. These are collectively called "modulators". The compounds of the present invention, as exemplified by the examples which will be described later, function as antagonists or partial antagonists of the PPARγ, and also function as agonists of the PPARα, so that the present invention can also provide PPAR modulators, especially PPARγ modulators or PPARα modulators.

Having the above-mentioned effects, the compounds of the present invention can be used in prevention or therapy of fatty liver, obesity, lipid metabolism abnormality, visceral adiposity, diabetes, hyperlipemia, impaired glucose tolerance, hypertension, non-alcoholic fatty liver disease, or non-alcoholic steatohepatitis. Moreover, the compounds of the present invention can be used for the preparation of preventive agents or therapeutic agents for fatty liver, obesity, lipid metabolism abnormality, visceral adiposity, diabetes, hyperlipemia, impaired glucose tolerance, hypertension, non-alcoholic fatty liver disease, or non-alcoholic steatohepatitis.

Moreover, medical compositions (hereinafter, occasionally referred to as "medical compositions of the present invention") including the compounds of the present invention and a pharmaceutically acceptable carrier or the like are useful as preventive agents or therapeutic agents for fatty liver, obesity, lipid metabolism abnormality, visceral adiposity, diabetes, hyperlipemia, impaired glucose tolerance, hypertension, non-alcoholic fatty liver disease, non-alcoholic steatohepatitis, and the like.

Namely, by the present specification, usage of the compounds of the present invention for preparation of medical compositions can be provided, and to describe more specifically, usage of the medical compositions for prevention and therapy of fatty liver, obesity, lipid metabolism abnormality, visceral adiposity, diabetes, hyperlipemia, impaired glucose tolerance, hypertension, non-alcoholic fatty liver disease, or non-alcoholic steatohepatitis can be provided. Also, by the present specification, usage of the compounds of the present invention for preventing or treating fatty liver, obesity, lipid metabolism abnormality, visceral adiposity, diabetes, hyperlipemia, impaired glucose tolerance, hypertension, non-alcoholic fatty liver disease, or non-alcoholic steatohepatitis can be provided.

When the compounds of the present invention are used as the above-mentioned preventive agents or therapeutic agents, the compounds may be administered per se, or mixed with a pharmaceutically acceptable carrier or the like to be administered. Such preventive agents or therapeutic agents can be prepared by publicly known methods. As agents using the compounds of the present invention, oral agents such as tablets, capsules, granules, powder medicines, and syrups; and parenteral agents such as injectable solutions and suppositories can be mentioned. These agents can be administered orally or parenterally.

As a pharmaceutically acceptable carrier, one arbitrarily selected from vehicle, diluent, a lubricant, binder, disintegrant, stabilizer, and flavoring agent can be mentioned.

As the vehicle, for example, organic vehicle such as sugar derivative such as lactose, sucrose, glucose, mannitol, and sorbitol; starch derivative such as cornstarch, potato starch, alpha-starch, and dextrin; cellulose derivative such as crystalline cellulose; gum arabic; dextran; and organic vehicle such as pullulan: as well as inorganic vehicle such as silicate derivative such as light anhydrous silicic acid, synthetic aluminum silicate, calcium silicate, and magnesium aluminometasilicate; phosphoric acid salt such as calcium hydrogen phosphate; carbonate such as calcium carbonate; and sulfate salt such as calcium sulfate can be mentioned.

As the lubricant, for example, stearate metal salt such as stearate, calcium stearate, and magnesium stearate; talc; colloid silica; waxes such as magnesium aluminum silicate, and whale wax; boracic acid; adipic acid; sulfate salt such as sodium sulfate; glycol; fumaric acid; sodium benzoate; DL leucine; fatty acid sodium salt; lauryl sulfate salt such as sodium lauryl sulfate, and sodium lauryl sulfate magnesium; silicates such as silicic anhydride, and silicate hydrate; and the above-mentioned starch derivative can be mentioned.

As the binder, for example, hydroxypropylcellulose, hydroxypropyl methylcellulose, polyvinylpyrrolidone, macrogol, and compounds same as those of the above-mentioned vehicle can be mentioned.

As the disintegrant, for example, cellulose derivative such as hydroxypropylcellulose of low substitution degree, carboxymethylcellulose, carboxymethylcellulose calcium, and internally bridged carboxymethylcellulose sodium; chemically-modified starches and celluloses such as carboxymethylstarch, sodium starch glycolate, and bridged polyvinylpyrrolidone can be mentioned.

As the stabilizer, for example, p-hydroxybenzoic esters such as methylparaben, and propylparaben; alcohols such as chlorobutanol, benzyl alcohol, and phenylethyl alcohol; benzalkonium chloride; phenols such as phenol, and cresol; thimerosal; dehydroacetic acid; and sorbic acid can be mentioned. As the flavoring agent, for example, sweetener, acidulant, aroma chemical, and the like can be mentioned. As the diluent, sterile water, sterile organic solvent, aqueous starch, or the like can be mentioned.

The agents of the present invention can be prepared by using the compounds of the present invention or the medical compositions of the present invention according to methods that are publicly known. Tablets can be prepared, for example, by tableting the medical composition in which the compounds of the present invention and a publicly known carrier are mixed with a tableting machine. Capsules and suppositories can be prepared, for example, by enclosing the compounds of the present invention or the medical compositions of the present invention in carriers shaped as capsules and the like. Syrups can be prepared, for example, by dissolving the compounds of the present invention or the medical compositions of the present invention in liquid solvent such as syrup. Powder medicines such as granules can be prepared by powderizing the compounds of the present invention or the medical compositions of the present invention by publicly known means.

Dosage of the compounds of the present invention may be appropriately adjusted according to symptom, age, gender, administration method, and the like. For example, in case of oral administration, lower limit of 0.001 mg/kg weight (preferably 0.01 mg/kg weight) and upper limit of 500 mg/kg weight (preferably 50 mg/kg weight) may be administered at a time. Also, in case of intravenous administration, lower limit of 0.005 mg/kg weight (preferably 0.05 mg/kg weight) and upper limit of 50 mg/kg weight (preferably 5 mg/kg weight) may be administered at a time. As for number of doses, for example, one dose to several doses per day may be administered according to symptoms.

Pharmacologic effects such as the PPARγ inhibitory activity of the compounds of the present invention can be measured by using the pharmacologic testing method as described in the examples of tests that will be described later or methods pursuant thereto.

While the present invention will be described below in more detail by using examples, the present invention is not limited to those examples.

Reference 1

Preparation of 4-((4-(chloromethyl)-2-methoxyphenoxy)methyl)-5-methyl-2-phenyloxazole

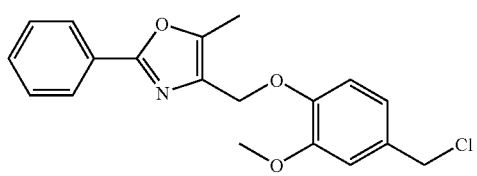

Reference 1(a)

Preparation of 4,5-dimethyl-2-phenyloxazole N-oxide

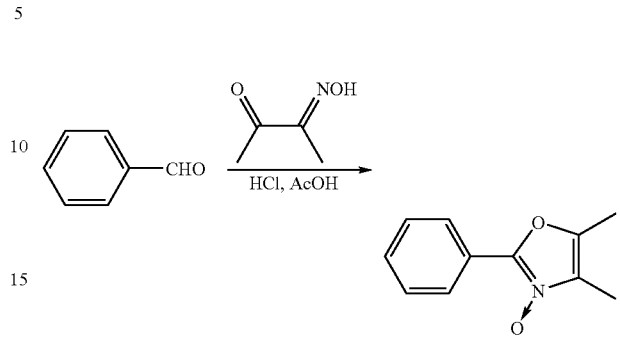

500 g of benzaldehyde and 476 g of diacetylmonoxime were suspended in 1 L of acetic acid and cooled in an ice bath. At internal temperature of 7° C., hydrochloride gas is slowly blown in to be saturated. At room temperature, the mixture was stirred overnight. The reaction mixture was poured into 1.5 kg of ice, and neutralized with 25% sodium hydroxide solution. The crystalline precipitate was isolated by filtration and washed with 1 L of water and 1 L of diisopropylether. The obtained crystals were dissolved in 3 L of chloroform and insoluble matter was filtered off. The filtrate was dried with 200 g of anhydrous sodium sulfate, filtered, and the filtrate was concentrated in vacuo. 3 L of IPE was added to the residue to be crystallized, the crystal was isolated by filtration, dried under reduced pressure at 50° C. for 1 hour, and 440 g of the subject compound was prepared.

$^1$H-NMR (400 MHz, CDCl$_3$) δ ppm: 2.22 (3H, d) 2.36 (3H, d) 7.41-7.52 (3H, m) 8.44-8.49 (2H, m)

Reference 1(b)

Preparation of 4-(chloromethyl)-5-methyl-2-phenyloxazole

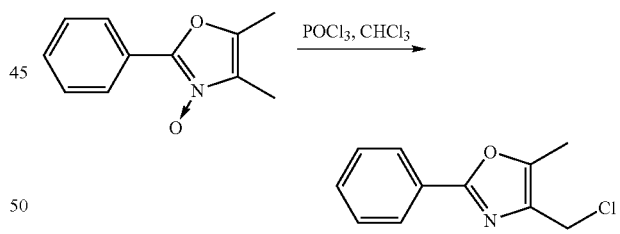

383 g of phosphorous oxychloride was slowly added dropwise into chloroform (2 L) solution of 430 g of 4,5-dimethyl-2-phenyloxazole N-oxide. After the dropwise addition, the solution was stirred for 2 hours at room temperature. The reaction mixture was concentrated in vacuo, and 2 L of ethyl acetate was added to the residue. The foregoing ethyl acetate solution was added to mixed solution of 2 L of ice water and 1.2 L of 25% sodium hydroxide solution under stirring. The liquid was separated, and the ethyl acetate layer was washed with 1 L of brine, and dried with 300 g of anhydrous sodium sulfate. After filtration in vacuo, the filtrate was concentrated. Ethanol:n-hexane=1:10 (1.1 L) was added to the crystalline residue, and then filtered off. The crystal was dried under reduced pressure at 40° C. for 1 hour, 321 g of the subject compound was prepared.

¹H-NMR (400 MHz, CDCl₃) δ ppm: 2.43 (3H, s) 4.56 (2H, s) 7.42-7.46 (3H, m) 7.98-8.02 (2H, m)

Reference 1(c)

Preparation of (4-(5-methyl-2-phenyloxazole-4-yl)methoxy)-3-methoxyphenyl)methanol

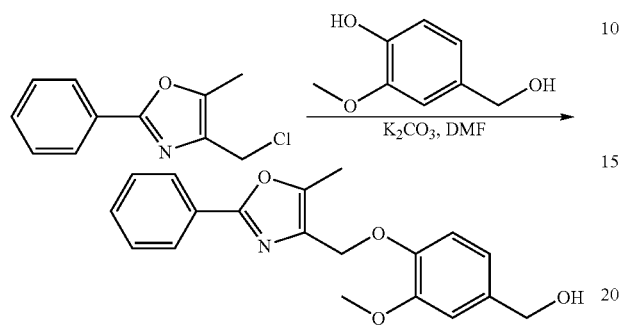

311 g of 4-(chloromethyl)-5-methyl-2-phenyloxazole, 277 g of vanillyl alcohol, and 415 g of powdered potassium carbonate were added to 1 L of N,N-dimethylformamide and stirred at 90° C. for 1 hour. The reaction mixture was cooled to room temperature, and 2.5 L of ice water was added to the reaction mixture under stirring. The precipitate crystal was filtered off, and washed with 1 L of water and 0.5 L of IPE. The obtained crystal was dissolved by heating into 2 L of isopropyl alcohol. A part of the insoluble matter was filtered and the filtrate was stirred overnight. The precipitate crystal was isolated by filtration and washed with 0.5 L of isopropyl alcohol. The obtained crystal was dried under reduced pressure and 325 g of the subject compound was prepared.

¹H-NMR (400 MHz, CDCl₃) δ ppm: 1.77 (1H, d) 2.41 (3H, s) 3.88 (3H, s) 4.63 (2H, d) 5.05 (2H, s) 6.87 (1H, dd) 6.95 (1H, d) 7.02 (1H, d) 7.40-7.47 (3H, m) 7.98-8.03 (2H, m)

Reference 1(d)

Preparation of 4-((4-(chloromethyl)-2-methoxyphenoxy)methyl)-5-methyl-2-phenyloxazole

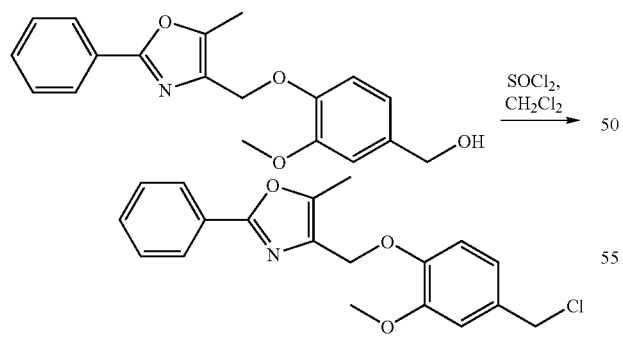

315 g of (4-(5-methyl-2-phenyloxazole-4-yl)methoxy)-3-methoxyphenyl)methanol was suspended in 1.5 L of methylene chloride, and thionyl chloride was added thereto dropwise while being cooled in an ice bath. After the dropwise addition thereto, the reaction mixture was stirred at room temperature for 1 hour. The reaction mixture was poured into mixture of 1.8 L of 2 N sodium hydroxide solution and 1.8 Kg of ice, stirred for 15 minutes, and separated. The organic layer was washed with 1 L of brine, and dried over anhydrous sodium sulfate. After filtration, the filtrate was concentrated in vacuo. Ethanol:hexane=1:10(1.65 L) was added to the crystalline residue and isolated by filtration. The crystal was dried under reduced pressure and 307 g of the subject compound was prepared.

¹H-NMR (400 MHz, DMSO-d₆) δ ppm: 2.44 (3H, s) 3.76 (3H, s) 4.72 (2H, d) 4.99 (2H, s) 6.99 (1H, dd) 7.07 (1H, d) 7.11 (1H, d) 7.48-7.57 (3H, m) 7.91-7.98 (2H, m)

Reference 2

Preparation of 4-((4-(chloromethyl)-2-methoxyphenoxy)methyl)-2-(furan-2-yl)-5-methyloxazole

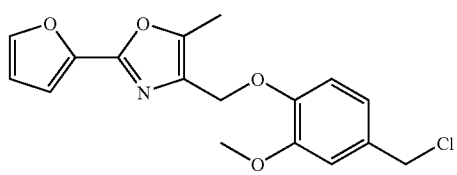

The subject compound was prepared by performing the same operation as those of the references 1(a) to 1(d) by using furfural instead of benzaldehyde in the reference 1(a).

¹H-NMR (400 MHz, DMSO-d₆) δ ppm: 2.41 (3H, s) 3.76 (3H, s) 4.72 (2H, d) 4.97 (2H, s) 6.71 (1H, dd) 6.98 (1H, dd) 6.71 (1H, dd) 6.98 (1H, dd) 7.06 (1H, d) 7.08 (1H, d) 7.11 (1H, dd) 7.91 (1H, dd)

Reference 3

Preparation of 4-((4-(chloromethyl)-2-methoxyphenoxy)methyl)-2-(thiophene-2-yl)-5-methyloxazole

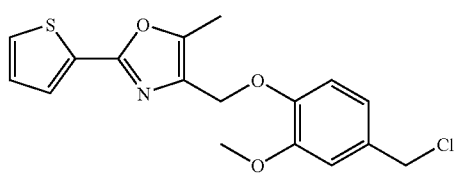

The subject compound was prepared by performing the same operation as those of the references 1(a) to 1(d) by using 2-thiophenealdehyde instead of benzaldehyde in the reference 1(a).

¹H-NMR (400 MHz, DMSO-d₆) δ ppm: 2.41 (3H, s) 3.76 (3H, s) 4.72 (2H, d) 4.95 (2H, s) 6.98 (1H, dd) 7.07 (1H, m) 7.08 (1H, dd) 7.21 (1H, dd) 7.66 (1H, dd) 7.77 (1H, dd)

Reference 4

Preparation of 4-((4-(chloromethyl)-2-methoxyphenoxy)methyl)-2-(pyridine-4-yl)-5 methyloxazole

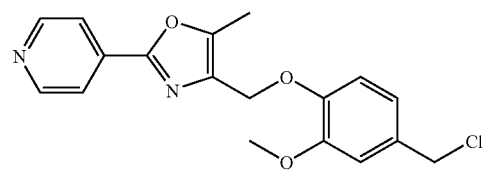

The subject compound was prepared by performing the same operation as those of the references 1(a) to 1(d) by using 4-pyridinecarboxaldehyde instead of benzaldehyde in the reference 1(a).

$^1$H-NMR (400 MHz, CDCl$_3$) δ ppm: 2.45 (3H, s) 3.89 (3H, s) 4.57 (2H, d) 5.07 (2H, s) 6.92 (1H, dd) 6.94 (1H, d) 7.01 (1H, d) 7.85 (2H, dd) 8.72 (2H, dd)

Reference 5

Preparation of 4-((4-(chloromethyl)-2-methoxyphenoxy)methyl)-5-methyl-2-phenylthiazole

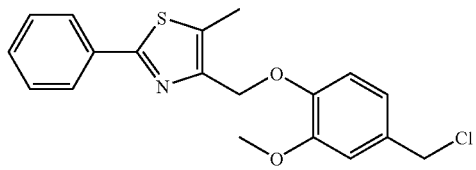

The subject compound was prepared by performing the same operation as those of the references 1(c) to 1(d) by using 4-(chloromethyl)-5-methyl-2-phenylthiazole prepared by the method described in Tetrahedron Letters (2004, Volume 45, P 69) instead of 4-(chloromethyl)-5-methyl-2-phenyloxazole in the reference 1(c).

$^1$H-NMR (400 MHz, DMSO-d$_6$) δ ppm: 2.50 (3H, s) 3.76 (3H, s) 4.72 (2H, d) 5.13 (2H, s) 6.99 (1H, dd) 7.06 (1H, d) 7.14 (1H, d) 7.45-7.52 (3H, m) 7.85-7.91 (2H, m)

Reference 6

Preparation of 5-((4-(chloromethyl)-2-methoxyphenoxy)methyl)-4-methyl-2-phenylthiazole

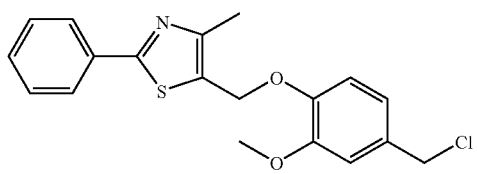

The subject compound was prepared by performing the same operation as those of the references 1(c) to 1(d) by using commercially available 5-(bromomethyl)-4-methyl-2-phenylthiazole instead of 4-(chloromethyl)-5-methyl-2-phenyloxazole in the reference 1(c).

$^1$H-NMR (400 MHz, DMSO-d$_6$) δ ppm: 2.50 (3H, s) 3.76 (3H, s) 4.72 (2H, d) 5.13 (2H, s) 6.99 (1H, dd) 7.06 (1H, d) 7.14 (1H, d) 7.45-7.52 (3H, m) 7.85-7.91 (2H, m)

Reference 7

Preparation of 4-((4-(chloromethyl)phenoxy)methyl)-5-methyl-2-phenylthiazole

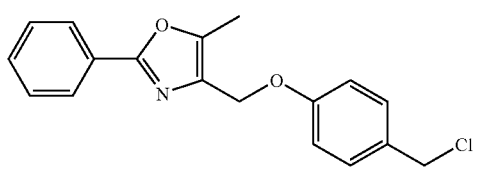

The subject compound was prepared by performing the same operation as those of the references 1(c) to 1(d) by using 4-hydroxybenzyl alcohol instead of vanillyl alcohol in the reference 1(c).

$^1$H-NMR (400 MHz, DMSO-d$_6$) δ ppm: 2.45 (3H, s) 4.73 (2H, d) 5.02 (2H, s) 7.05 (2H, d) 7.39 (2H, d) 7.50-7.56 (3H, m) 7.92-7.97 (2H, m)

Reference 8

Preparation of 4-((5-(chloromethyl)-2-methoxyphenoxy)methyl)-2-(furan-2-yl)-5-methyloxazole

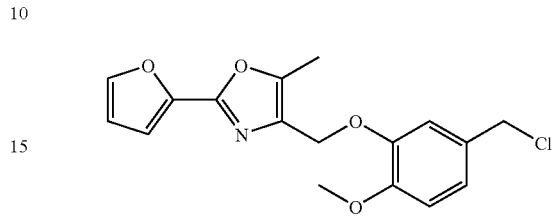

The subject compound was prepared by performing the same operation as those of the references 1(a) to 1(d) by using furfural instead of benzaldehyde in the reference 1(a), and by using 3-hydroxy-4-methoxybenzyl alcohol instead of vanillyl alcohol used in the reference 1(c).

$^1$H-NMR (400 MHz, DMSO-d$_6$) δ ppm: 2.42 (3H, s) 3.76 (3H, s) 4.71 (2H, d) 4.96 (2H, s) 6.71 (1H, dd) 6.98 (1H, dd) 6.71 (1H, dd) 6.96 (1H, dd) 7.02 (1H, dd) 7.11 (1H, d) 7.18 (1H, d) 7.91 (1H, dd)

Reference 9

Preparation of 4-(allyloxy)-9H-carbazole

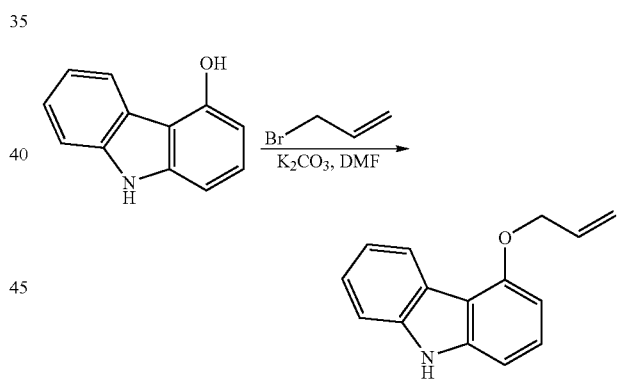

138 g of potassium carbonate was added to N,N-dimethylformamide (500 mL) solution of 121.9 g of 4-hydroxycarbazole. Under stirring, 88.6 g of allyl bromide was added thereto and the reaction mixture was stirred at 80° C. for 5 hours. The reaction mixture was allowed to cool, 3.5 L of water was added thereto, and extracted twice with 1 L of ethyl acetate. The combined organic layer was washed with 1 L of brine, and dried over anhydrous sodium sulfate. After filtration, the filtrate was concentrated in vacuo. The residue was purified by NH silica gel chromatography (ethyl acetate:n-hexane=1:1), and 129 g of the subject compound was prepared.

$^1$H-NMR (400 MHz, CDCl$_3$) δ ppm: 4.79 (2H, d) 5.35 (1H, dd) 5.56 (1H, dd) 6.18-6.28 (1H, m) 6.66 (1H, d) 7.01 (1H, d) 7.21-7.26 (1H, m) 7.30 (1H, dd) 7.34-7.41 (2H, m) 7.97 (1H, br) 8.35 (1H, d)

Reference 10

Preparation of ethyl (R)-2-bromobutyrate

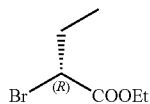

Reference 10(a)

Preparation of (R)-2-bromobutyric acid

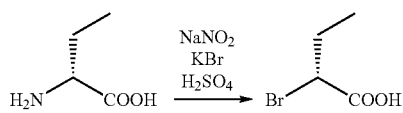

25 g of D-2-aminobutyric acid and 105 g of KBr were dissolved in 1.25M sulfuric acid solution (588 mL) at room temperature. The solution was cooled to internal temperature of approximately −5° C., and the solution of 25.7 g of sodium nitrite was added thereto dropwise at internal temperature of approximately −5° C. to −3° C. for 1 hour. The solution was stirred at internal temperature of approximately −5° C. for 1.5 hour. The reaction mixture was extracted with ethyl acetate, washed 3 times with water, washed with brine, and dried over anhydrous sodium sulfate. After filtration, the filtrate was concentrated in vacuo, the residual oil was distilled under reduced pressure, and 17.6 g of the subject compound was prepared as colorless oil. bp: 100° C. (9 Torr)

$^1$H-NMR (400 MHz, CDCl$_3$) δ ppm: 1.07 (3H, t) 2.04 (1H, dq) 2.13 (1H, dq) 4.20 (1H, t)

Reference 10(b)

Preparation of ethyl (R)-2-bromobutyrate

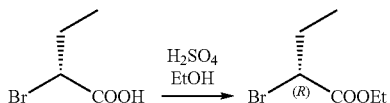

0.45 mL of sulfuric acid was added to ethanol (70 mL) solution of 7.0 g of (R)-2-bromobutyric acid at room temperature, and refluxed for 3 hours. The reaction mixture was cooled to room temperature, and poured into ice water (140 mL). The solution was extracted 3 times with ethyl acetate. The combined extract was sequentially washed with saturated sodium hydrogen carbonate solution and brine, and dried over anhydrous sodium sulfate. After filtration, the filtrate was concentrated in vacuo, and 7.47 g of the subject compound was prepared as colorless oil. Optical purity 96% ee (HPLC)
Column: CHIRALCEL OB-H 0.46×25 cm (Daicel Chemical Industries, Ltd.)
Eluate: n-hexane:2-propanol=90:10
Flow rate: 0.5 mL/min
Temperature: 35° C.
Detection: UV 230 nm $^1$H-NMR (400 MHz, CDCl$_3$) δ ppm: 1.03 (3H, t) 1.30 (3H, t) 2.02 (1H, dq) 2.11 (1H, dq) 4.16 (1H, dd) 4.24 (2H, dq)

Reference 11

Preparation of ethyl (S)-2-bromobutyrate

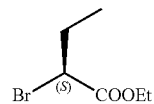

The subject compound was prepared by performing the same operation as those of the references 10(a) to 10(b) by using L-2-aminobutyric acid instead of D-2-aminobutyric acid in the reference 10(a).

$^1$H-NMR (400 MHz, CDCl$_3$) δ ppm: 1.30 (3H, t) 1.83 (1H, d) 4.23 (1H, dq) 4.35 (2H, q)

Reference 12

Preparation of ethyl (R)-2-bromopropionate

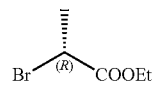

The subject compound was prepared by performing the same operation as that of the reference 10(b) by using commercially available (R)-2-bromopropionic acid instead of (R)-2-bromobutyric acid in the reference 10(b).

Reference 13

Preparation of ethyl (S)-2-bromopropionate

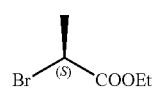

The subject compound was prepared by performing the same operation as that of the reference 10(b) by using commercially available (S)-2-bromopropionic acid instead of (R)-2-bromobutyric acid in the reference 10(b).

Reference 14

Preparation of ethyl (R)-2-bromo-3-methylbutyrate

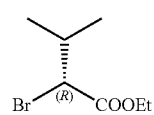

The subject compound was prepared by performing the same operation as those of the references 10(a) to 10(b) by using D-valine instead of D-2-aminobutyric acid in the reference 10(a).

$^1$H-NMR (400 MHz, CDCl$_3$) δ ppm: 1.04 (3H, d) 1.11 (3H, d) 1.30 (3H, t) 2.24 (1H, q) 4.06:4.14 (1H, m) 4.24 (2H, m)

Reference 15

Preparation of ethyl (S)-2-bromo-3-methylbutyrate

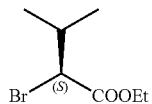

The subject compound was prepared by performing the same operation as those of the references 10(a) to 10(b) by using L-valine instead of for D-2-aminobutyric acid in the reference 10(a).

Reference 16

Preparation of ethyl (R)-2-bromo-valerate

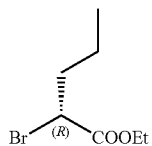

The subject compound was prepared by performing the same operation as those of the references 10(a) to 10(b) by using D-norvaline instead of D-2-aminobutyric acid in the reference 10(a).

$^1$H-NMR (400 MHz, CDCl$_3$) δ ppm: 0.95 (3H, t) 1.30 (3H, t) 1.33-1.54 (2H, m) 1.93-2.10 (2H, m) 4.16-4.27 (1H, m) 4.24 (3H, m)

Reference 17

Preparation of ethyl (S)-2-bromo-valerate

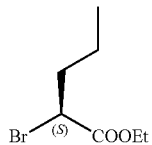

The subject compound was prepared by performing the same operation as those of the references 10(a) to 10(b) by using L-norvaline instead of D-2-aminobutyric acid in the reference 10(a).

Reference 18

Preparation of 2-(9H-carbazole-4-yloxy)-2-methylpropionic acid

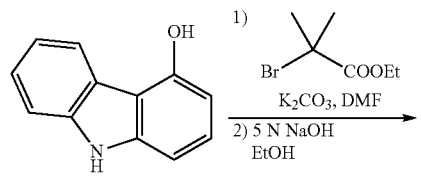

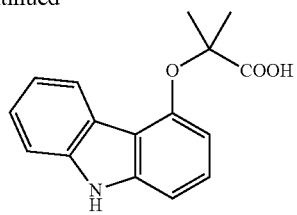

4.35 g of potassium carbonate was added to N,N-dimethylformamide (15 mL) solution of 1 g of 4-hydroxycarbazole and 4.72 g of ethyl 2-bromo-2-methylpropionate, and stirred at 90° C. for 4 hours. The reaction mixture was allowed to cool to room temperature, ice water was added thereto thereafter, and extracted twice with ethyl acetate. The combined extract was washed with brine and dried over anhydrous sodium sulfate. After filtration, the filtrate was concentrated in vacuo. The residue was purified by NH silica gel chromatography (ethyl acetate:n-hexane=1:2), and ethyl 2-(9H-carbazole-4-yloxy)-2-methylpropionate was prepared. 5 N sodium hydroxide solution was added to the prepared ethanol 30 mL solution of ethyl 2-(9H-carbazole-4-yloxy)-2-methylpropionate, and stirred at 70° C. for 1 hour. The reaction mixture was allowed to cool to room temperature, 1 N hydrochloric acid was added thereafter to be acidified, and extracted twice with ethyl acetate. The combined extract was washed with brine and dried over anhydrous sodium sulfate. After filtration, the filtrate was concentrated in vacuo. The filtrate was crystallized from diisopropylether, and isolated by filtration, washed with n-hexane, dried under reduced pressure, and 1.18 g of the subject compound was prepared as yellow crystal.

$^1$H-NMR (400 MHz, DMSO-d$_6$) δ ppm: 1.71 (6H, s) 6.45 (1H, d) 7.06 (1H, d) 7.15 (1H, ddd) 7.23 (1H, dd) 7.35 (1H, ddd) 7.45 (1H, d) 8.20 (1H, d) 11.24 (1H, s) 13.10 (1H, s)

Reference 19

Preparation of 2-(9H-carbazole-4-yloxy) propionic acid

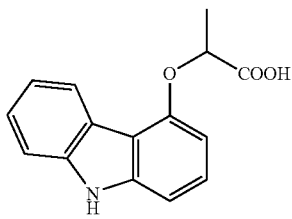

The subject compound was prepared by performing the same operation as that of the reference 11 by using ethyl 2-bromopropionate instead of ethyl 2-bromo-2-methylpropionate in the reference 11.

$^1$H-NMR (400 MHz, DMSO-d$_6$) δ ppm: 1.69 (3H, d) 5.03 (1H, q) 6.52 (1H, d) 7.07 (1H, d), 7.15 (1H, ddd) 7.26 (1H, dd) 7.35 (1H, ddd) 7.45 (1H, d) 8.21 (1H, d) 11.25 (1H, s) 13.08 (1H, br)

Reference 20

Preparation of 2-(9H-carbazole-4-yloxy) butyric acid

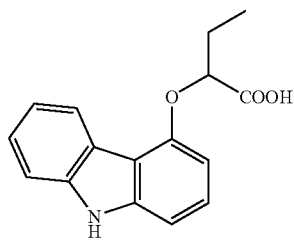

The subject compound was prepared by performing the same operation as that of the reference 18 by using ethyl 2-bromobutyrate instead of ethyl 2-bromo-2-methylpropionate in the reference 18.

$^1$H-NMR (400 MHz, DMSO-$d_6$) δ ppm: 1.15 (3H, t) 2.05-2.13 (1H, m) 4.89 (1H, t) 6.50 (1H, d) 7.07 (1H, d) 7.16 (1H, ddd) 7.26 (1H, dd) 7.35 (1H, ddd) 7.46 (1H, d) 8.21 (1H, d) 11.27 (1H, s) 13.03 (1H, br)

Reference 21

Preparation of 2-(9H-carbazole-4-yloxy)-2-phenylacetic acid

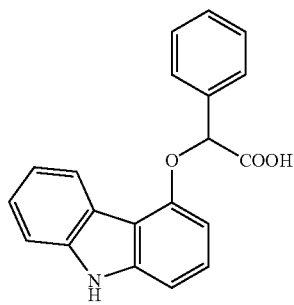

The subject compound was prepared by performing the same operation as that of the reference 18 by using ethyl α-bromophenylacetate instead of ethyl 2-bromo-2-methylpropionate in the reference 18.

$^1$H-NMR (400 MHz, DMSO-$d_6$) δ ppm: 6.08 (1H, s) 6.63 (1H, d) 7.08 (1H, d) 7.17 (1H, ddd) 7.24 (1H, dd) 7.33-7.43 (2H, m) 7.44-7.51 (3H, m) 7.71 (2H, d) 8.31 (1H, d) 11.29 (1H, s) 13.28 (1H, br)

Reference 22

Preparation of 2-(9H-carbazole-4-yloxy) isovaleric acid

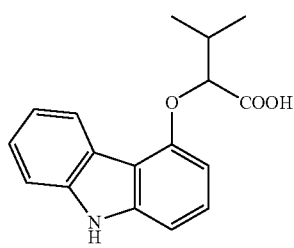

The subject compound was prepared by performing the same operation as that of the reference 18 by using ethyl 2-bromoisovalerate instead of ethyl 2-bromo-2-methylpropionate used in the reference 18.

$^1$H-NMR (400 MHz, DMSO-$d_6$) δ ppm: 1.16 (3H, d) 1.21 (3H, d) 2.15-2.45 (1H, m) 4.74 (1H, d) 6.48 (1H, d) 7.07 (1H, d), 7.15 (1H, ddd) 7.25 (1H, dd) 7.35 (1H, ddd) 7.47 (1H, d) 8.21 (1H, d) 11.28 (1H, s) 13.06 (1H, br)

Reference 23

Preparation of 2-(9H-carbazole-4-yloxy) valeric acid

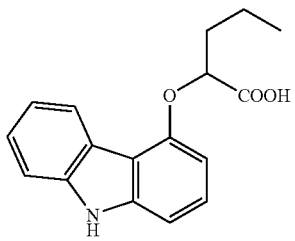

The subject compound was prepared by performing the same operation as that of the reference 18 by using ethyl 2-bromovalerate instead of ethyl 2-bromo-2-methylpropionate in the reference 18.

$^1$H-NMR (400 MHz, DMSO-$d_6$) δ ppm: 0.99 (3H, t) 1.57-1.68 (2H, m) 1.95-2.13 (2H, m) 4.92 (1H, dd) 6.50 (1H, d) 7.07 (1H, d) 7.16 (1H, ddd) 7.26 (1H, dd) 7.35 (1H, ddd) 7.46 (1H, d) 8.19 (1H, d) 11.27 (1H, s) 13.03 (1H, br)

Reference 24

Preparation of 4-(9H-carbazole-4-yloxy) butyric acid

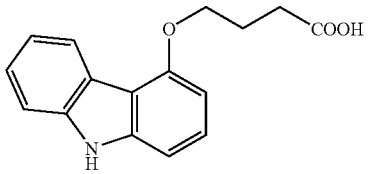

The subject compound was prepared by performing the same operation as that of the reference 18 by using ethyl 4-bromobutyrate instead of ethyl 2-bromo-2-methylpropionate in the reference 18.

$^1$H-NMR (400 MHz, DMSO-$d_6$) δ ppm: 2.10-2.19 (2H, m) 2.55 (2H, t) 4.22 (2H, t) 6.68 (1H, d) 7.07 (1H, d) 7.15 (1H, ddd) 7.29 (1H, dd) 7.34 (1H, ddd) 7.45 (1H, d) 8.14 (1H, d) 11.25 (1H, s) 12.19 (1H, br)

Reference 25

Preparation of 2-(9H-carbazole-4-yloxy) caproic acid

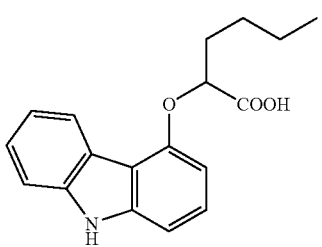

The subject compound was prepared by performing the same operation as that of the reference 18 by using ethyl 2-bromocaproate instead of ethyl 2-bromo-2-methylpropionate in the reference 18.

$^1$H-NMR (400 MHz, DMSO-d$_6$) δ ppm: 0.92 (3H, t) 1.35-1.47 (2H, m) 1.53-1.63 (2H, m) 2.00-2.13 (2H, m) 4.91 (1H, dd) 6.50 (1H, d) 7.07 (1H, d) 7.16 (1H, ddd) 7.26 (1H, dd) 7.35 (1H, ddd) 7.46 (1H, d) 8.19 (1H, d) 11.27 (1H, s) 13.05 (1H, br)

Reference 26

Preparation of 2-(9H-carbazole-4-yloxy) heptane acid

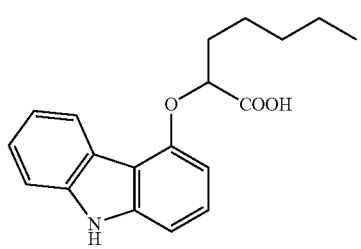

The subject compound was prepared by performing the same operation as that of the reference 18 by using ethyl 2-bromoheptanate instead of ethyl 2-bromo-2-methylpropionate in the reference 18.

$^1$H-NMR (400 MHz, DMSO-d$_6$) δ ppm: 0.88 (3H, t) 1.20-1.43 (4H, m) 1.55-1.66 (2H, m) 1.97-2.13 (2H, m) 4.91 (1H, dd) 6.49 (1H, d) 7.07 (1H, d) 7.15 (1H, ddd) 7.25 (1H, dd) 7.35 (1H, ddd) 7.46 (1H, d) 8.19 (1H, d) 11.27 (1H, s) 13.06 (1H, br)

Reference 27

Preparation of 2-(9H-carbazole-4-yloxy) caprylic acid

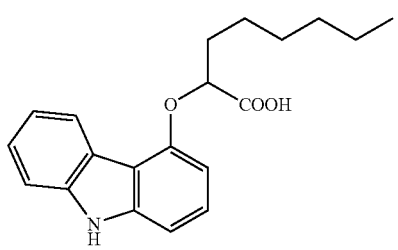

The subject compound was prepared by performing the same operation as that of the reference 18 by using ethyl 2-bromocaprylate instead of ethyl 2-bromo-2-methylpropionate in the reference 18.

$^1$H-NMR (400 MHz, DMSO-d$_6$) δ ppm: 0.86 (3H, t) 1.20-1.35 (4H, m) 1.35-1.44 (2H, m) 1.55-1.64 (2H, m) 1.97-2.13 (2H, m) 4.91 (1H, dd) 6.49 (1H, d) 7.07 (1H, d) 7.15 (1H, ddd) 7.25 (1H, dd) 7.35 (1H, ddd) 7.46 (1H, d) 8.19 (1H, d) 11.27 (1H, s) 13.05 (1H, br)

Reference 28

Preparation of 5-(9H-carbazole-4-yloxy) valeric acid

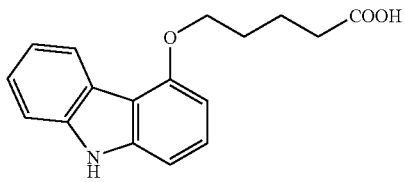

The subject compound was prepared by performing the same operation as that of the reference 18 by using ethyl 5-bromovalerate instead of ethyl 2-bromo-2-methylpropionate in the reference 18.

$^1$H-NMR (400 MHz, DMSO-d$_6$) δ ppm: 1.77-1.87 (2H, m) 1.88-1.98 (2H, m) 2.37 (2H, t) 4.20 (2H, t) 6.68 (1H, d) 7.06 (1H, d) 7.14 (1H, ddd) 7.27 (1H, dd) 7.33 (1H, ddd) 7.44 (1H, d) 8.14 (1H, d) 11.23 (1H, s) 12.09 (1H, br)

Reference 29

Preparation of 6-(9H-carbazole-4-yloxy) caproic acid

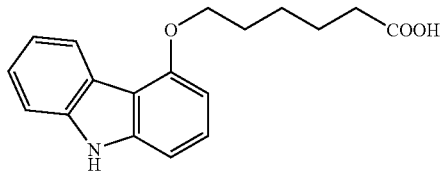

The subject compound was prepared by performing the same operation as that of the reference 18 by using ethyl 6-bromocaproate instead of ethyl 2-bromo-2-methylpropionate in the reference 18.

$^1$H-NMR (400 MHz, DMSO-d$_6$) δ ppm: 1.54-1.70 (4H, m) 1.87-1.97 (2H, m) 2.28 (2H, t) 4.19 (2H, t) 6.68 (1H, d) 7.06 (1H, d) 7.15 (1H, ddd) 7.25 (1H, dd) 7.31 (1H, ddd) 7.47 (1H, d) 8.14 (1H, d) 11.23 (1H, s) 12.03 (1H, br)

Reference 30

Preparation of 3-(9H-carbazole-4-yloxy)-2,2-dimethylpropionic acid

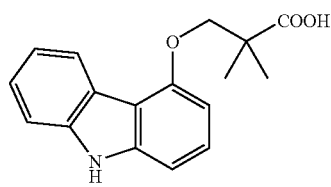

The subject compound was prepared by performing the same operation as that of the reference 18 by using ethyl 3-chloropivalate and potassium iodide instead of ethyl 2-bromo-2-methylpropionate in the reference 18.

$^1$H-NMR (400 MHz, CDCl$_3$) δ ppm: 1.49 (6H, s) 4.24 (1H, s) 6.64 (1H, d) 7.03 (1H, d), 7.21 (1H, ddd) 7.31 (1H, dd) 7.34-7.38 (2H, m) 8.04 (1H, br) 8.26 (1H, d) (proton of carboxylic acid was not observed)

Reference 31

Preparation of
4-(9H-carbazole-4-yloxy)-2-methylbutyric acid

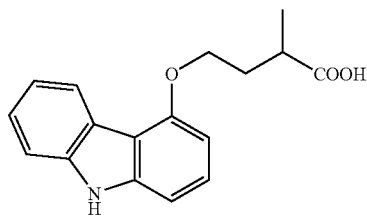

The subject compound was prepared by performing the same operation as that of the reference 18 by using ethyl 4-chloro-2-methylbutyrate instead of ethyl 2-bromo-2-methylpropionate in the reference 18.

$^1$H-NMR (400 MHz, DMSO-$d_6$) δ ppm: 1.22 (3H, m) 1.91-2.02 (1H, m) 2.19-2.29 (1H, m) 2.69-2.79 (1H, m) 4.18-4.29 (2H, m) 6.69 (1H, d) 7.07 (1H, d) 7.15 (1H, ddd) 7.29 (1H, dd) 7.34 (1H, ddd) 7.45 (1H, d) 8.14 (1H, d) 11.24 (1H, s) 12.25 (1H, br)

Example 1

Preparation of 2-{9-[3-methoxy-4-((5-methyl-2-phenyl-oxazole-4-yl)methoxy)-benzyl]-9H-carbazole-4-yloxy}acetic acid

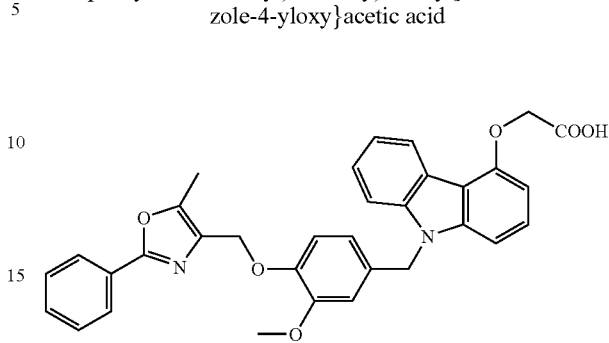

Example 1(a)

Preparation of ethyl 2-{9-[3-methoxy-4-((5-methyl-2-phenyl-oxazole-4-yl)methoxy)-benzyl]-9H-carbazole-4-yloxy}acetate

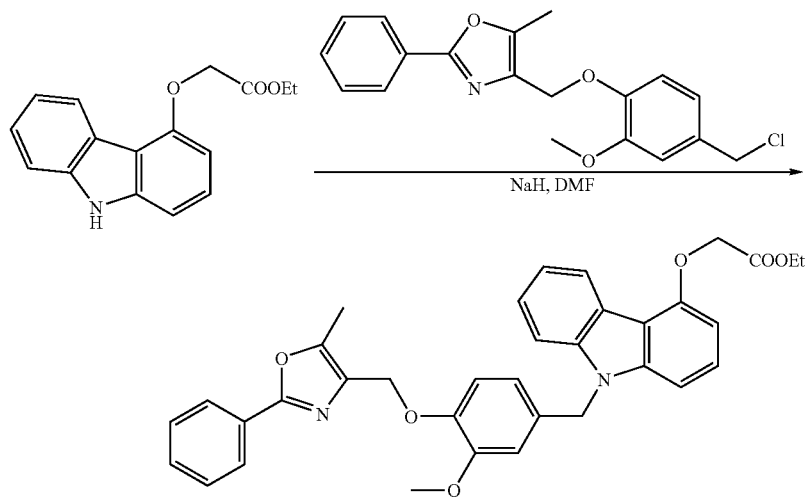

18 mg of sodium hydride (60%) was added to N,N-dimethylformamide (5 mL) solution of 107 mg of ethyl 2-(9H-carbazole-4-yloxy)acetate, and stirred at room temperature for 20 minutes. Thereafter, 144 mg of 4-((4-(chloromethyl)-2-methoxyphenoxy)methyl)-5-methyl-2-phenyloxazole was added thereto, and stirred at room temperature for 1 hour. The reaction mixture was poured into water, and extracted twice with ethyl acetate. The combined extract was washed with brine, and dried over anhydrous sodium sulfate. After filtration, the filtrate was concentrated in vacuo, the residue was crystallized from methanol, isolated by filtration, and washed with methanol. The residue was dried under reduced pressure, and 107 mg of the subject compound was prepared as white crystal.

$^1$H-NMR (270 MHz, DMSO-$d_6$) δ ppm: 1.27 (3H, t) 2.37 (3H, s) 3.67 (3H, s) 4.25 (2H, q) 4.87 (2H, s) 5.05 (2H, s) 5.57 (2H, s) 6.64 (1H, d) 6.69 (1H, d) 6.94 (1H, d) 7.02 (1H, s) 7.20-7.45 (4H, m) 7.45-7.55 (3H, m) 7.64 (1H, d) 7.88-8.97 (2H, m) 8.34 (1H, d)

Example 1(b)

Preparation of 2-{9-[3-methoxy-4-((5-methyl-2-phenyl-oxazole-4-yl)methoxy)-benzyl]-9H-carbazole-4-yloxy}acetic acid

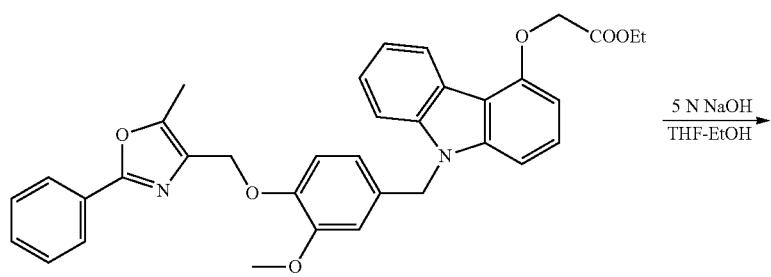

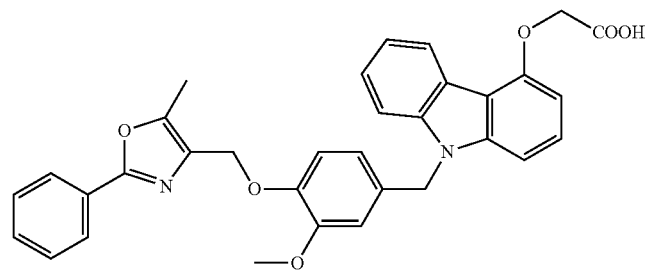

1 mL of 5 N sodium hydroxide solution was added to tetrahydrofuran:methanol=1:1 (10 mL) solution of 107 mg of ethyl 2-{9-[3-methoxy-4-((5-methyl-2-phenyl-oxazole-4-yl)methoxy)-benzyl]-9H-carbazole-4-yloxy}acetate, and stirred at room temperature for 1 hour. The reaction mixture was diluted with water, adjusted to pH3 by 1 N hydrochloric acid, and extracted with ethyl acetate. The extract was washed with brine, and dried over anhydrous sodium sulfate. After filtration, the filtrate was concentrated in vacuo. The crystals of residue were isolated by filtration with ethyl acetate-diisopropylether, dried under reduced pressure, and 74 mg of the subject compound was prepared as pale yellow crystal.

$^1$H-NMR and MS spectrum data are shown in Table 1.

Example 2

Preparation of 2-{9-[4-((2-(furan-2-yl)-5-methyl-oxazole-4-yl)methoxy)-3-methoxy-benzyl]-9H-carbazole-4-yloxy}acetic acid

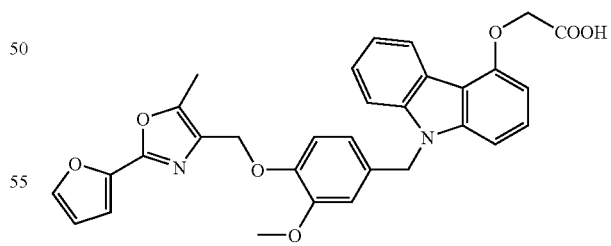

The subject compound was prepared by performing the same operation as those of the examples 1(a) to 1(b) by using 4-((4-(chloromethyl)-2-methoxyphenoxy)methyl)-2-(furan-2-yl)-5-methyloxazole prepared by the reference 2 instead of 4-((4-(chloromethyl)-2-methoxyphenoxy)methyl)-5-methyl-2-phenyloxazole in the example 1(a).

$^1$H-NMR and MS spectrum data is shown in Table 1.

Example 3

Preparation of 2-{9-[3-methoxy-4-((5-methyl-2-phenyl-oxazole-4-yl)methoxy)-benzyl]-9H-carbazole-4-yloxy}-2-methyl-propionic acid

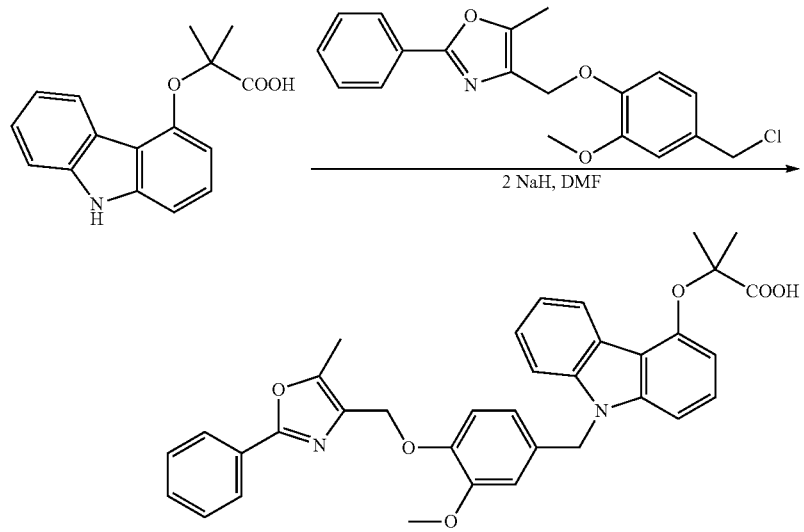

302 mg of sodium hydride (60%) was added to N,N-dimethylformamide (30 mL) solution of 924 mg of 2-(9H-carbazole-4-yloxy)-2-methylpropionic acid, stirred at room temperature for 20 minutes. Thereafter, 1.31 g of 4-((4-(chloromethyl)-2-methoxyphenoxy)methyl)-5-methyl-2-phenyloxazole was added thereto, and stirred at room temperature for 1 hour. The reaction mixture was poured into water, adjusted to pH3 with 1 N hydrochloric acid, and extracted twice with ethyl acetate. The combined extract was washed with brine, and dried over anhydrous sodium sulfate. After filtration, the filtrate was concentrated in vacuo, the residue was purified by silica gel chromatography (chloroform:methanol=50:1), and 1.88 g of the subject compound was prepared as pale yellow powder.

$^1$H-NMR and MS spectrum data is shown in Table 1.

Example 4

Preparation of (±)-2-{9-[3-methoxy-4-((5-methyl-2-phenyl-oxazole-4-yl)methoxy)-benzyl]-9H-carbazole-4-yloxy}propionic acid

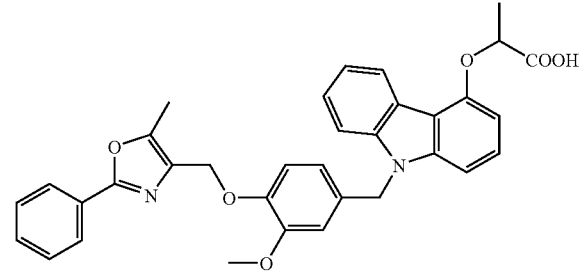

The subject compound was prepared by performing the same operation as that of the example 3 by using 2-(9H-carbazole-4-yloxy) propionic acid prepared by the reference 19 instead of 2-(9H-carbazole-4-yloxy)-2-methylpropionic acid used in the example 3.

$^1$H-NMR and MS spectrum data is shown in Table 1.

Example 5

Preparation of (±)-2-{9-[3-methoxy-4-((5-methyl-2-phenyl-oxazole-4-yl)methoxy)-benzyl]-9H-carbazole-4-yloxy}butyric acid

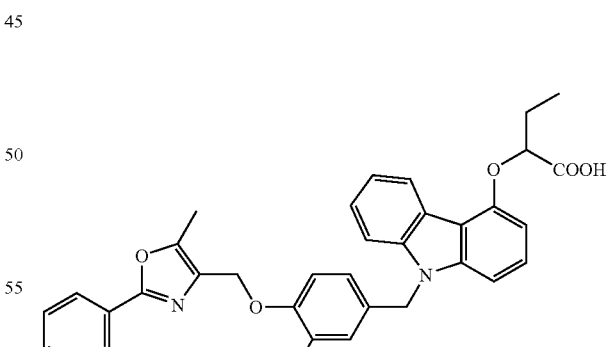

The subject compound was prepared by performing the same operation as that of the example 3 by using 2-(9H-carbazole-4-yloxy) butyric acid prepared by the reference 20 instead of 2-(9H-carbazole-4-yloxy)-2-methylpropionic acid used in the example 3.

$^1$H-NMR and MS spectrum data is shown in Table 1.

Example 6

Preparation of (±)-2-{9-[4-((2-(furan-2-yl)-5-methyl-oxazole-4-yl)methoxy)-3-methoxy-benzyl]-9H-carbazole-4-yloxy}-2-phenylacetic acid

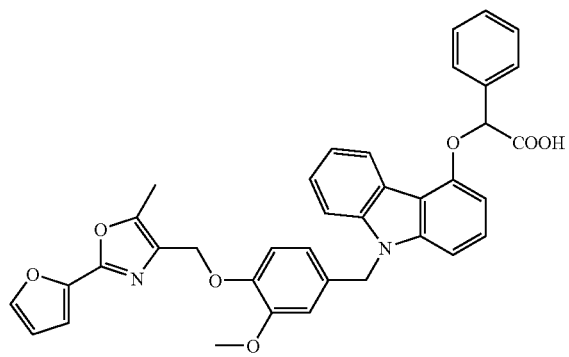

The subject compound was prepared by performing the same operation as that of the example 3 by using 2-(9H-carbazole-4-yloxy)-2-phenylacetic acid prepared by the reference 21 instead of 2-(9H-carbazole-4-yloxy)-2-methylpropionic acid used in the example 3, and using 4-((4-(chloromethyl)-2-methoxyphenoxy)methyl)-2-(furan-2-yl)-5-methyloxazole prepared by the reference 2 instead of 4-((4-(chloromethyl)-2-methoxyphenoxy)methyl)-5-methyl-2-phenyloxazole.

$^1$H-NMR and MS spectrum data is shown in Table 1.

Example 7

Preparation of 2-{9-[4-((2-(furan-2-yl)-5-methyl-oxazole-4-yl)methoxy)-3-methoxy-benzyl]-9H-carbazole-4-yloxy-}2-methyl-propionic acid

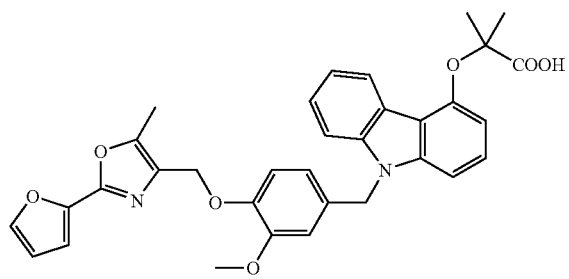

The subject compound was prepared by performing the same operation as that of the example 3 by using 4-((4-(chloromethyl)-2-methoxyphenoxy)methyl)-2-(furan-2-yl)-5-methyloxazole prepared by the reference 2 instead of 4-((4-(chloromethyl)-2-methoxyphenoxy)methyl)-5-methyl-2-phenyloxazole used in the example 3.

$^1$H-NMR and MS spectrum data is shown in Table 1.

Example 8

Preparation of 2-{9-[3-methoxy-4-((5-methyl-2-(thiophene-2-yl)-oxazole-4-yl)methoxy)-benzyl]-9H-carbazole-4-yloxy}-2-methyl-propionic acid

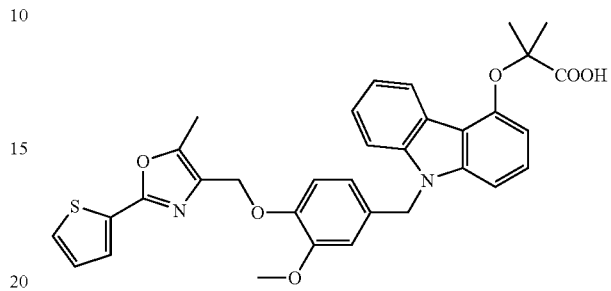

The subject compound was prepared by performing the same operation as that of the example 3 by using 4-((4-(chloromethyl)-2-methoxyphenoxy)methyl)-2-(thiophene-2-yl)-5-methyloxazole prepared by the reference 3 instead of 4-((4-(chloromethyl)-2-methoxyphenoxy)methyl)-5-methyl-2-phenyloxazole used in the example 3.

$^1$H-NMR and MS spectrum data is shown in Table 1.

Example 9

Preparation of 2-{9-[3-methoxy-4-((5-methyl-2-(pyridine-4-yl)-oxazole-4-yl)methoxy)-benzyl]-9H-carbazole-4-yloxy}-2-methyl-propionic acid

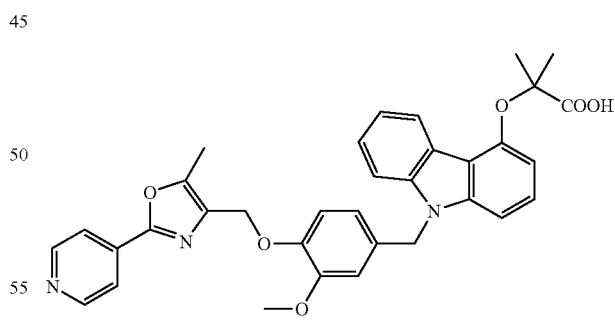

The subject compound was prepared by performing the same operation as that of the example 3 by using 4-((4-(chloromethyl)-2-methoxyphenoxy)methyl)-2-(pyridine-4-yl)-5 methyloxazole prepared by the reference 4 instead of 4-((4-(chloromethyl)-2-methoxyphenoxy)methyl)-5-methyl-2-phenyloxazole used in the example 3.

$^1$H-NMR and MS spectrum data is shown in Table 1.

Example 10

Preparation of (±)-2-{9-[3-methoxy-4-((5-methyl-2-phenyl-oxazole-4-yl)methoxy)-benzyl]-9H-carbazole-4-yloxy}-3-methyl-butyric acid

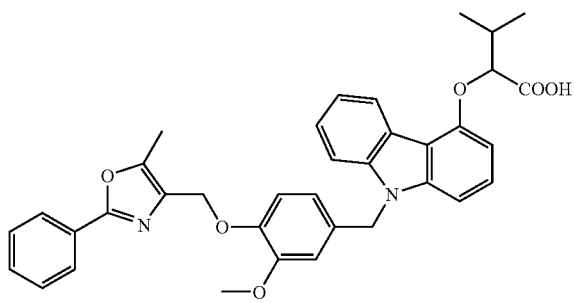

The subject compound was prepared by performing the same operation as that of the example 3 by using 2-(9H-carbazole-4-yloxy) isovaleric acid prepared by the reference 22 instead of 2-(9H-carbazole-4-yloxy)-2-methylpropionic acid used in the example 3.
$^1$H-NMR and MS spectrum data is shown in Table 1.

Example 11

Preparation of (±)-2-{9-[3-methoxy-4-((5-methyl-2-phenyl-oxazole-4-yl)methoxy)-benzyl]-9H-carbazole-4-yloxy}valeric acid

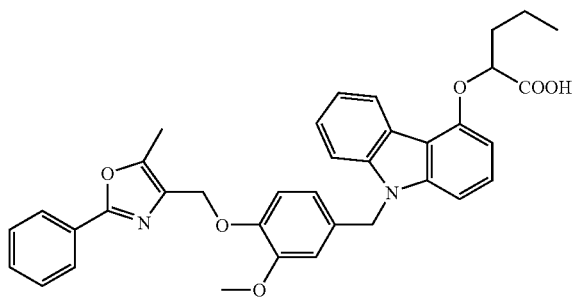

The subject compound was prepared by performing the same operation as that of the example 3 by using 2-(9H-carbazole-4-yloxy) valeric acid prepared by the reference 23 instead of 2-(9H-carbazole-4-yloxy)-2-methylpropionic acid used in the example 3.
$^1$H-NMR and MS spectrum data is shown in Table 1.

Example 12

Preparation of 4-{9-[3-methoxy-4-((5-methyl-2-phenyl-oxazole-4-yl)methoxy)-benzyl]-9H-carbazole-4-yloxy}butyric acid

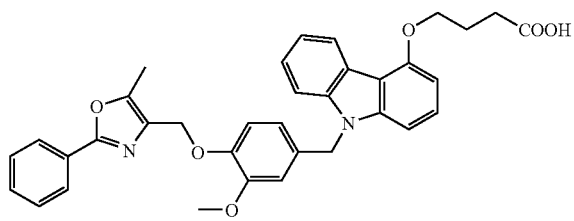

The subject compound was prepared by performing the same operation as that of the example 3 by using 4-(9H-carbazole-4-yloxy) butyric acid prepared by the reference 24 instead of 2-(9H-carbazole-4-yloxy)-2-methylpropionic acid used in the example 3.
$^1$H-NMR and MS spectrum data is shown in Table 1.

Example 13

Preparation of 2-methyl-2-{9-[4-((5-methyl-2-phenyl-oxazole-4-yl)methoxy)-benzyl]-9H-carbazole-4-yloxy}propionic acid

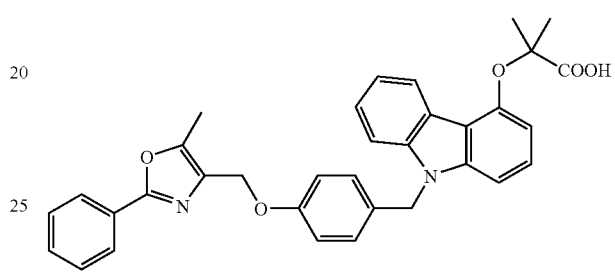

The subject compound was prepared by performing the same operation as that of the example 3 by using 4-((4-(chloromethyl)phenoxy)methyl)-5-methyl-2-phenylthiazole prepared by the reference 7 instead of 4-((4-(chloromethyl)-2-methoxyphenoxy)methyl)-5-methyl-2-phenyloxazole used in the example 3.
$^1$H-NMR and MS spectrum data is shown in Table 1.

Example 14

Preparation of 2-{9-[3-((2-(furan-2-yl)-5-methyl-oxazole-4-yl)methoxy)-4-methoxy-benzyl]-9H-carbazole-4-yloxy}-2-methyl-propionic acid

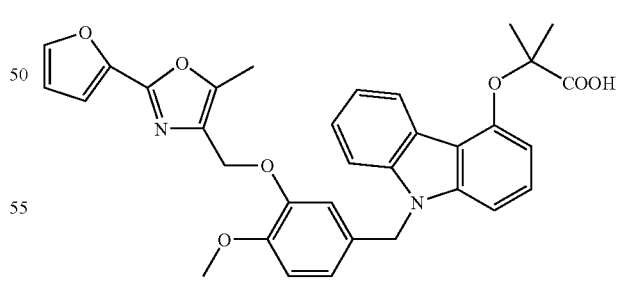

The subject compound was prepared by performing the same operation as that of the example 3 by using 4-((5-(chloromethyl)-2-methoxyphenoxy)methyl)-2-(furan-2-yl)-5-methyloxazole prepared by the reference 8 instead of 4-((4-(chloromethyl)-2-methoxyphenoxy)methyl)-5-methyl-2-phenyloxazole used in the example 3.
$^1$H-NMR and MS spectrum data is shown in Table 1.

Example 15

Preparation of 2-{9-[3-methoxy-4-((5-methyl-2-phenyl-thiazole-4-yl)methoxy)-benzyl]-9H-carbazole-4-yloxy}-2-methyl-propionic acid

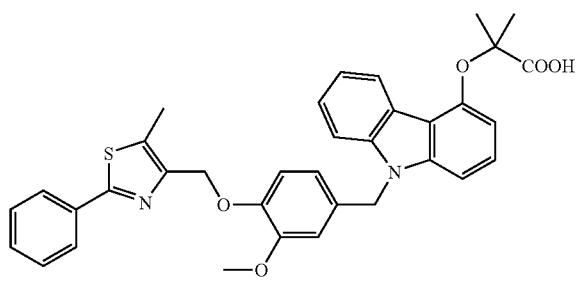

The subject compound was prepared by performing the same operation as that of the example 3 by using 4-((4-(chloromethyl)-2-methoxyphenoxy)methyl)-5-methyl-2-phenylthiazole prepared by the reference 5 instead of 4-((4-(chloromethyl)-2-methoxyphenoxy)methyl)-5-methyl-2-phenyloxazole used in the example 3.
$^1$H-NMR and MS spectrum data is shown in Table 1.

Example 16

Preparation of 2-{9-[3-methoxy-4-((4-methyl-2-phenyl-thiazole-5-yl)methoxy)-benzyl]-9H-carbazole-4-yloxy}-2-methyl-propionic acid

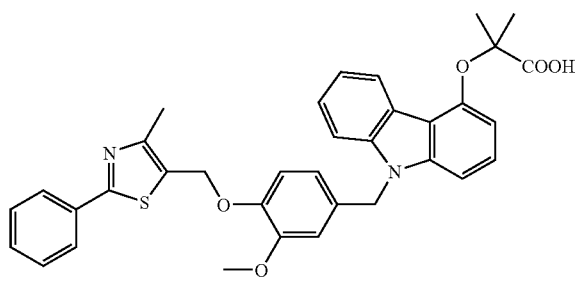

The subject compound was prepared by performing the same operation as that of the example 3 by using 54(4-(chloromethyl)-2-methoxyphenoxy)methyl)-4-methyl-2-phenylthiazole prepared by the reference 6 instead of 4-((4-(chloromethyl)-2-methoxyphenoxy)methyl)-5-methyl-2-phenyloxazole used in the example 3.
$^1$H-NMR and MS spectrum data is shown in Table 1.

Example 17

Preparation of (±)-2-{9-[3-methoxy-4-((5-methyl-2-phenyl-oxazole-4-yl)methoxy)-benzyl]-9H-carbazole-4-yloxy}caproic acid

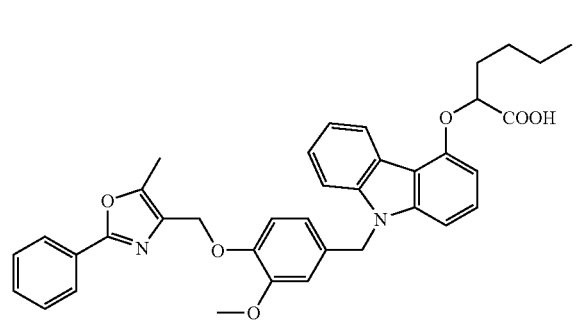

The subject compound was prepared by performing the same operation as that of the example 3 by using 2-(9H-carbazole-4-yloxy) caproic acid prepared by the reference 25 instead of 2-(9H-carbazole-4-yloxy)-2-methylpropionic acid used in the example 3.
$^1$H-NMR and MS spectrum data is shown in Table 1.

Example 18

Preparation of (±)-2-{9-[3-methoxy-4-((5-methyl-2-phenyl-oxazole-4-yl)methoxy)-benzyl]-9H-carbazole-4-yloxy}heptane acid

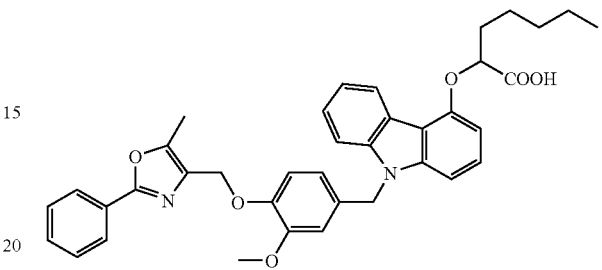

The subject compound was prepared by performing the same operation as that of the example 3 by using 2-(9H-carbazole-4-yloxy) heptane acid prepared by the reference 26 instead of 2-(9H-carbazole-4-yloxy)-2-methylpropionic acid used in the example 3.
$^1$H-NMR and MS spectrum data is shown in Table 1.

Example 19

Preparation of (±)-2-{9-[3-methoxy-4-((5-methyl-2-phenyl-oxazole-4-yl)methoxy)-benzyl]-9H-carbazole-4-yloxy}caprylic acid

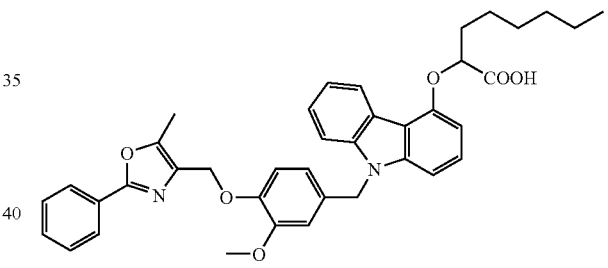

The subject compound was prepared by performing the same operation as that of the example 3 by using 2-(9H-carbazole-4-yloxy) caprylic acid prepared by the reference 27 instead of 2-(9H-carbazole-4-yloxy)-2-methylpropionic acid used in the example 3.
$^1$H-NMR and MS spectrum data is shown in Table 1.

Example 20

Preparation of 5-{9-[3-methoxy-4-((5-methyl-2-phenyl-oxazole-4-yl)methoxy)-benzyl]-9H-carbazole-4-yloxy}valeric acid

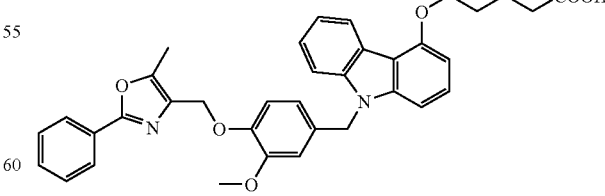

The subject compound was prepared by performing the same operation as that of the example 3 by using 5-(9H-carbazole-4-yloxy) valeric acid prepared by the reference 28 instead of 2-(9H-carbazole-4-yloxy)-2-methylpropionic acid used in the example 3.
$^1$H-NMR and MS spectrum data is shown in Table 1.

Example 21

Preparation of 6-{9-[3-methoxy-4-((5-methyl-2-phenyl-oxazole-4-yl)methoxy)-benzyl]-9H-carbazole-4-yloxy}caproic acid

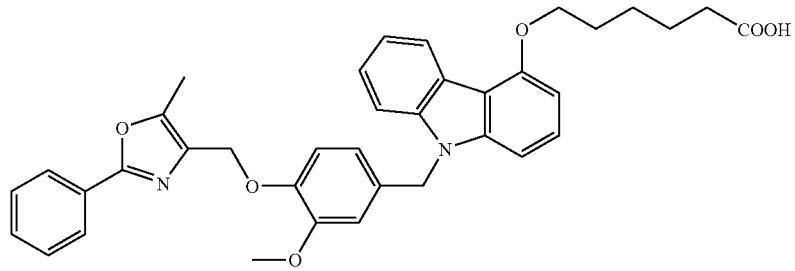

The subject compound was prepared by performing the same operation as that of the example 3 by using 6-(9H-carbazole-4-yloxy) caproic acid prepared by the reference 29 instead of 2-(9H-carbazole-4-yloxy)-2-methylpropionic acid used in the example 3.
$^1$H-NMR and MS spectrum data is shown in Table 1.

Example 22

Preparation of 3-{9-[3-methoxy-4-((5-methyl-2-phenyl-oxazole-4-yl)methoxy)-benzyl]-9H-carbazole-4-yloxy}-2,2-dimethyl-propionic acid

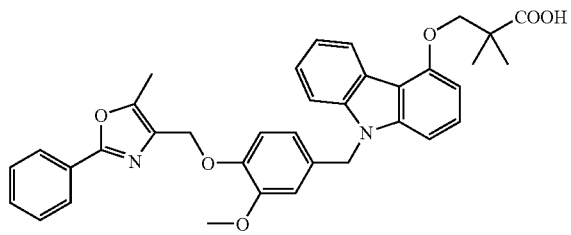

The subject compound was prepared by performing the same operation as that of the example 3 by using 3-(9H-carbazole-4-yloxy)-2,2-dimethylpropionic acid prepared by the reference 30 instead of 2-(9H-carbazole-4-yloxy)-2-methylpropionic acid used in the example 3.
$^1$H-NMR and MS spectrum data is shown in Table 1.

Example 23

Preparation of 3-{9-[4-((2-(furan-2-yl)-5-methyl-oxazole-4-yl)methoxy)-3-methoxy-benzyl]-9H-carbazole-4-yloxy}-2,2-dimethyl-propionic acid

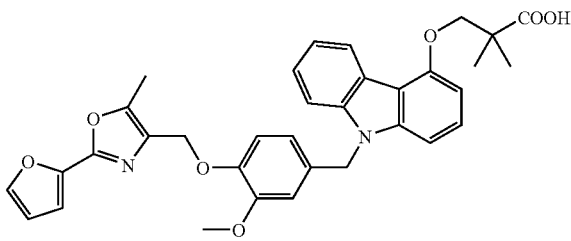

The subject compound was prepared by performing the same operation as that of the example 3 by using 3-(9H-carbazole-4-yloxy)-2,2-dimethylpropionic acid prepared by the reference 30 instead of 2-(9H-carbazole-4-yloxy)-2-methylpropionic acid used in the example 3, and using 4-((4-(chloromethyl)-2-methoxyphenoxy)methyl)-2-(furan-2-yl)-5-methyloxazole prepared by the reference 2 instead of 4-((4-(chloromethyl)-2-methoxyphenoxy)methyl)-5-methyl-2-phenyloxazole.

$^1$H-NMR and MS spectrum data is shown in Table 1.

Example 24

Preparation of 3-{9-[3-methoxy-4-((5-methyl-2-(thiophene-2-yl)-oxazole-4-yl)methoxy)-benzyl]-9H-carbazole-4-yloxy}-2,2-dimethyl-propionic acid

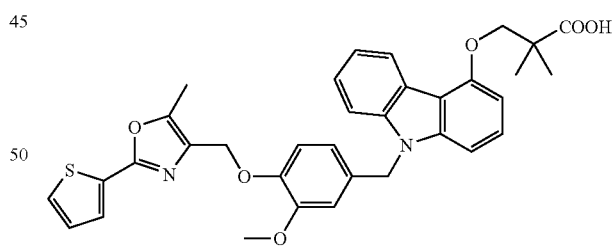

The subject compound was prepared by performing the same operation as that of the example 3 by using 3-(9H-carbazole-4-yloxy)-2,2-dimethylpropionic acid prepared by the reference 30 instead of 2-(9H-carbazole-4-yloxy)-2-methylpropionic acid used in the example 3, and using 4-((4-(chloromethyl)-2-methoxyphenoxy)methyl)-2-(thiophene-2-yl)-5-methyloxazole prepared by the reference 3 instead of 4-((4-(chloromethyl)-2-methoxyphenoxy)methyl)-5-methyl-2-phenyloxazole.

$^1$H-NMR and MS spectrum data is shown in Table 1.

Example 25

Preparation of 3-{9-[3-methoxy-4-((5-methyl-2-pyridine-4-yl-oxazole-4-yl)methoxy)-benzyl]-9H-carbazole-4-yloxy}-2,2-dimethyl-propionic acid

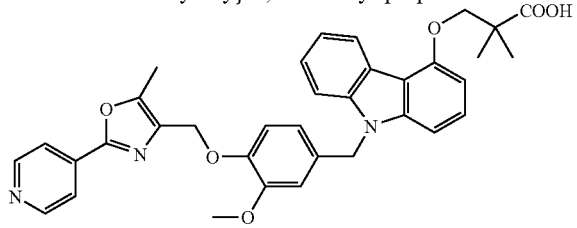

The subject compound was prepared by performing the same operation as that of the example 3 by using 3-(9H-carbazole-4-yloxy)-2,2-dimethylpropionic acid prepared by the reference 30 instead of 2-(9H-carbazole-4-yloxy)-2-methylpropionic acid used in the example 3, and using 4-((4-(chloromethyl)-2-methoxyphenoxy)methyl)-2-(pyridine-4-yl)-5 methyloxazole prepared by the reference 4 instead of 4-((4-(chloromethyl)-2-methoxyphenoxy)methyl)-5-methyl-2-phenyloxazole.
$^1$H-NMR and MS spectrum data is shown in Table 1.

Example 26

Preparation of (±)-2-{9-[3-methoxy-4-((5-methyl-2-phenyl-oxazole-4-yl)methoxy)-benzyl]-9H-carbazole-4-yloxy}-2-phenylacetic acid

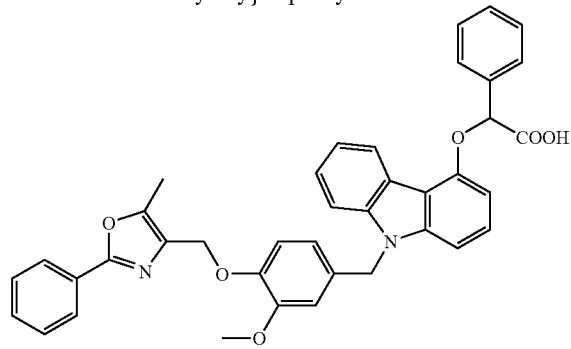

The subject compound was prepared by performing the same operation as that of the example 3 by using 2-(9H-carbazole-4-yloxy)-2-phenylacetic acid prepared by the reference 21 instead of 2-(9H-carbazole-4-yloxy)-2-methylpropionic acid used in the example 3.
$^1$H-NMR and MS spectrum data is shown in Table 1.

Example 27

Preparation of (±)-4-{9-[3-methoxy-4-((5-methyl-2-phenyl-oxazole-4-yl)methoxy)-benzyl]-9H-carbazole-4-yloxy}-2-methyl-butyric acid

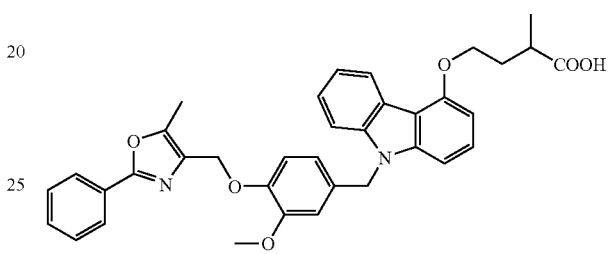

The subject compound was prepared by performing the same operation as that of the example 3 by using 4-(9H-carbazole-4-yloxy)-2-methylbutyric acid prepared by the reference 31 instead of 2-(9H-carbazole-4-yloxy)-2-methylpropionic acid used in the example 3.
$^1$H-NMR and MS spectrum data is shown in Table 1.

Example 28

Preparation of sodium 2-{9-[3-methoxy-4-((5-methyl-2-phenyl-oxazole-4-yl)methoxy)-benzyl]-9H-carbazole-4-yloxy}-2-methyl-propionate

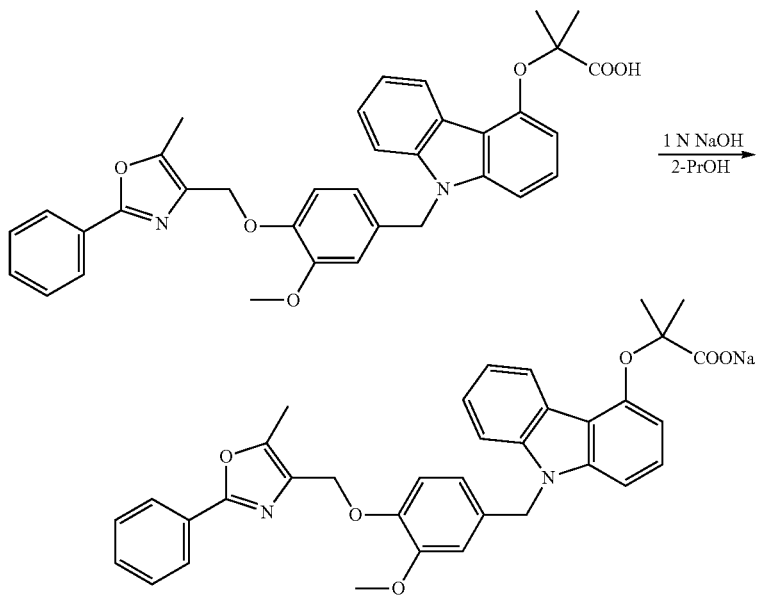

1.88 g of 2-{9-[3-methoxy-4-((5-methyl-2-phenyl-oxazole-4-yl)methoxy)-benzyl]-9H-carbazole-4-yloxy}-2-methyl-propionic acid was suspended in 30 mL of 2-propanol, and dissolved at 70° C. 3.3 mL of 1 N sodium hydroxide solution was added thereto and stirred for 0.5 hour. The reaction mixture was allowed to cool, the precipitate crystal was isolated by filtration, washed with 2-propanol, dried under reduced pressure, and 1.66 g of the subject compound was prepared as white crystal.

$^1$H-NMR and MS spectrum data is shown in Table 1.

Examples 29-37

Compounds of the table were prepared in the same way as the example 28.

Example 38

Preparation of sodium (S)-(+)-2-{9-[3-methoxy-4-((5-methyl-2-phenyl-oxazole-4-yl)methoxy)-benzyl]-9H-carbazole-4-yloxy}butyrate

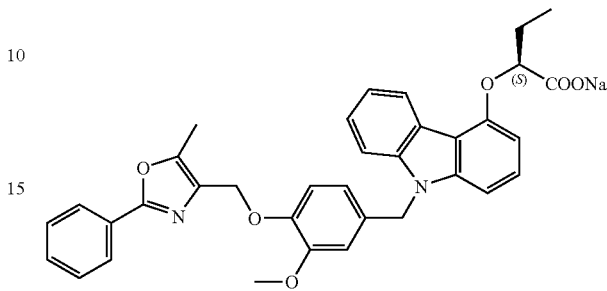

Example 38(a)

Preparation of 9-{4-[(5-methyl-2-phenyloxazole-4-yl)methoxy]-3-methoxybenzyl}-4-(allyloxy)-9H-carbazole

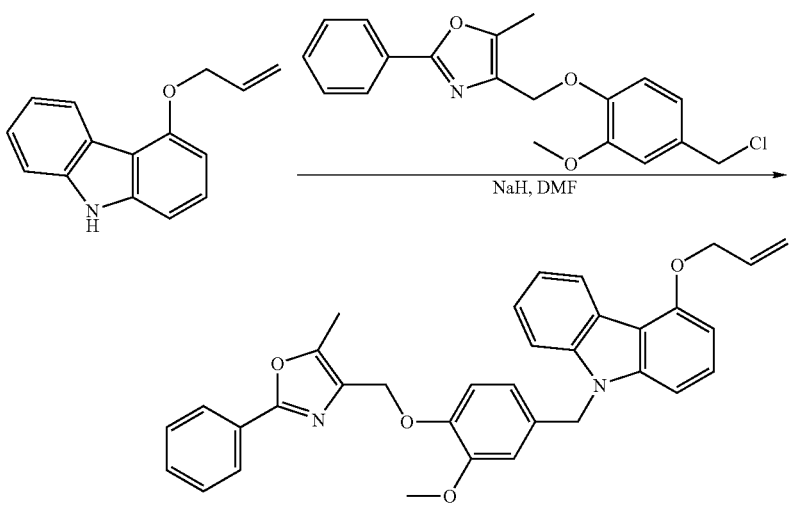

6.05 g of sodium hydride (60%) was added to N,N-dimethylformamide (170 mL) solution of 35 g of 4-(allyloxy)-9H-carbazole while being cooled in an ice bath, and stirred at room temperature for 1 hour. Thereafter, 49.4 g of 4-((4-(chloromethyl)-2-methoxyphenoxy)methyl)-5-methyl-2-phenyloxazole was added thereto, and stirred for 1 hour. The reaction mixture was diluted with mixture of ethyl acetate:n-hexane=1:1 (340 mL), poured into ice water (680 mL), and stirred for 1 hour. The crystalline precipitate was isolated by filtration, and washed with mixture of ethyl acetate:n-hexane=1:1. The crystalline precipitate was dried under reduced pressure, and 55.4 g the subject compound was prepared as pale yellow crystal.

$^1$H-NMR (400 MHz, CDCl$_3$) δ ppm: 2.35 (3H, s) 3.69 (3H, s) 4.82 (2H, ddd) 4.97 (2H, s) 5.37 (1H, ddt) 5.43 (2H, s) 5.58 (1H, ddt) 6.26 (1H, ddt) 6.63 (1H, dd) 6.69 (1H, d) 6.71 (1H, d) 6.90 (1H, d) 7.00 (1H, d) 7.22-7.44 (7H, m) 7.97-8.00 (2H, m) 8.40 (1H, d)

Example 38(b)

Preparation of 9-{4-[(5-methyl-2-phenyloxazole-4-yl)methoxy]-3-methoxybenzyl}-9H-carbazole-4-ol

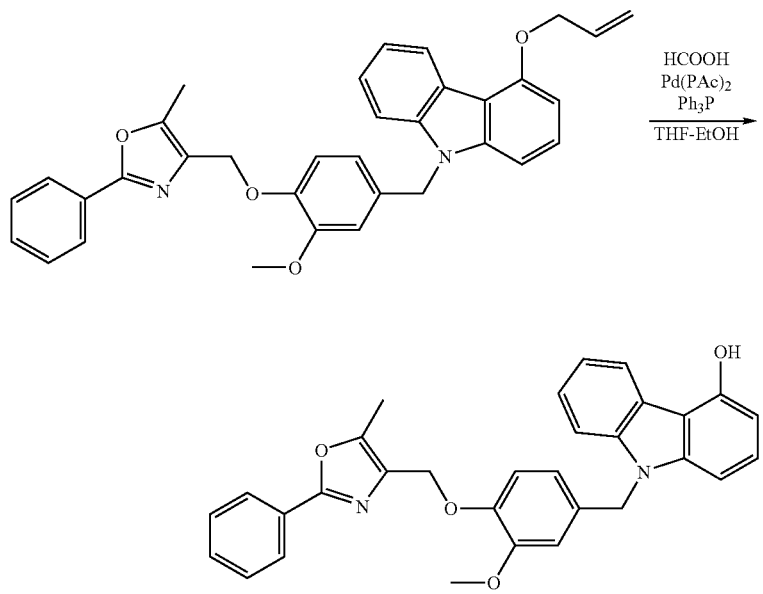

10 g of 9-{4-[(5-methyl-2-phenyloxazole-4-yl)methoxy]-3-methoxybenzyl}-4-(allyloxy)-9H-carbazole was suspended in mixed solution (70 mL) of tetrahydrofuran-ethanol=4:1, 986 mg of triphenylphosphine, 84 mg of palladium acetate, and 2.1 mL of formic acid were added, and refluxed for 5 hours. The reaction mixture was allowed to cool, and then concentrated in vacuo, and the residue was crystallized from 10 mL of ethanol. The crystalline precipitate was isolated by filtration, washed with ethanol, dried under reduced pressure, and 8.96 g of the subject compound was prepared as pale yellow crystal.

$^1$H-NMR (400 MHz, DMSO-$d_6$) δ ppm: 2.37 (3H, s) 3.67 (3H, s) 4.87 (2H, s) 5.51 (2H, s) 6.55 (1H, dd) 6.62 (1H, d) 6.94 (1H, d) 7.02 (1H, d) 7.07 (1H, d) 7.16 (1H, dd) 7.21 (1H, dd) 7.36 (1H, ddd) 7.47-7.54 (3H, m) 7.58 (1H, d) 7.88-7.94 (2H, m) 8.19 (1H, d) 10.12 (1H, s)

Example 38(c)

Preparation of ethyl (S)-(+)-2-{9-[3-methoxy-4-((5-methyl-2-phenyl-oxazole-4-yl)methoxy)-benzyl]-9H-carbazole-4-yloxy}butyrate

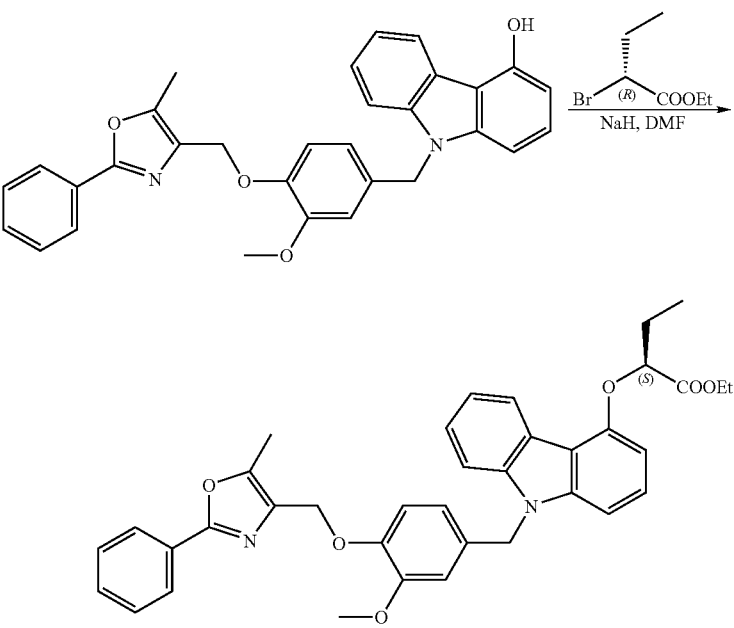

41 mg of sodium hydride (60%) was added to N,N-dimethylformamide (2.5 mL) solution of 500 mg of 9-{4-[(5-methyl-2-phenyloxazole-4-yl)methoxy]-3-methoxybenzyl}-9H-carbazole-4-ol while being cooled in an ice bath, and stirred at room temperature for 1 hour. Thereafter, 239 mg of ethyl (R)-2-bromobutyrate was added thereto dropwise at −5° C., and was stirred for 30 minutes. Water was added to the reaction mixture, and extracted twice with ethyl acetate. The combined extract was washed with brine, and dried over anhydrous sodium sulfate. After filtration, the filtrate was concentrated in vacuo, the residue was purified by NH silica gel chromatography (ethyl acetate:n-hexane=1:4), and 650 mg of the subject compound was prepared. Optical purity 95% ee (HPLC).
Column: CHIRALPAK AD-H 0.46×15 cm (Daicel Chemical Industries, Ltd.)

Eluate: n-hexane:2-propanol=90:10

Flow rate: 0.7 mL/min

Temperature: 35° C.

Detection: UV 230 nm $[\alpha]_D^{28}$ +14.1° (c 1.01, CHCl$_3$)

$^1$H-NMR (400 MHz, DMSO-d$_6$) δ ppm: 1.14 (3H, t) 1.19 (3H, t) 2.10 (2H, q) 2.37 (s, 3H) 3.68 (s, 3H) 4.19 (2H, q) 4.87 (s, 2H) 5.06 (1H, t) 5.56 (s, 2H) 6.54 (1H, dd) 6.56 (1H, d) 6.94 (1H, d) 7.04 (1H, d) 7.23 (1H, dd) 7.28 (1H, d) 7.32 (1H, dd) 7.42 (1H, ddd) 7.47-7.54 (3H, m) 7.65 (1H, d) 7.88-7.94 (2H, m) 8.27 (1H, d)

Example 38(d)

Preparation of (S)-(+)-2-{9-[3-methoxy-4-((5-methyl-2-phenyl-oxazole-4-yl)methoxy)-benzyl]-9H-carbazole-4-yloxy}butyric acid 440 mg of ethyl (S)-(+)-2-{9-[3-methoxy-4-(5-methyl-2-phenyl-oxazole-4-ylmethoxy)-benzyl]-9H-carbazole-4-yloxy}butyrate was suspended in ethanol (4.4 mL), 175 μL of 5 N sodium hydroxide solution was added thereto, and stirred at room temperature for 4 hours. The reaction mixture was diluted with water, and adjusted to pH3 with 1 N hydrochloric acid, and extracted with ethyl acetate. The extract was washed with brine, and dried over anhydrous sodium sulfate. After filtration, the filtrate was concentrated in vacuo, and 420 mg of the subject compound was prepared as white solid. Optical purity 95% ee (HPLC).

Column: CHIRALCEL OD-H 0.46×25 cm (Daicel Chemical Industries, Ltd.)

Eluate: (n-hexane:2-propanol=90:10)+0.1% trifluoroacetic acid

Flow rate: 0.8 mL/min

Temperature: 40° C.

Detection: UV 230 nm $[\alpha]_D^{27}$ +9.36° (c 1.10, CHCl$_3$)

$^1$H-NMR (400 MHz, DMSO-d$_6$) δ ppm: 1.15 (3H, t) 2.05-2.14 (2H, m) 2.39 (s, 3H) 3.68 (s, 3H) 4.87 (s, 2H) 4.93 (1H, t) 5.59 (s, 2H) 6.54 (1H, dd) 6.57 (1H, d) 6.94 (1H, d) 7.04 (1H, d) 7.20-7.28 (2H, m) 7.33 (1H, dd) 7.41 (1H, dd) 7.48-7.54 (3H, m) 7.65 (1H, d) 7.89-7.94 (2H, m) 8.26 (1H, d) 13.08 (brd, 1H)

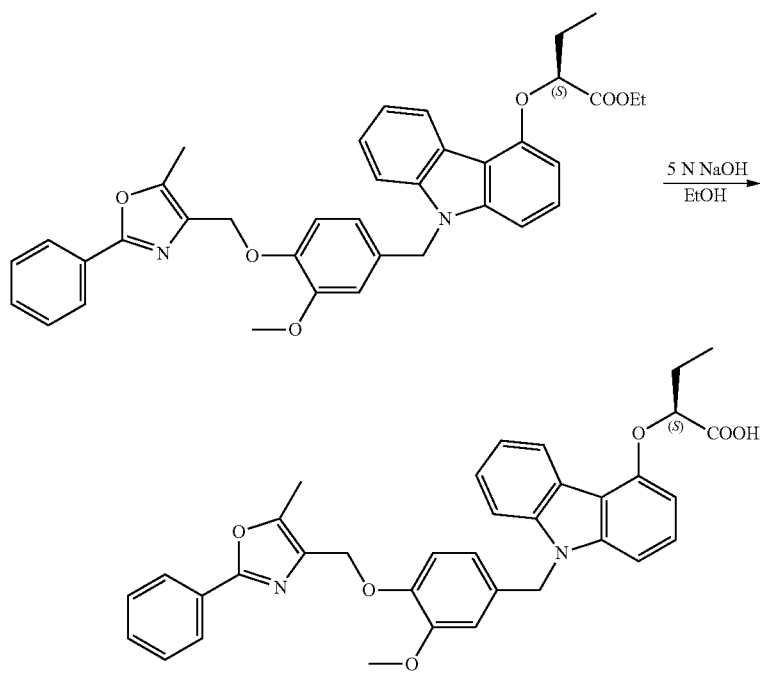

Example 38(e)

Preparation of sodium (S)-(+)-2-{9-[3-methoxy-4-((5-methyl-2-phenyl-oxazole-4-yl)methoxy)-benzyl]-9H-carbazole-4-yloxy}butyrate

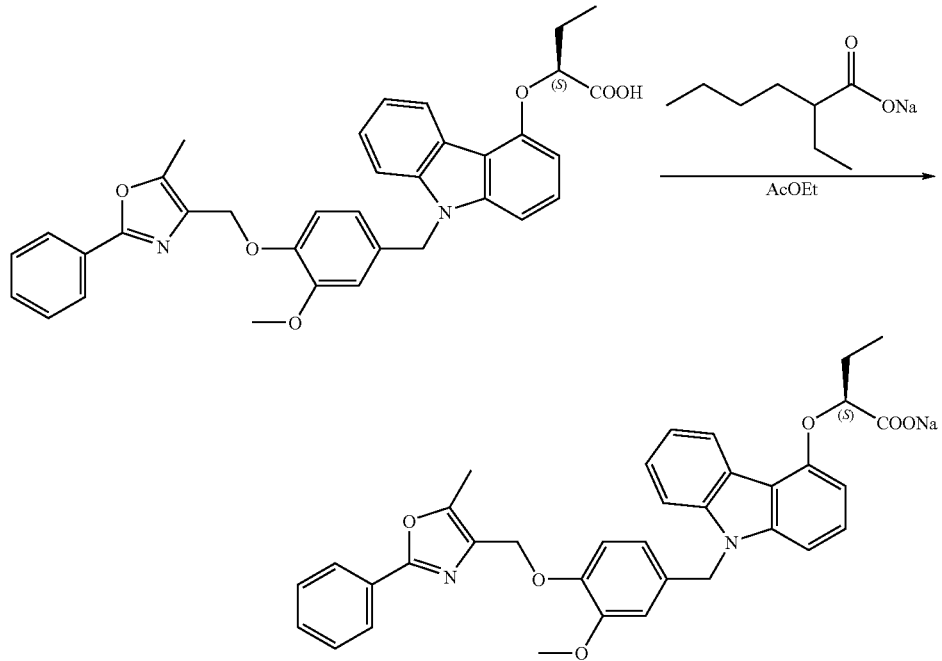

420 mg of (S)-(+)-2-{9-[3-methoxy-4-(5-methyl-2-phenyl-oxazole-4-ylmethoxy)-benzyl]-9H-carbazole-4-yloxy}butyric acid was suspended in 4.2 mL of ethyl acetate, 125 mg of sodium 2-ethylhexanoate was added thereto, and refluxed for 1 hour. After cooling, the crystalline precipitate was isolated by filtration, washed with ethyl acetate, dried under reduced pressure, and 437 mg of the subject compound was prepared as white crystal. Optical purity 96% ee (HPLC).
Column: CHIRALCEL OD-H 0.46×25 cm (Daicel Chemical Industries, Ltd.)
Eluate: (n-hexane:2-propanol=90:10)+0.1% trifluoroacetic acid
Flow rate: 0.8 mL/min
Temperature: 40° C.
Detection: UV 230 nm
$[\alpha]_D^{28}$+14.3° (c 1.00, EtOH)
$^1$H-NMR and MS spectrum data is shown in Table 1.

Example 39

Preparation of sodium (S)-2-{9-[3-methoxy-4-((5-methyl-2-phenyl-oxazole-4-yl)methoxy)-benzyl]-9H-carbazole-4-yloxy}propionate The subject compound was prepared by performing the same operation as those of the examples 38(c) to (e) by using ethyl (R)-2-bromopropionate prepared by the reference 12 instead of ethyl (R)-2-bromobutyrate used in the example 38(c). Optical purity 99% ee (HPLC).
Column: CHIRALCEL OD-H 0.46×25 cm (Daicel Chemical Industries, Ltd.)
Eluate: (n-hexane:2-propanol=80:10)+0.1% trifluoro acetic acid
Flow rate: 0.8 mL/min
Temperature: 40° C.
Detection: UV 230 nm
$^1$H-NMR and MS spectrum data is shown in Table 1.

Example 40

Preparation of sodium (S)-2-{9-[3-methoxy-4-((5-methyl-2-phenyl-oxazole-4-yl)methoxy)-benzyl]-9H-carbazole-4-yloxy}-3-methyl-butyrate

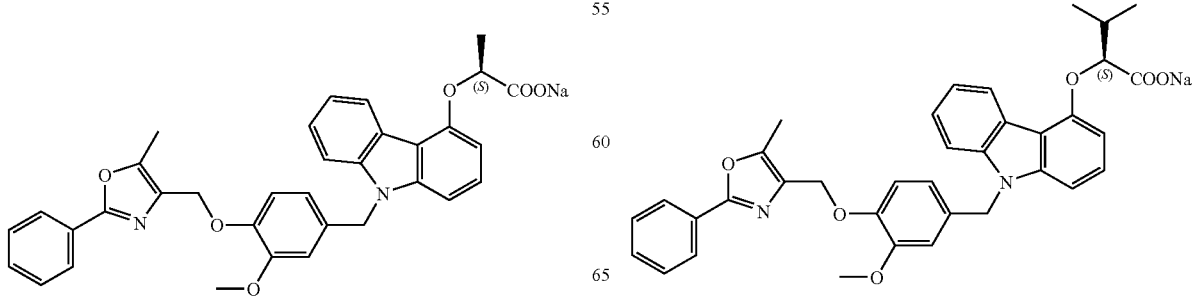

The subject compound was prepared by performing the same operation as those of the examples 38(c) to (e) by using ethyl (R)-2-bromo-3-methylbutyrate prepared by the reference 14 instead of ethyl (R)-2-bromobutyrate used in the example 38(c). Optical purity 94% ee (HPLC).
Column: CHIRALCEL OD-H 0.46×25 cm (Daicel Chemical Industries, Ltd.)
Eluate: (n-hexane:2-propanol=80:10)+0.1% trifluoroacetic acid
Flow rate: 0.8 mL/min
Temperature: 40° C.
Detection: UV 230 nm
$^1$H-NMR and MS spectrum data is shown in Table

Example 41

Preparation of sodium (S)-2-{9-[3-methoxy-4-((5-methyl-2-phenyl-oxazole-4-yl)methoxy)-benzyl]-9H-carbazole-4-yloxy}valerate

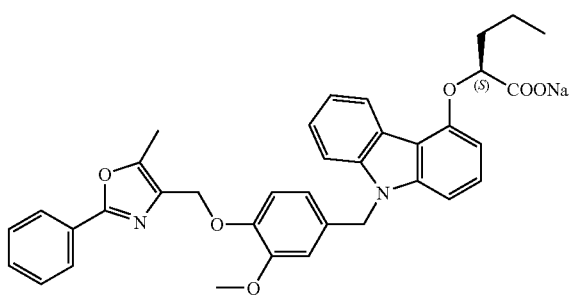

The subject compound was prepared by performing the same operation as those of the examples 38(c) to (e) by using ethyl (R)-2-bromo-valerate prepared by the reference 16 instead of ethyl (R)-2-bromobutyrate used in the example 38(c). Optical purity 97% ee (HPLC).
Column: CHIRALCEL OD-H 0.46×25 cm (Daicel Chemical Industries, Ltd.)
Eluate: (n-hexane:2-propanol=80:10)+0.1% trifluoroacetic acid
Flow rate: 0.8 mL/min
Temperature: 40° C.
Detection: UV 230 nm
$^1$H-NMR and MS spectrum data is shown in Table 1.

Example 42

Preparation of sodium (R)-2-{9-[3-methoxy-4-((5-methyl-2-phenyl-oxazole-4-yl)methoxy)-benzyl]-9H-carbazole-4-yloxy}butyrate

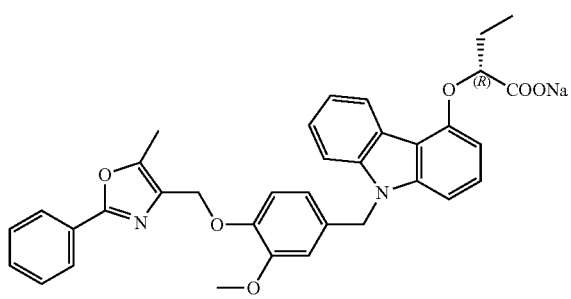

The subject compound was prepared by performing the same operation as those of the examples 38(c) to (e) by using ethyl (S)-2-bromo-butyrate prepared by the reference 11 instead of ethyl (R)-2-bromobutyrate used in the example 38(c). Optical purity>99% ee (HPLC).
$^1$H-NMR and MS spectrum data is shown in Table 1.

Example 43

Preparation of sodium (R)-2-{9-[3-methoxy-4-((5-methyl-2-phenyl-oxazole-4-yl)methoxy)-benzyl]-9H-carbazole-4-yloxy}propionate

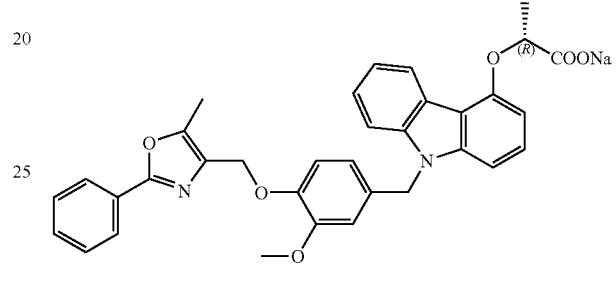

The subject compound was prepared by performing the same operation as those of the examples 38(c) to (e) by using ethyl (S)-2-bromo-propionate prepared by the reference 13 instead of ethyl (R)-2-bromobutyrate used in the example 38(c). Optical purity 98% ee (HPLC).
$^1$H-NMR and MS spectrum data is shown in Table 1.

Example 44

Preparation of sodium (R)-2-{9-[3-methoxy-4-((5-methyl-2-phenyl-oxazole-4-yl)methoxy)-benzyl]-9H-carbazole-4-yloxy}-3-methyl-butyrate

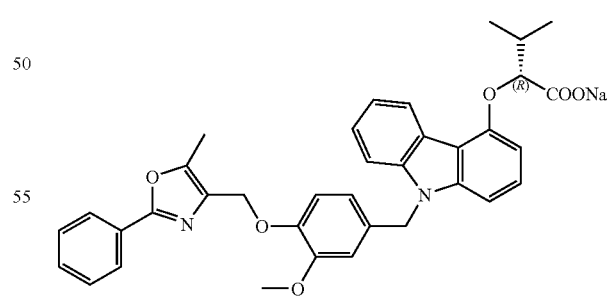

The subject compound was prepared by performing the same operation as those of the examples 38(c) to (e) by using ethyl (S)-2-bromo-3-methylbutyrate prepared by the reference 15 instead of ethyl (R)-2-bromobutyrate used in the example 38(c). Optical purity 98% ee (HPLC).
$^1$H-NMR and MS spectrum data is shown in Table 1.

Example 45

Preparation of sodium (R)-2-{9-[3-methoxy-4-((5-methyl-2-phenyl-oxazole-4-yl)methoxy)-benzyl]-9H-carbazole-4-yloxy}valerate

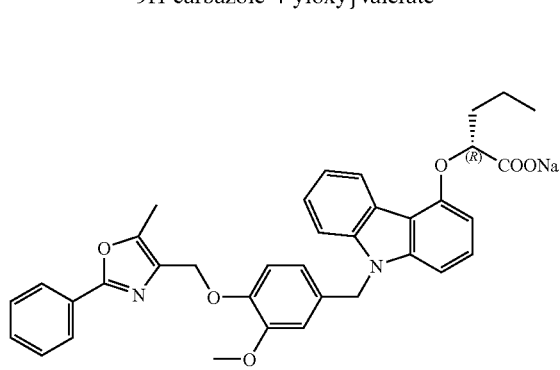

The subject compound was prepared by performing the same operation as those of the examples 38(c) to (e) by using ethyl (S)-2-bromo-valerate prepared by the reference 17 instead of ethyl (R)-2-bromobutyrate used in the example 38(c). Optical purity 97% ee (HPLC).
$^1$H-NMR and MS spectrum data is shown in Table 1.

Example 46

Preparation of sodium 4-((9-(4-((5-methyl-2-phenyloxazole-4-yl)methoxy)-3-methoxybenzyl)-9H-carbazole-5-yloxy)methyl)benzoate

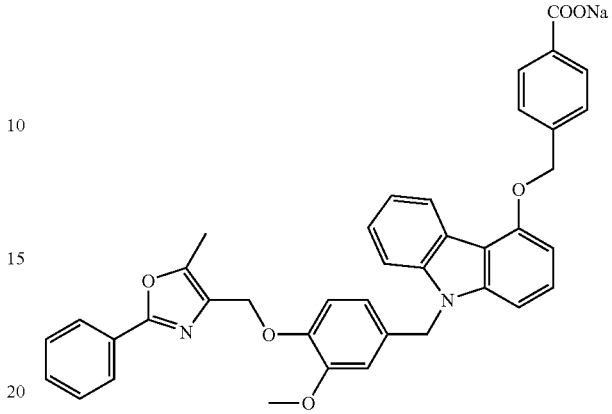

Example 46(a)

Preparation of ethyl 4-((9-(4-((5-methyl-2-phenyloxazole-4-yl)methoxy)-3-methoxy benzyl)-9H-carbazole-5-yloxy)methyl)benzoate

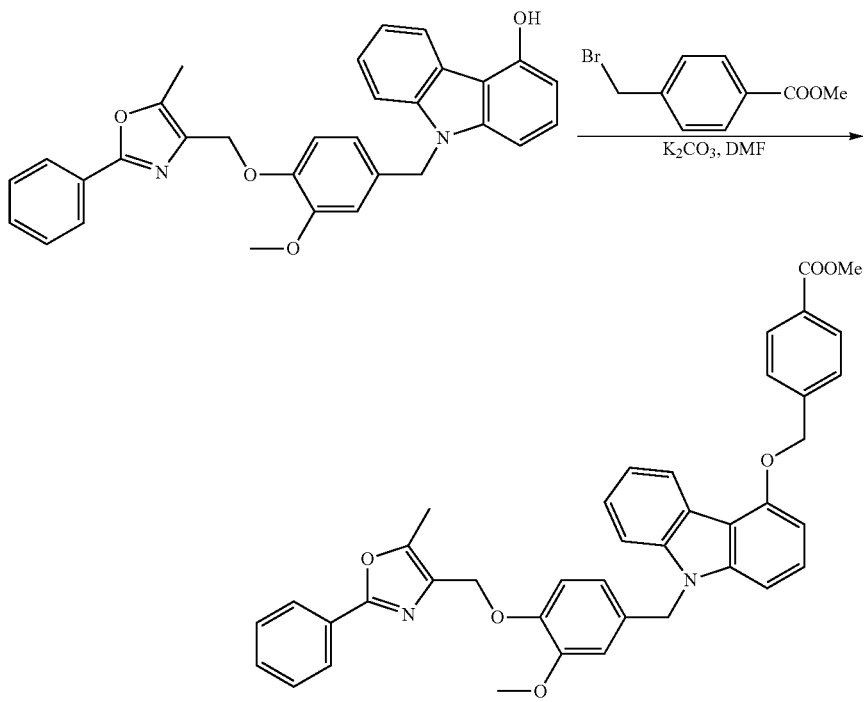

47 mg of methyl 2-bromomethylbenzoate and 27 mg of potassium carbonate (powder) were added to N,N-dimethylformamide (2 mL) solution of 98 mg of 9-{4-[(5-methyl-2-phenyloxazole-4-yl)methoxy]-3-methoxybenzyl}-9H-carbazole-4-o 1, and stirred at 90° C. for 1 hour. After the reaction mixture was allowed to cool, water was added thereto, and then extracted with ethyl acetate. The extract was washed with brine, and dried over anhydrous sodium sulfate. After filtration, the filtrate was concentrated in vacuo, the residue was crystallized from a small amount of ethanol, isolated by filtration with n-hexane, dried under a reduced pressure, and 110 mg of the subject compound was prepared.

¹H-NMR (400 MHz, DMSO-d₆) δ ppm: 2.33 (3H, s) 3.67 (3H, s) 3.87 (3H, s) 4.87 (2H, s) 5.49 (2H, s) 5.57 (2H, s) 6.54 (1H, dd) 6.86 (1H, d) 6.94 (1H, d) 7.04 (1H, d) 7.20 (1H, dd) 7.29 (1H, d) 7.37 (1H, dd) 7.40 (1H, ddd) 7.48-7.53 (3H, m) 7.65 (1H, d) 7.75 (2H, d) 7.88-7.93 (2H, m) 8.05 (2H, d) 8.16 (1H, d)

Example 46(b)

Preparation of sodium 4-((9-(4-((5-methyl-2-phenyloxazole-4-yl)methoxy)-3-methoxybenzyl)-9H-carbazole-5-yloxy)methyl)benzoate

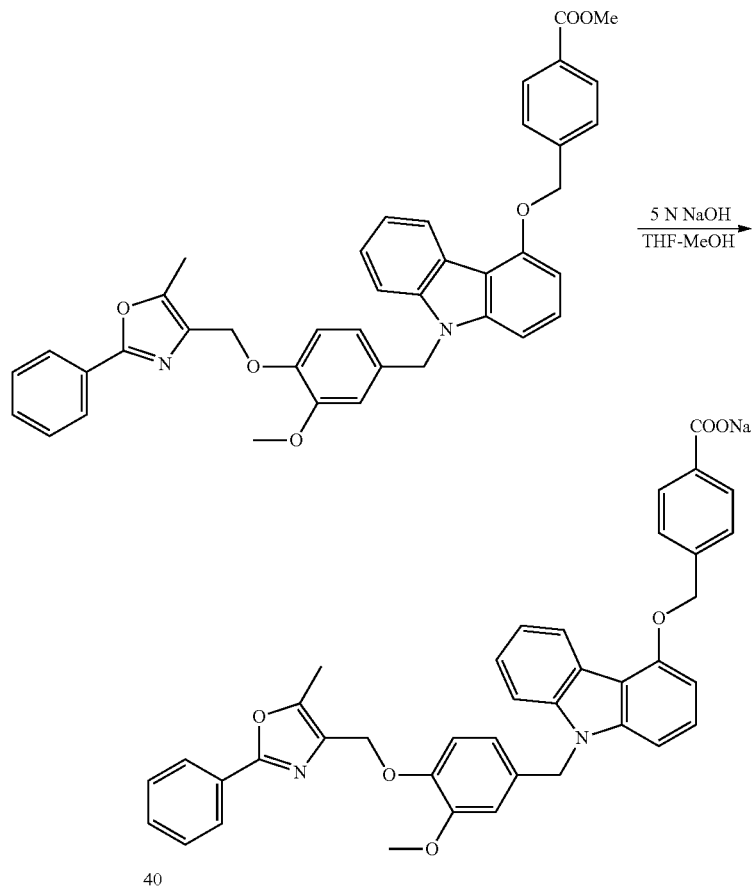

1 mL of 5 N sodium hydroxide solution was added to tetrahydrofuran:methanol=1:1(20 mL) solution of 110 mg of ethyl 4-((9-(4-((5-methyl-2-phenyloxazole-4-yl)methoxy)-3-methoxybenzyl)-9H-carbazole-5-yloxy)methyl)benzoate, and stirred at 70° C. for 1 hour. The reaction mixture was allowed to cool, and the water was added thereto. The crystalline precipitate was isolated by filtration, and washed with 2-propanol. The collected precipitate was dried under reduced pressure, and 107 mg of the subject compound was prepared as white crystal.

¹H-NMR and MS spectrum data is shown in Table 1.

Example 47

Preparation of sodium 2-{9-[3-methoxy-4-((5-methyl-2-phenyloxazole-4-yl)methoxy)-benzyl]-9H-carbazole-4-yloxy}benzoate

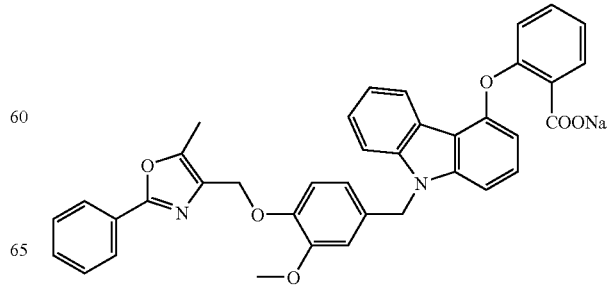

Example 47(a)

Preparation of 2-{9-[3-methoxy-4-((5-methyl-2-phenyloxazole-4-yl)methoxy)-benzyl]-9H-carbazole-4-yloxy}benzoic acid

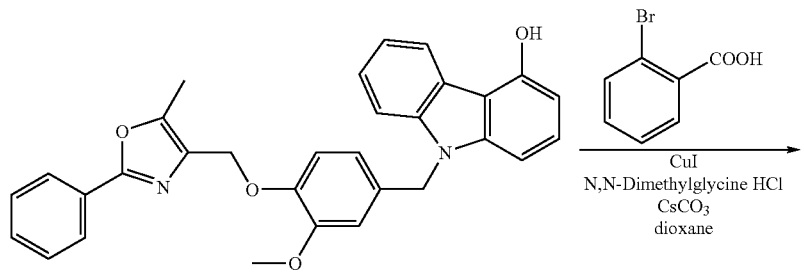

3.53 g of 2-bromobenzoic acid, 2.23 g of copper iodide, 1.63 g of N,N-dimethylglycine hydrochloride, and 15.2 g of cesium carbonate were added to 1,4-dioxane (50 mL) suspension of 5.74 g of 9-{4-[(5-methyl-2-phenyloxazole-4-yl)methoxy]-3-methoxybenzyl}-9H-carbazole-4-ol, and refluxed overnight. 1 N hydrochloric acid was added to the reaction mixture, extracted with ethyl acetate, and washed with brine. The extract was dried over anhydrous sodium sulfate. After filtration, the filtrate was concentrated in vacuo, the residue was purified by silica gel chromatography (ethyl acetate:n-hexane=2:1), and 1.4 g of the subject compound was prepared as white crystal.

$^1$H-NMR (400 MHz, DMSO-$d_6$) δ ppm: 2.38 (3H, s) 3.69 (3H, s) 4.88 (2H, s) 5.62 (2H, s) 6.57 (1H, d) 6.61 (1H, dd) 6.97 (2H, d) 7.07 (1H, d) 7.15 (1H, dd) 7.26 (1H, ddd) 7.37-7.54 (7H, m) 7.69 (1H, d) 7.88-7.93 (3H, m) 8.09 (1H, d) 12.91 (1H, s)

Example 47(b)

Preparation of sodium 2-{9-[3-methoxy-4-((5-methyl-2-phenyloxazole-4-yl)methoxy)-benzyl]-9H-carbazole-4-yloxy}benzoate

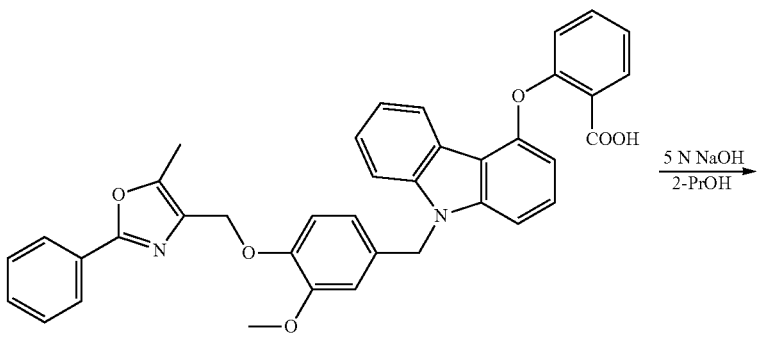

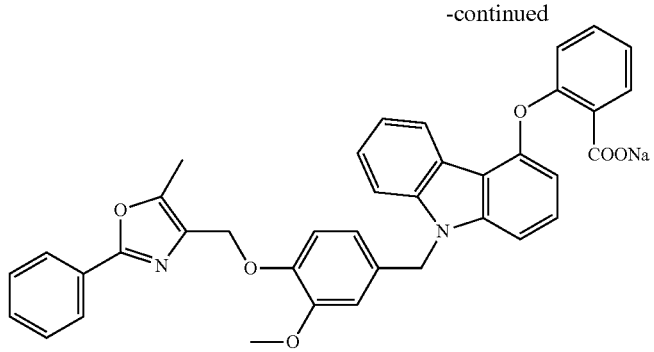

260 μl of 5 N sodium hydroxide solution was added to 2-propanol suspension of 395 mg of 2-{9-[3-methoxy-4-((5-methyl-2-phenyloxazole-4-yl)methoxy)-benzyl]-9H-carbazole-yloxy-benzoic acid, and was dissolved by heating. The insoluble was filtered off, and the filtrate was concentrated in vacuo. The residue was crystallized from ethanol, isolated by filtration with n-hexane, and dried under reduced pressure, and 395 mg of the subject compound was prepared as white crystal.

¹H-NMR and MS spectrum data is shown in Table 1.

Example 48

Preparation of sodium 3-{9-[3-methoxy-4-((5-methyl-2-phenyloxazole-4-yl)methoxy)-benzyl]-9H-carbazole-4-yloxy}benzoate

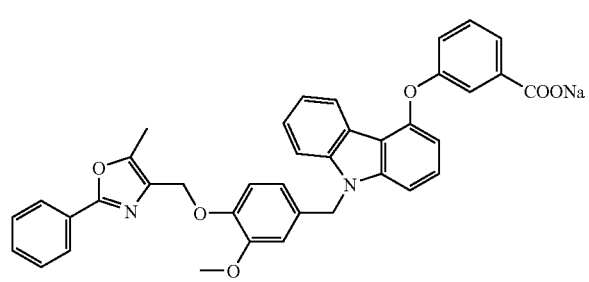

The subject compound was prepared by performing the same operation as those of the examples 47(a) to 47(b) by using 3-bromobenzoic acid instead of 2-bromobenzoic acid used in the example 47(a).

¹H-NMR and MS spectrum data is shown in Table 1.

Example 49

Preparation of sodium 4-{9-[3-methoxy-4-((5-methyl-2-phenyloxazole-4-yl)methoxy)-benzyl]-9H-carbazole-4-yloxy}benzoate

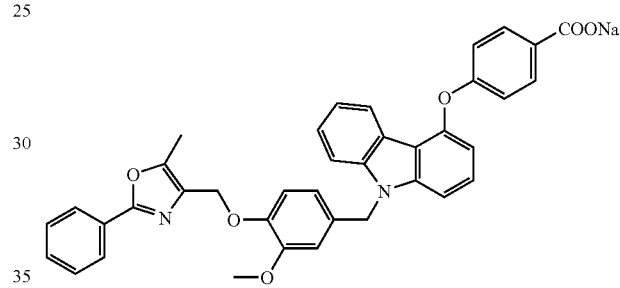

The subject compound was prepared by performing the same operation as those of the examples 47(a) to 47(b) by using 4-bromobenzoic acid instead of 2-bromobenzoic acid used in the example 47(a).

¹H-NMR and MS spectrum data is shown in Table 1.

Example 50

Preparation of sodium (+)-2-{9-[3-methoxy-4-((5-methyl-2-phenyl-oxazole-4-yl)methoxy)-benzyl]-9H-carbazole-4-yloxy}-2-phenylacetate

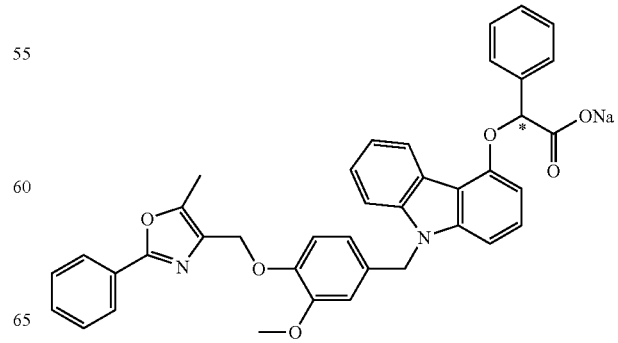

Example 50(a)

Preparation of sodium (±)-2-{9-[3-methoxy-4-((5-methyl-2-phenyl-oxazole-4-yl)methoxy)-benzyl]-9H-carbazole-4-yloxy}-2-phenylacetate

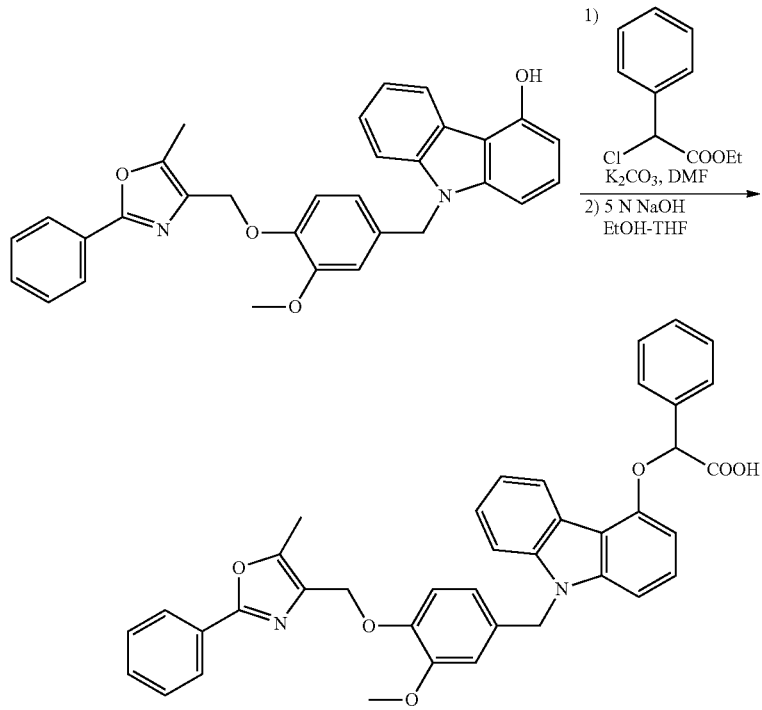

5.26 g of ethyl α-bromophenylacetate and 4.23 g of potassium carbonate (powder) were added to N,N-dimethylformamide (50 mL) suspension of 10.0 g of 9-{4-[(5-methyl-2-phenyloxazole-4-yl)methoxy]-3-methoxybenzyl}-9H-carbazole-4-ol, and stirred at 60° C. for 2 hours. After the reaction mixture was allowed to cool, water and ethanol were added, the crystalline precipitate was isolated by filtration, and 24 g of ethyl (±)-2-{9-[3-methoxy-4-((5-methyl-2-phenyl-oxazole-4-yl)methoxy)-benzyl]-9H-carbazole-4-yloxy}-2-phenylacetate (undried) was prepared. This was dissolved in mixture of ethanol-tetrahydrofuran, 4.1 mL of 5 N sodium hydroxide solution was added and stirred at 60° C. for 1 hour. The reaction mixture was allowed to cool, and then adjusted to pH3 with 1 N hydrochloric acid, the crystalline precipitate was isolated by filtration, washed with ethyl acetate, dried under reduced pressure, and 10.6 g of the subject compound was prepared as white crystal.

$^1$H-NMR (400 MHz, DMSO-$d_6$) δ ppm: 2.37 (3H, s) 3.67 (3H, s) 4.86 (2H, d) 5.56 (2H, s) 6.11 (1H, s) 6.54 (1H, dd) 6.70 (1H, d) 6.94 (1H, d) 7.03 (1H, d) 7.20-7.35 (3H, m) 7.39-7.55 (7H, m) 7.65 (1H, d) 7.70-7.75 (2H, m) 7.88-7.97 (2H, d) 8.37 (1H, d) 13.30 (1H, br)

Example 50(b)

Preparation of 3-(2-(9-(4-((5-methyl-2-phenyloxazole-4-yl)methoxy)-3-methoxybenzyl)-9H-carbazole-4-yloxy)-2-phenylacetyl)-4-(S)-benzyloxazolidine-2-one

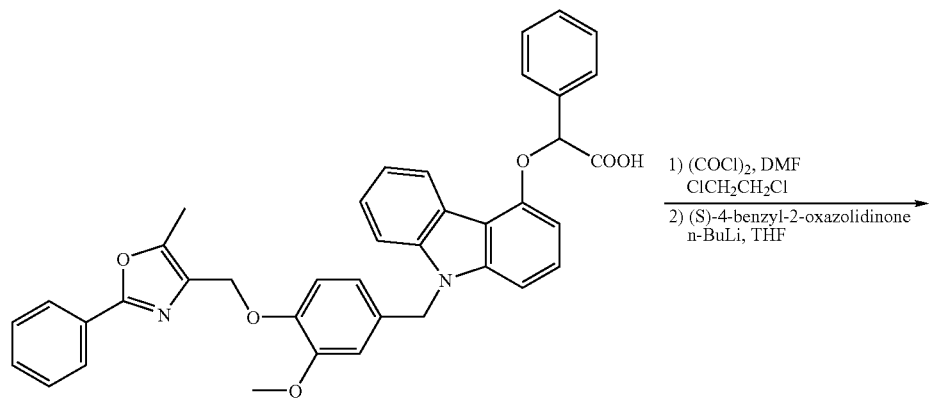

-continued

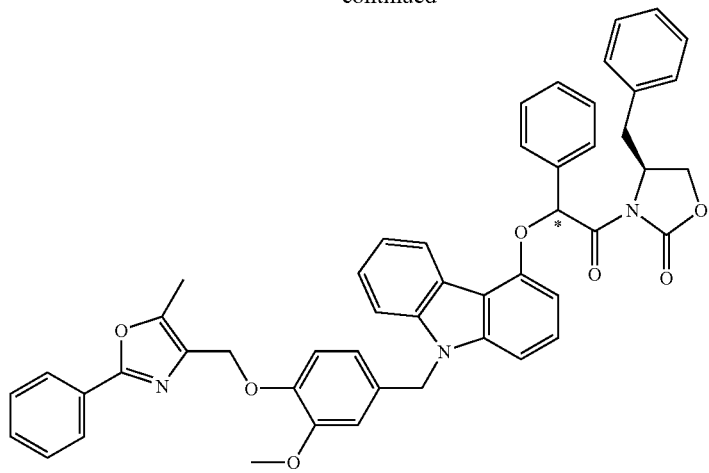

2.3 mL of oxalyl chloride was added to 1,2-dichloroethane (100 mL) solution of 10.6 g of 2-{9-[3-methoxy-4-(5-methyl-2-phenyl-oxazole-4-ylmethoxy)-benzyl]-9H-carbazole-4-yloxy}-2-phenylacetic acid, then 5 drops of N,N-dimethylformamide were added, and stirred at room temperature for 1 hour. The reaction mixture was concentrated in vacuo, and {9-[3-methoxy-4-(5-methyl-2-phenyl-oxazole-4-ylmethoxy)-benzyl]-9H-carbazole-4-yloxy}phenylacetyl chloride was prepared.

9.1 mL of 2.44M n-butyllithium tetrahydrofuran solution was added thereto dropwise to tetrahydrofuran (30 mL) solution of 3.92 g of (S)-4-benzyl-2-oxazolidinone at −50° C. The mixture was stirred at −50° C. for 1 hour. Thereafter, the solution of the previously prepared (±)-{9-[3-methoxy-4-(5-methyl-2-phenyl-oxazole-4-ylmethoxy)-benzyl]-9H-carbazole-4-yloxy}phenylacetyl chloride in tetrahydrofuran (30 mL) was added thereto dropwise at −50° C. After the dropwise addition thereto, the mixture was stirred at room temperature overnight. Water was added to the reaction mixture, and extracted with ethyl acetate. The extract was washed with brine, and dried over anhydrous sodium sulfate. After filtration, the filtrate was concentrated in vacuo, the prepared diastereomer mixture was purified by medium-pressure silica gel chromatography (ethyl acetate:n-hexane=5:1), and two types of the subject compound, 1.52 g of compound A (first fraction) and 1.2 g compound B (second fraction), were respectively prepared as pale brown powder.

Compound A $^1$H-NMR (400 MHz, DMSO-$d_6$) δ ppm: 2.35 (3H, s) 3.03 (2H, d) 3.66 (3H, s) 4.28 (1H, dd) 4.36 (1H, dd) 4.67-4.73 (1H, m) 4.86 (2H, s) 5.58 (2H, s) 6.57 (1H, dd) 6.74 (1H, d) 6.93 (1H, d) 7.04 (1H, d) 7.17-7.32 (7H, m) 7.34 (1H, d) 7.39-7.54 (1H, m) 7.67 (1H, d) 7.70-7.74 (2H, m) 7.87-7.93 (2H, m) 8.27 (1H, d)

Compound B $^1$H-NMR (400 MHz, DMSO-$d_6$) δ ppm: 2.36 (3H, s) 2.76-2.87 (2H, m) 3.67 (3H, s) 4.20 (1H, dd) 4.47 (1H, dd) 4.81-4.88 (3H, m) 5.56 (2H, s) 6.54 (1H, dd) 6.67-6.74 (3H, m) 6.94 (1H, d) 7.01-7.08 (3H, m) 7.15 (1H, dd) 7.20-7.36 (4H, m) 7.39-7.46 (1H, m) 7.48-7.60 (6H, m) 7.65 (1H, m) 7.79-7.84 (2H, m) 7.88-7.94 (2H, m) 8.37 (1H, d)

Example 50(c)

Preparation of (+)-2-{9-[3-methoxy-4-((5-methyl-2-phenyl-oxazole-4-yl)methoxy)-benzyl]-9H-carbazole-4-yloxy}-2-phenylacetic acid

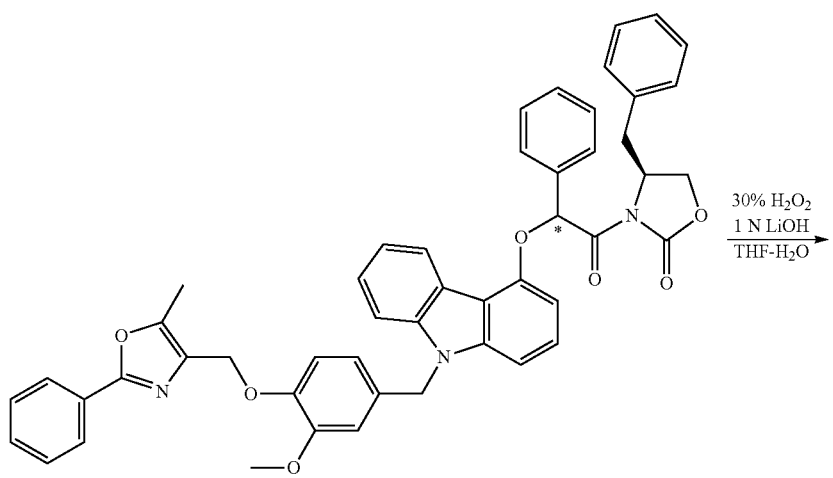

-continued

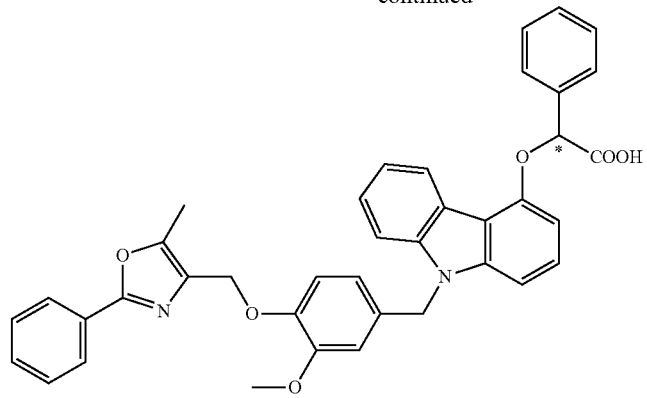

880 mg of 30% hydrogen peroxide solution was added to the solution of 1.52 g of compound A (3-(2-(9-(4-((5-methyl-2-phenyloxazole-4-yl)methoxy)-3-methoxybenzyl)-9H-carbazole-4-yloxy)-2-phenylacetyl)-4-(S)-benzyloxazolidine-2-one) in tetrahydrofuran:water=4:1 (50 mL) while being cooled in an ice bath, and then 1.94 mL of 1M lithium hydroxide solution was added thereto dropwise. After stirring at room temperature for 1 hour, 1M sodium sulfite solution was added to reaction mixture. Thereafter, the pH was adjusted to pH3 with 1 N hydrochloric acid, and extracted with ethyl acetate. The extract was washed with brine, and dried over anhydrous sodium sulfate. After filtration, the filtrate was concentrated in vacuo, the residue was purified by silica gel chromatography (ethyl acetate:n-hexane=5:1), and 980 mg of (+)-2-{9-[3-methoxy-4-((5-methyl-2-phenyl-oxazole-4-yl)methoxy)-benzyl]-9H-carbazole-4-yloxy}-2-phenylacetic acid was prepared as pale brown powder.

Example 50(d)

Preparation of sodium (+)-2-{9-[3-methoxy-4-((5-methyl-2-phenyl-oxazole-4-yl)methoxy)-benzyl]-9H-carbazole-4-yloxy}-2-phenylacetate

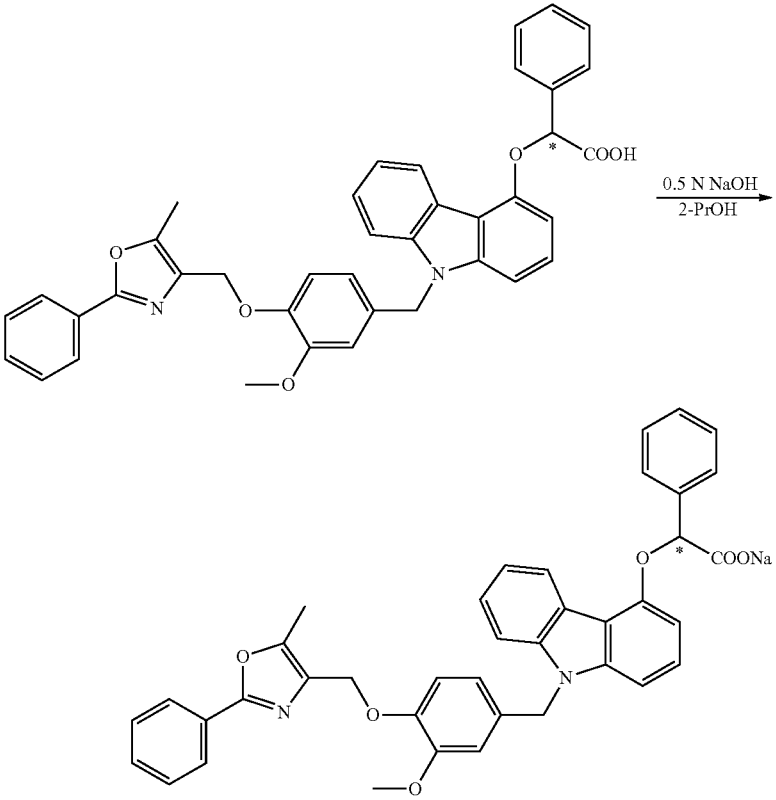

0.5 N sodium hydroxide solution (3.1 mL) was added to the solution of 980 mg of (+)-2-{9-[3-methoxy-4-((5-methyl-2-phenyl-oxazole-4-yl)methoxy)-benzyl]-9H-carbazole-4-yloxy}-2-phenylacetic acid in 2-propanol (30 mL). 2-propanol was removed under reduced pressure, the residue was collected by filtration with a small amount of 2-propanol, and 850 mg of the subject compound was prepared as pale brown powder. Optical purity>99% ee (HPLC)

Column: CHIRALPAK AD-H 0.46×15 cm (Daicel Chemical Industries, Ltd.)

Eluate: (n-hexane:2-propanol=80:20)+0.1% trifluoroacetic acid

Flow rate: 0.8 mL/min

Temperature: 40° C.

Detection: UV 230 nm $[\alpha]_D^{27}$+31.8° (c 1.02, MeOH)

$^1$H-NMR and MS spectrum data is shown in Table 1.

Example 51

Preparation of sodium (−)-2-{9-[3-methoxy-4-((5-methyl-2-phenyl-oxazole-4-yl)methoxy)-benzyl]-9H-carbazole-4-yloxy}-2-phenylacetate

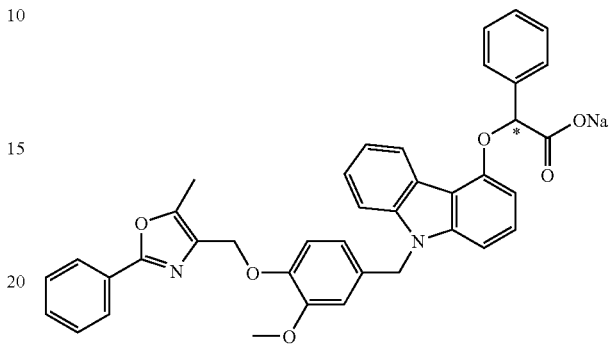

Example 51(a)

Preparation of (−)-2-{9-[3-methoxy-4-((5-methyl-2-phenyl-oxazole-4-yl)methoxy)-benzyl]-9H-carbazole-4-yloxy}-2-phenylacetic acid

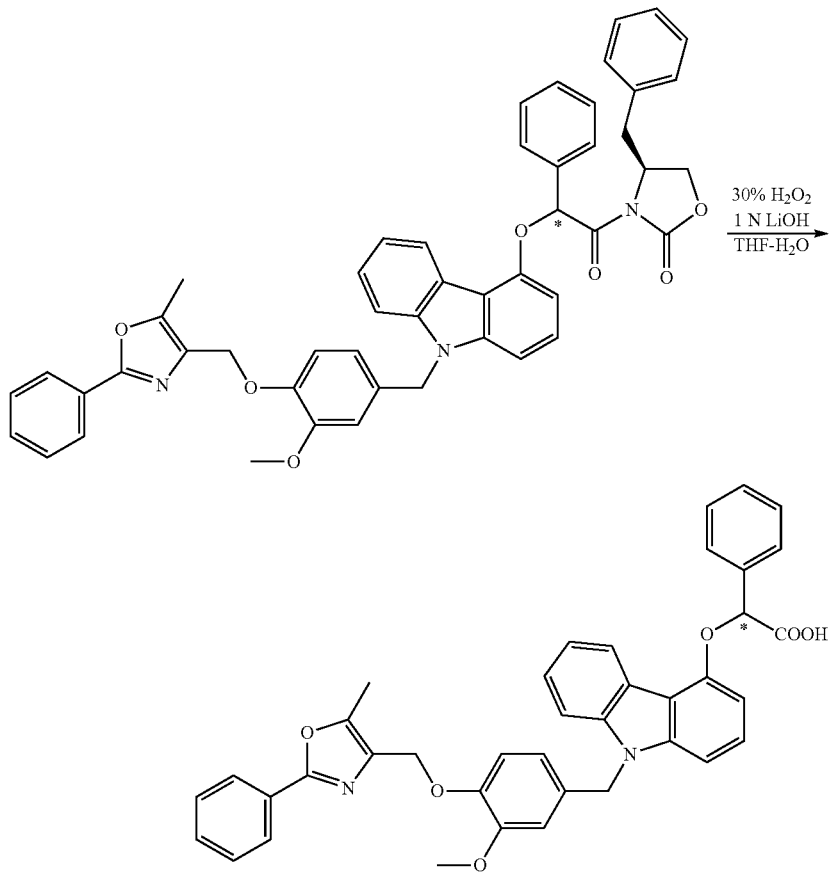

The same operation as that of the example 50(c) was carried out by using 1.2 g of the compound (3-(2-(9-(4-((5-methyl-2-phenyloxazole-4-yl)methoxy)-3-methoxybenzyl)-9H-carbazole-4-yloxy)-2-phenylacetyl)-4-(S)-benzyl-oxazolidine-2-one) prepared by the example 50(b) and 750 mg of (−)-2-{9-[3-methoxy-4-((5-methyl-2-phenyl-oxazole-4-yl)methoxy)-benzyl]-9H-carbazole-4-yloxy}-2-phenylacetic acid was prepared as pale brown powder.

Example 51(b)

Preparation of sodium (−)-2-{9-[3-methoxy-4-((5-methyl-2-phenyl-oxazole-4-yl)methoxy)-benzyl]-9H-carbazole-4-yloxy}-2-phenylacetate

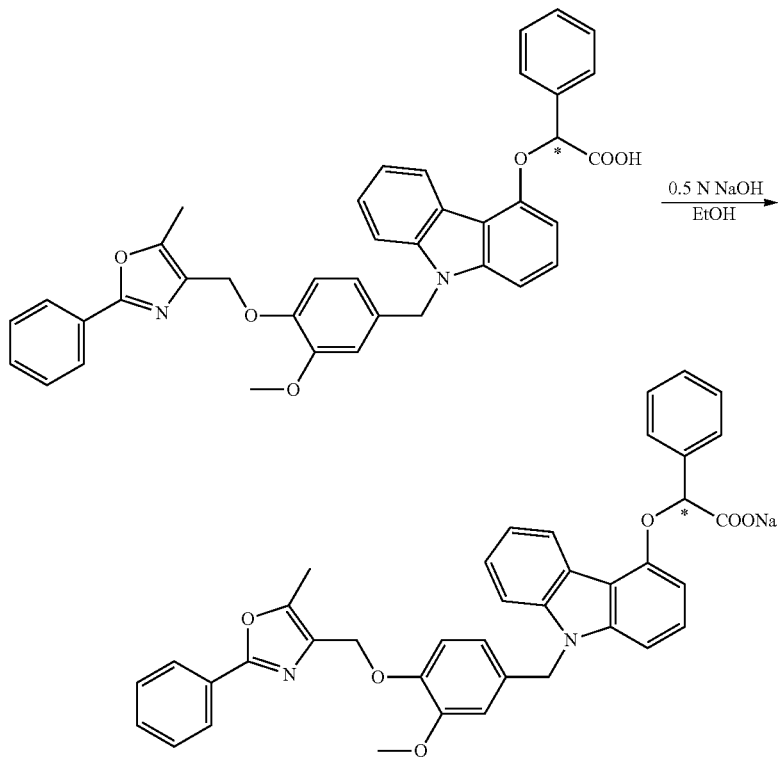

The same operation as that of the example 50(d) was carried out by using 750 mg of (−)-2-{9-[3-methoxy-4-((5-methyl-2-phenyl-oxazole-4-yl)methoxy)-benzyl]-9H-carbazole-4-yloxy}-2-phenylacetic acid and 750 mg of the subject compound was prepared as pale brown powder. Optical purity 98% ee (HPLC)
Column: CHIRALPAK AD-H 0.46×15 cm (Daicel Chemical Industries, Ltd.)
Eluate: (n-hexane:2-propanol=80:20)+0.1% trifluoroacetic acid
Flow rate: 0.8 mL/min
Temperature: 40° C.
Detection: UV 230 nm
$[\alpha]_D^{27}$ −35.1° (c 1.03, MeOH)
$^1$H-NMR and MS spectrum data is shown in Table 1.

Example 52

Preparation of sodium (−)-4-{9-[3-methoxy-4-((5-methyl-2-phenyl-oxazole-4-yl)methoxy)-benzyl]-9H-carbazole-4-yloxy}-2-methyl-butyrate

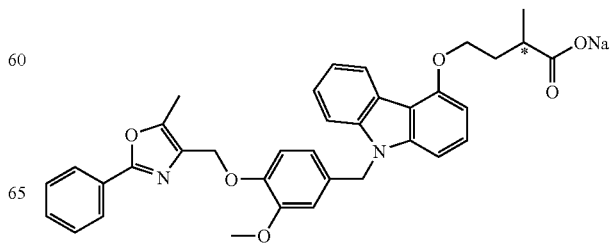

Example 52(a)

Preparation of (S)-3-(4-(9-(4-((5-methyl-2-phenyloxazole-4-yl)methoxy)-3-methoxy benzyl)-9H-carbazole-4-yloxy)-2-methoxybutanoyl)-4-benzyloxazolidine-2-one

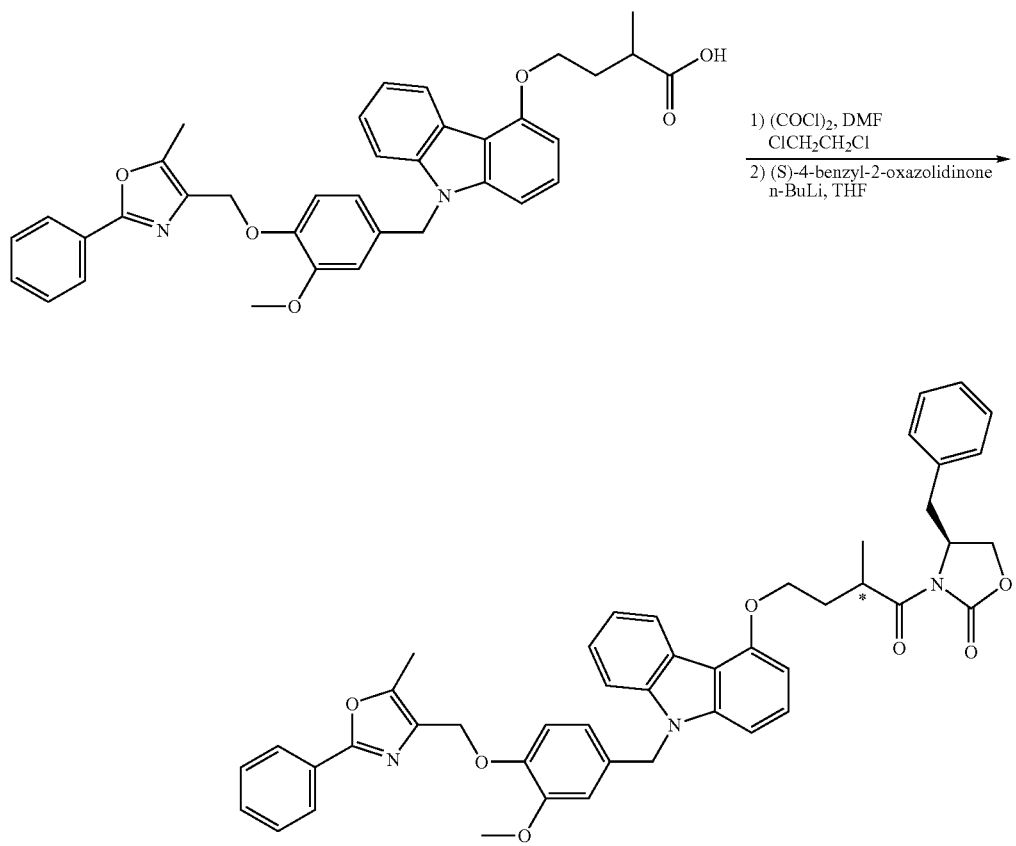

2.2 mL of oxalyl chloride was added to the solution of 10.0 g of (±)-4-{9-[3-methoxy-4-((5-methyl-2-phenyloxazole-4-yl)methoxy)-benzyl]-9H-carbazole-4-yloxy}-2-methyl-butyric acid prepared by the example 27 in 1,2-dichloroethane (100 mL), and then 5 drops of N,N-dimethylformamide was added thereto, and stirred at room temperature for 1 hour. The reaction mixture was vacuum concentrated, and (±)-4-(9-(4-((5-methyl-2-phenyloxazole-4-yl)methoxy)-3-methoxybenzyl)-9H-carbazole-4-yloxy)-2-methylbutanoyl chloride was prepared.

9.1 mL of 2.44M n-butyllithium tetrahydrofuran solution was added thereto dropwise into the solution of 3.59 g of (S)-4-benzyl-2-oxazolidinone in tetrahydrofuran (50 mL) at −50° C. The solution was stirred at −50° C. for 1 hour. Thereafter, the solution of the previously prepared (±)-4-(9-(4-((5-methyl-2-phenyloxazole-4-yl)methoxy)-3-methoxybenzyl)-9H-carbazole-4-yloxy)-2-methylbutanoyl chloride in tetrahydrofuran (50 mL) was added thereto dropwise at −50° C. After the dropwise addition thereto, the mixture was stirred at room temperature overnight. Water was added to the reaction mixture, and extracted with ethyl acetate. The extract was washed with brine, and dried over anhydrous sodium sulfate. After filtration, the filtrate was concentrated in vacuo, and diastereomer mixture was prepared as crystal. The crystal was isolated by filtration with ethyl acetate-n-hexane, and 3.19 g of the subject compound (compound A) of single diastereomer (less polar) was prepared. The filtrate was concentrated in vacuo, the concentrated residue was purified by medium-pressure silica gel chromatography (ethyl acetate:n-hexane=5:1), and 3.3 g of the subject compound (compound B) of the other diastereomer (polar) was prepared as powder.

Example 52(b)

Preparation of optically active 4-{9-[3-methoxy-4-((5-methyl-2-phenyl-oxazole-4-yl)methoxy)-benzyl]-9H-carbazole-4-yloxy}-2-methyl-butyric acid

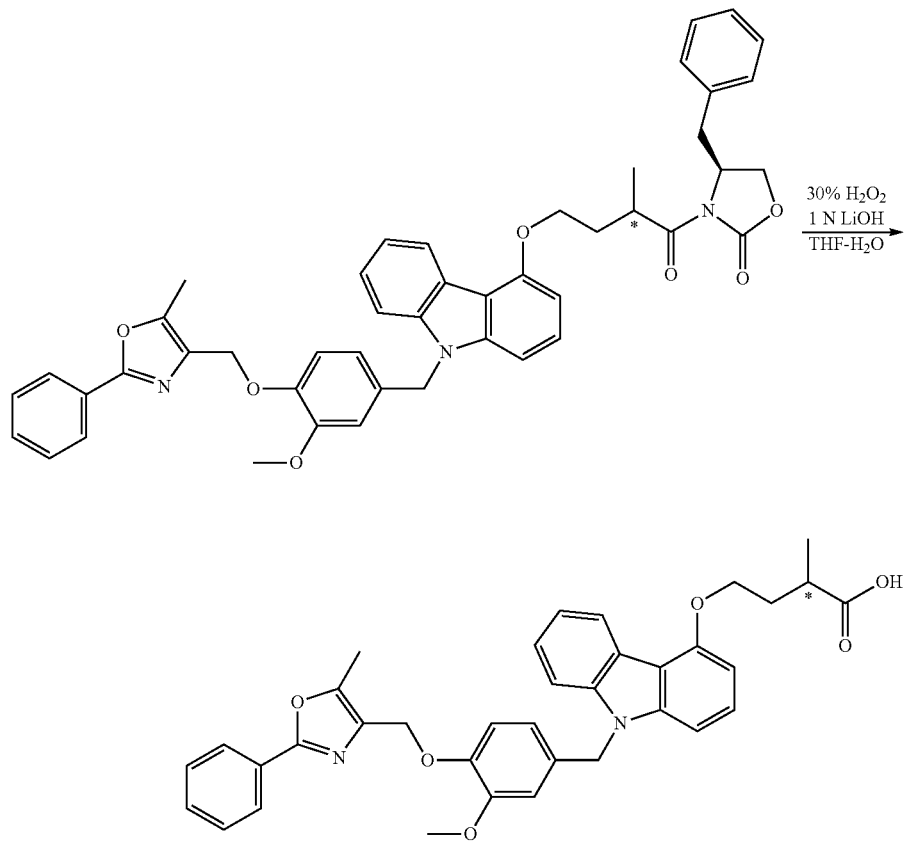

1.81 g of 30% hydrogen peroxide solution was added to the solution (75 mL) of 3.00 g of (S)-3-(4-(9-(4-((5-methyl-2-phenyloxazole-4-yl)methoxy)-3-methoxybenzyl)-9H-carbazole-4-yloxy)-2-methoxybutanoyl)-4-benzyloxazolidine-2-one (compound B) prepared by the example 52(a) in tetrahydrofuran:water=4:1 at −5° C., and then 6.4 mL of 1M lithium hydroxide solution was added thereto dropwise. After the dropwise addition thereto, the solution was stirred for 30 minutes, and 1M sodium sulfite solution was added to the reaction mixture. Thereafter, the pH was adjusted to pH3 with 1 N hydrochloric acid, and extracted with ethyl acetate. The extract was washed with brine, and dried over anhydrous sodium sulfate. After filtration, the filtrate was concentrated in vacuo, the residue was crystallized from ethyl acetate, filtered off with diisopropylether, and 2.1 g of the optically active 4-{9-[3-methoxy-4-(5-methyl-2-phenyl-oxazole-4-ylmethoxy)-benzyl]-9H-carbazole-4-yloxy}-2-methyl-butyric acid was prepared as white crystal.

Example 52(c)

Preparation of sodium (+)-4-{9-[3-methoxy-4-((5-methyl-2-phenyl-oxazole-4-yl)methoxy)-benzyl]-9H-carbazole-4-yloxy}-2-methyl-butyrate

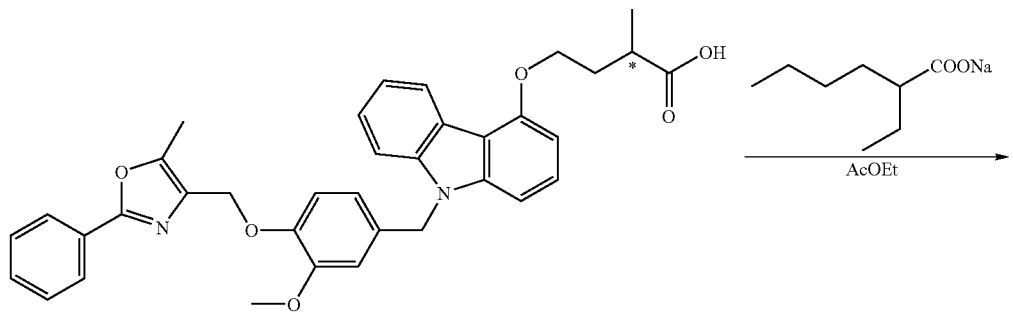

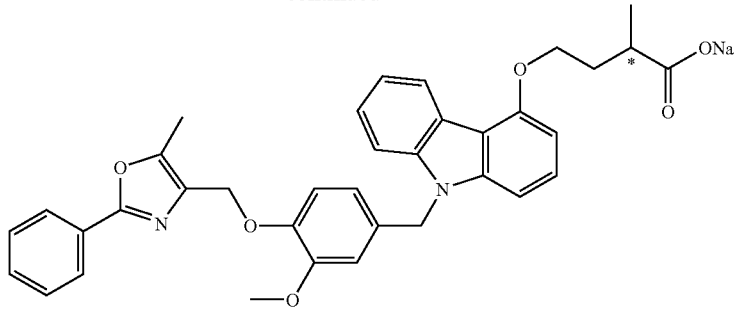

Sodium 2-ethylhexanoate (479 mg) was added to the solution of 1.5 g of 4-{9-[3-methoxy-4-((5-methyl-2-phenyl-oxazole-4-yl)methoxy)-benzyl]-9H-carbazole-4-yloxy}-2-methyl-butyric acid prepared by the example 52(b) in ethyl acetate (15 mL) at room temperature. After stirring at room temperature for 30 minutes, the precipitate was isolated by filtration, washed with ethanol, dried under reduced pressure, and 1.49 g of the subject compound was prepared as white powder. Optical purity>99% ee (HPLC)

Column: CHIRALPAK AD-H 0.46×15 cm (Daicel Chemical Industries, Ltd.)

Eluate: (n-hexane:2-propanol=80:20)+0.1% trifluoroacetic acid

Flow rate: 0.8 mL/min

Temperature: 40° C.

Detection: UV 230 nm $[\alpha]_D^{25}$ −16.2° (c 0.45, MeOH)

$^1$H-NMR and MS spectrum data is shown in Table 1.

Example 53

Preparation of sodium (+)-4-{9-[3-methoxy-4-((5-methyl-2-phenyl-oxazole-4-yl)methoxy)-benzyl]-9H-carbazole-4-yloxy}-2-methyl-butyrate

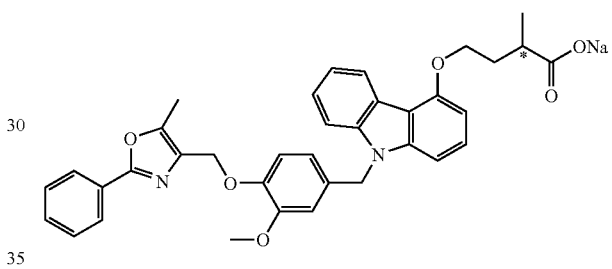

Example 53(a)

Preparation of optically active 4-{9-[3-methoxy-4-((5-methyl-2-phenyl-oxazole-4-yl)methoxy)-benzyl]-9H-carbazole-4-yloxy}-2-methyl-butyric acid

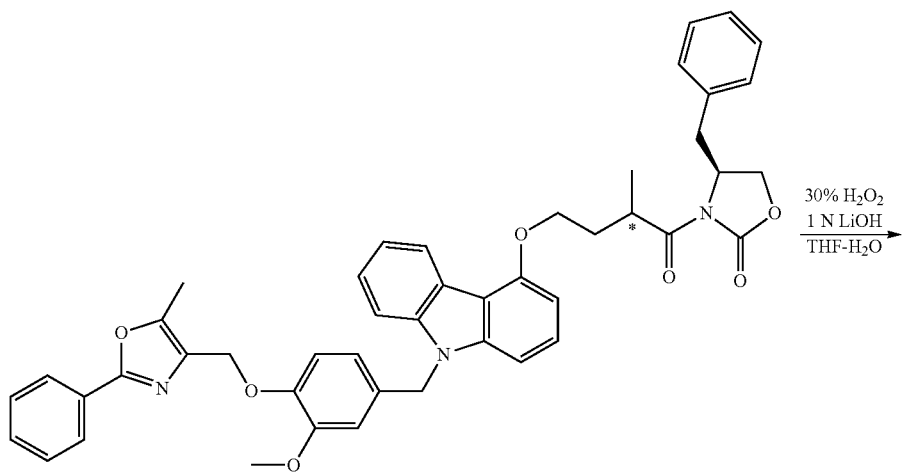

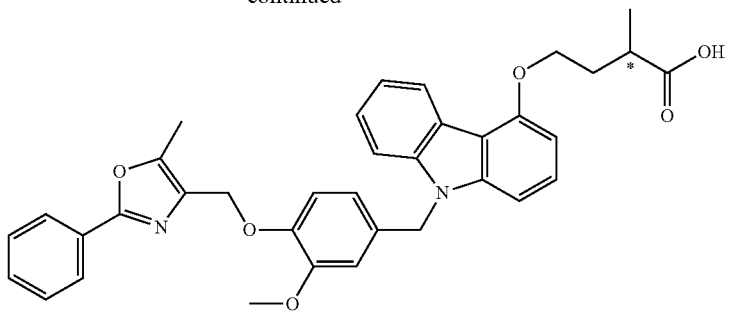

The same operation as that of the example 52(b) was carried out by using 2.95 g of (S)-3-(4-(9-(4-((5-methyl-2-phenyloxazole-4-yl)methoxy)-3-methoxybenzyl)-9H-carbazole-4-yloxy)-2-methoxybutanoyl)-4-benzyloxazolidine-2-one (compound A) prepared by the example 52(a), and 1.6 g of optically active 4-{9-[3-methoxy-4-((5-methyl-2-phenyl-oxazole-4-yl)methoxy)-benzyl]-9H-carbazole-4-yloxy}-2-methyl-butyric acid was prepared as white crystal.

Example 53(b)

Preparation of sodium (+)-4-{9-[3-methoxy-4-((5-methyl-2-phenyl-oxazole-4-yl)methoxy)-benzyl]-9H-carbazole-4-yloxy}-2-methyl-butyrate

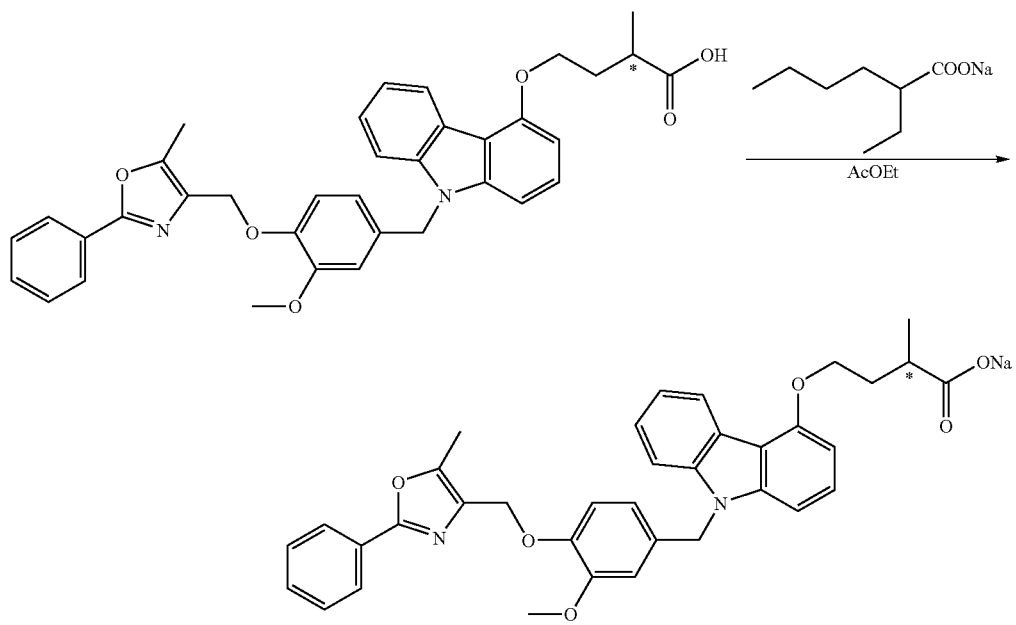

The same operation as that of the example 52(c) was carried out by using 1.5 g of 4-{9-[3-methoxy-4-((5-methyl-2-phenyl-oxazole-4-yl)methoxy)-benzyl]-9H-carbazole-4-yloxy}-2-methyl-butyric acid prepared by the example 53(a), and 1.36 g of the subject compound was prepared as white powder. Optical purity 98% ee (HPLC)

Column: CHIRALPAK AD-H 0.46×15 cm (Daicel Chemical Industries, Ltd.)

Eluate: (n-hexane:2-propanol=80:20)+0.1% trifluoroacetic acid

Flow rate: 0.8 mL/min

Temperature: 40° C.

Detection: UV 230 nm $[\alpha]_D^{23}$ +12.9° (c 0.41, MeOH)

$^1$H-NMR and MS spectrum data is shown in Table 1.

TABLE 1

Structure and properties of compounds of examples

| Example | Structure | Steric | ¹H-NMR (400 MHz) | MS (FAB) m/z: | Aspect |
|---|---|---|---|---|---|
| 1 | 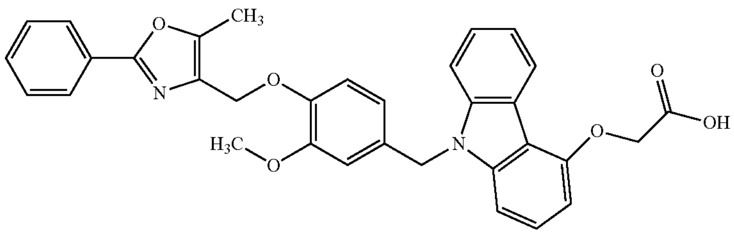 | | DMSO-d₆: 2.37 (3H, s) 3.67 (3H, s) 4.87 (2H, d) 4.92 (2H, s) 5.57 (2H, s) 6.53 (1H, dd) 6.68 (1H, d) 6.94 (1H, d) 7.03 (1H, d) 7.21 (1H, dd) 7.25 (1H, d) 7.34 (1H, d) 7.41 (1H, ddd) 7.47-7.55 (3H, m) 7.63 (1H, d) 7.88-7.96 (2H, m) 8.34 (1H, d) 13.09 (1H, br) | 549 (M + H)⁺ | pale yellow crystal |
| 2 | 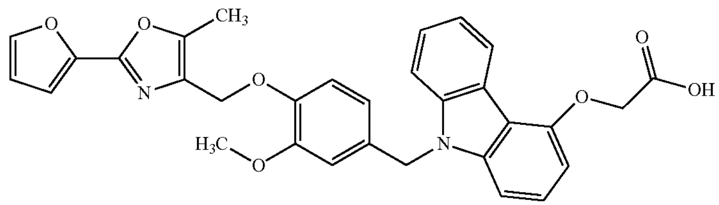 | | DMSO-d₆: 2.34 (3H, s) 3.67 (3H, s) 4.84 (2H, s) 4.92 (2H, s) 5.57 (2H, s) 6.53 (1H, dd) 6.60-6.70 (2H, m) 6.92 (1H, d) 7.02 (1H, d) 7.07 (1H, d) 7.22 (1H, dd) 7.28 (1H, d) 7.35 (1H, dd) 7.41 (1H, dd) 7.63 (1H, d) 7.88 (1H, s) 8.34 (1H, d) 13.11 (1H, br) | 539 (M + H)⁺ | pale yellow crystal |
| 3 | 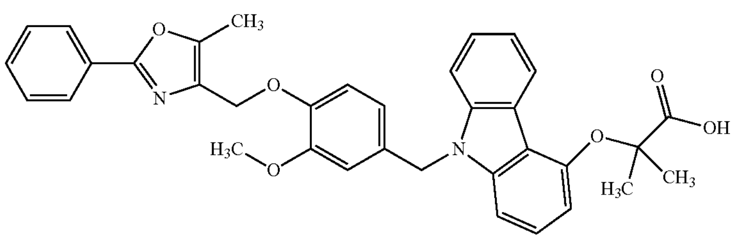 | | DMSO-d₆: 1.73 (6H, s) 2.37 (3H, s) 3.68 (3H, s) 4.87 (2H, s) 5.55 (2H, s) 6.50 (1H, d) 6.55 (1H, dd) 6.94 (1H, d) 7.04 (1H, d) 7.21 (1H, dd) 7.25 (1H, d) 7.30 (1H, dd) 7.41 (1H, dd) 7.48-7.55 (3H, m) 7.63 (1H, d) 7.88-7.98 (2H, m) 8.26 (1H, br) 13.16 (1H, br) | 577 (M + H)⁺ | pale yellow powder |
| 4 | 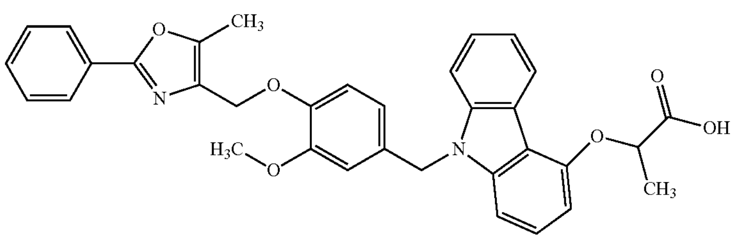 | (±) | DMSO-d₆: 1.70 (3H, d) 2.37 (3H, s) 3.68 (3H, s) 4.87 (2H, s) 5.07 (1H, q) 5.56 (2H, s) 6.53 (1H, dd) 6.59 (1H, d) 6.94 (1H, d) 7.04 (1H, d) 7.21 (1H, dd) 7.26 (1H, d) 7.33 (1H, dd) 7.41 (1H, dd) 7.48-7.54 (3H, m) 7.63 (1H, d) 7.90 (1H, d) 7.92 (1H, d) 8.27 (1H, d) 13.08 (1H, br) | 563 (M + H)⁺ | white crystal |

TABLE 1-continued

Structure and properties of compounds of examples

| Example | Structure | Steric | 1H-NMR (400 MHz) | MS (FAB) m/z: | Aspect |
|---|---|---|---|---|---|
| 5 | 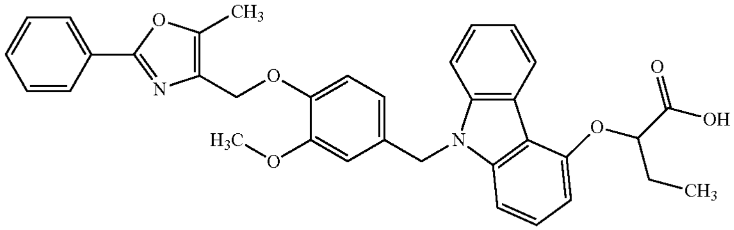 | | DMSO-d6: 1.15 (3H, t) 2.05-2.14 (2H, m) 2.39 (s, 3H) 3.68 (s, 3H) 4.87 (s, 2H) 4.93 (1H, t) 5.59 (s, 2H) 6.54 (1H, dd) 6.57 (1H, d) 6.94 (1H, d) 7.04 (1H, d) 7.20-7.28 (2H, m) 7.33 (1H, dd) 7.41 (1H, dd) 7.48-7.54 (3H, m) 7.65 (1H, d) 7.89-7.94 (2H, m) 8.26 (1H, d) 13.08 (brd, 1H) | 577 (M + H)+ | white crystal |
| 6 | 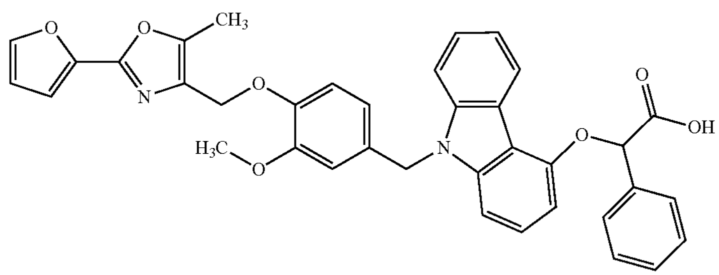 | (±) | DMSO-d6: 2.34 (3H, s) 3.67 (3H, s) 4.84 (2H, d) 5.56 (2H, s) 6.11 (1H, s) 6.53 (1H, dd) 6.65-6.73(2H, m), 6.91 (1H, d) 7.03 (1H, d) 7.07 (1H, d) 7.20-7.36 (3H, m) 7.38-7.52 (4H, m) 7.65 (1H, d) 7.69-7.76 (2H, m) 7.89 (1H, s) 8.37 (1H, d) 13.30 (1H, br) | 615 (M + H)+ | pale yellow crystal |
| 7 | 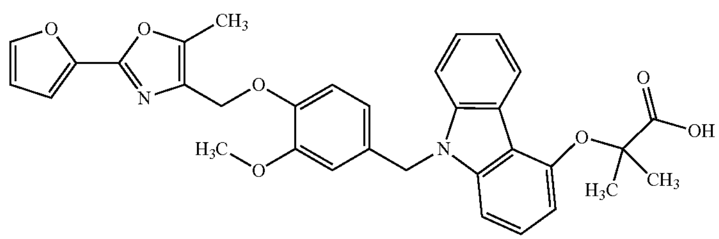 | (±) | DMSO-d6: 1.73 (6H, s) 2.34 (3H, s) 3.67(3H, s) 4.84 (2H, d) 5.55 (2H, s) 6.48-6.57 (2H, m) 6.66-6.73 (1H, s) 6.90-6.97 (1H, m) 7.00-7.14 (2H, m) 7.18-7.33 (3H, m) 7.41 (1H, dd) 7.63 (1H, d) 7.88 (1H, d) 8.26 (1H, d) 13.14 (1H, br) | 567 (M + H)+ | white powder |

TABLE 1-continued

Structure and properties of compounds of examples

| Example | Structure | Steric | ¹H-NMR (400 MHz) | MS (FAB) m/z: | Aspect |
|---|---|---|---|---|---|
| 8 | 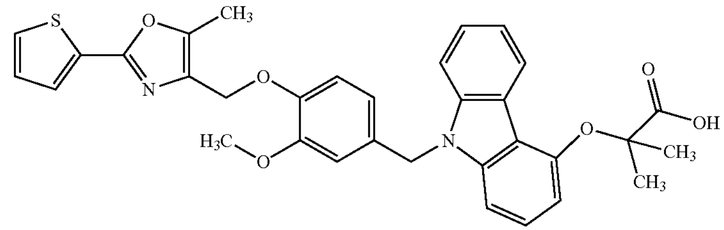 | | DMSO-d₆: 1.71 (6H, s) 2.34 (3H, s) 3.68 (3H, s) 4.83 (2H, s) 5.55 (2H, s) 6.50-6.56 (2H, m) 6.92 (1H, d) 7.04 (1H, s) 7.18-7.31 (4H, m) 7.40 (1 H, t) 7.62 (2H, d) 7.74 (1 H, d) 8.25 (1H, d) 8.61 (1H, s) | 583 (M + H)⁺ | pale yellow powder |
| 9 | 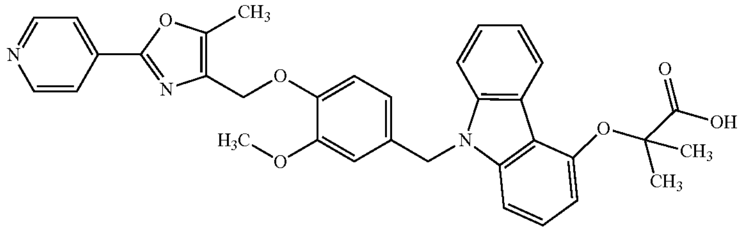 | | DMSO-d₆: 1.73 (6H, s) 2.41 (3H, s) 3.69 (3H, s) 4.91 (2H,) 5.57 (2H, s) 6.50 (1H, d) 6.54 (1H, dd) 6.94 (1H, d) 7.05 (1H, d) 7.19-7.32 (3H, m) 7.41 (1H, dd) 7.65 (1H, d) 7.82 (2H, d) 8.26 (1H, d) 8.72 (2H, d) | 578 (M + H)⁺ | white crystal |
| 10 | 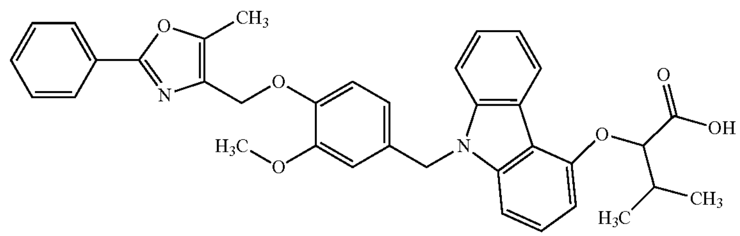 | (±) | DMSO-d₆: 1.16 (3H, d) 1.22 (3H, d) 2.37 (3H, s) 2.38-2.46 (1H, m) 3.68 (3H, s) 4.78 (1H, d) 4.87 (2H, s) 5.57 (2H, s) 6.54 (1H, dd) 6.55 (2H, d) 6.94 (1H, dd) 7.05 (1H, d) 7.24 (1H, dd) 7.26 (1H, d) 7.32 (1H, dd) 7.41 (1H, dd) 7.49-7.53 (m, 3H) 7.65 (1H, d) 7.88-7.94 (2H, m) 8.27 (1H, d) 13.08 (1H, br) | 591 (M + H)⁺ | white crystal |
| 11 | 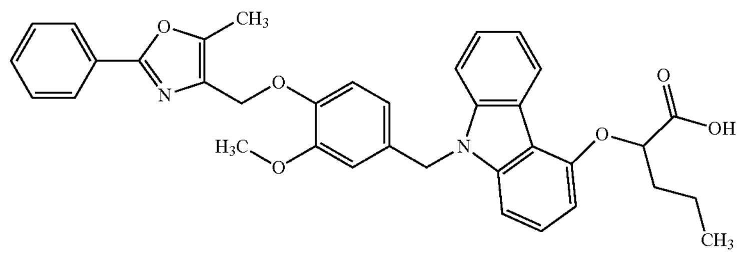 | (±) | DMSO-d₆: 1.00 (3H, t) 1.58-1.68 (2H, m) 1.96-2.13 (2H, m) 2.37 (3H, s) 3.68 (3H, s) 4.87 (2H, s) 4.95 (1H, t) 5.56 (2H, s) 6.54 (1H, dd) 6.57 (1H, d) 6.94 (1H, d) 7.05 (1H, d) 7.22 (1H, dd) 7.26 (1H, d) 7.33 (1H, d) 7.41 (1H, dd) 7.49-7.53 (m, 3H) 7.67 (d, 1H) 7.88-7.95 (2H, m) 8.24 (1H, d) 13.06 (1H, br) | 591 (M + H)⁺ | white crystal |

TABLE 1-continued

Structure and properties of compounds of examples

| Example | Structure | Steric | ¹H-NMR (400 MHz) | MS (FAB) m/z: | Aspect |
|---|---|---|---|---|---|
| 12 | 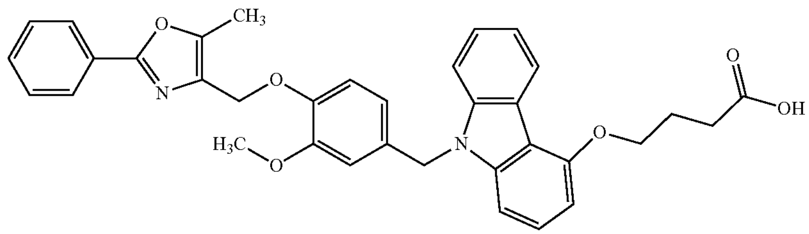 | | DMSO-d₆: 2.15 (2H, m) 2.37 (3H, s) 2.56 (2H, t) 3.67 (3H, s) 4.25 (2H, t) 4.87 (2H, s) 5.56 (2H, s) 6.52 (1H, dd) 6.76 (1H, d) 6.94 (1H, d) 7.03 (1H, d) 7.19-7.27 (2H, m) 7.32-7.43 (2H, m) 7.45-7.55 (3H, m) 7.63 (1H, d) 7.88-7.94 (2H, m) 8.19 (1H, d) 12.17 (1H, br) | 577 (M + H)⁺ | white crystal |
| 13 | 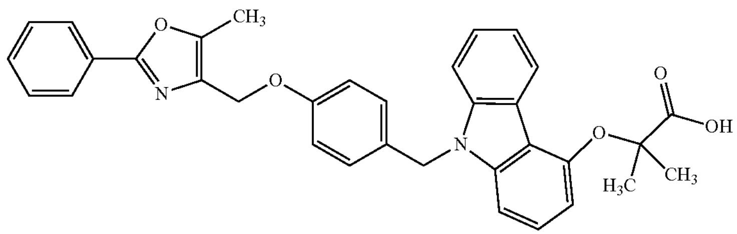 | | DMSO-d₆: 1.73 (6H, s) 2.39 (3H, s) 4.91 (2H, s) 5.56 (2H, s) 6.49 (1H, d) 6.92 (2H, d) 7.15 (2H, d) 7.18-7.32 (3H, m) 7.40 (1 H, dd) 7.47-7.54 (3H, m) 7.63 (1H, d) 7.88-7.95 (2H, m) 8.25(1H, d) 13.13(1H, br) | 547 (M + H)⁺ | pale brown powder |
| 14 | 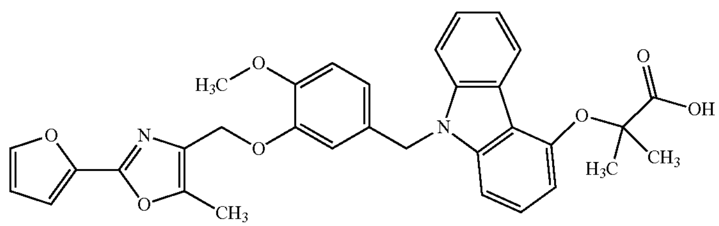 | | DMSO-d₆: 1.72 (6H, s) 2.27 (3H, s) 3.66 (3H,s) 4.88 (2H, s) 5.52 (2H, s) 6.49 (1H, dd) 6.61 (1H, dd) 6.71 (1H, dd) 6.83 (1H, d) 7.07-7.14 (2H, m) 7.16-7.30 (3H, m) 7.37 (1H, dd) 7.60 (1H, d) 7.92 (1H, d) 8.24 (1H, d) 13.15 (1H, br) | 567 (M + H)⁺ | pale yellow crystal |
| 15 | 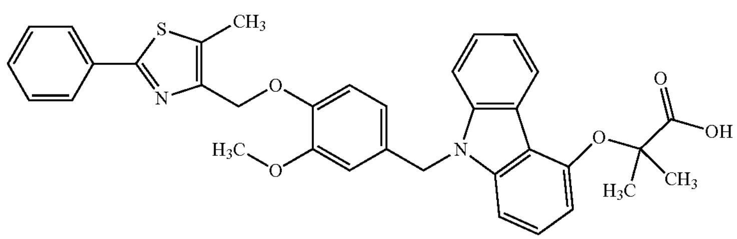 | | DMSO-d₆: 1.73 (6H, s) 2.44 (3H, s) 3.67 (3H, s) 5.00 (2H, s) 5.55 (2H, s) 6.50 (1H, d) 6.55 (1H, d) 6.98 (1H, d) 7.04 (1H, d) 7.21 (1H, t) 7.24 (1H, d) 7.30 (1H, dd) 7.41 (1H, dd) 7.44-7.52 (3H, m) 7.63 (1H, d) 7.80-7.90 (2H, m) 8.26 (1H, d) 13.13 (1H, br) | 593 (M + H)⁺ | white crystal |

TABLE 1-continued

Structure and properties of compounds of examples

| Example | Structure | Steric | ¹H-NMR (400 MHz) | MS (FAB) m/z: | Aspect |
|---|---|---|---|---|---|
| 16 | (structure with thiazole, carbazole, methoxyphenyl, and 2-methyl-2-oxy-propanoic acid groups) | | DMSO-d₆: 1.72 (6H, s) 2.35 (3H, s) 3.70 (3H, s) 5.17 (2H, s) 5.55 (2H, s) 6.50 (1H, d) 6.53 (1H, dd) 6.92 (1H, d) 7.05 (1H, d) 7.21 (1H, dd) 7.24 (1H, d) 7.29 (1H, dd) 7.40 (1H, dd) 7.44-7.51 (3H, m) 7.62 (1H, d) 7.84-7.92 (2H, m) 8.25 (1H, d) 13.15 (1H, br) | 593 (M + H)⁺ | pale yellow powder |
| 17 | (structure with oxazole, carbazole, methoxyphenyl, and 2-oxy-pentanoic acid groups) | (±) | DMSO-d₆: 0.92 (3H, t) 1.37-1.47 (2H, m) 1.54-1.64 (2H, m) 2.00-2.14 (2H, m) 2.37 (3H, s) 3.68 (3H, s) 4.87 (2H, s) 4.95 (1H, t) 5.56 (2H, s) 6.54 (1H, dd) 6.57 (1H, d) 6.94 (1H, dd) 7.05 (1H, d) 7.21 (1H, dd) 7.26 (1H, d) 7.32 (1H, dd) 7.41 (1H, dd) 7.46-7.54 (3H, m) 7.64 (1H, d) 7.88-7.95 (2H, m) 8.25 (1H, d) 13.09 (1H, br) | 605 (M + H)⁺ | white crystal |
| 18 | (structure with oxazole, carbazole, methoxyphenyl, and 2-oxy-hexanoic acid groups) | (±) | DMSO-d₆: 0.88 (3H, t) 1.28-1.42 (4H, m) 1.58-1.65 (2H, m) 2.01-2.11 (2H, m) 2.37 (3H, s) 3.68 (3H, s) 4.87 (2H, s) 4.95 (1H, t) 5.56 (2H, s) 6.54 (1H, dd) 6.57 (1H, d) 6.94 (1H, d) 7.05 (1H, d, J = 1.8 Hz) 7.21 (1H, dd) 7.26 (1H, d) 7.32 (1H, dd) 7.41 (1H, dd) 7.46-7.54 (3H, m) 7.64 (1H, d) 7.88-7.95 (2H, m) 8.25 (1H, d) 13.08 (1H, br) | 619 (M + H) 641 (M + Na)⁺ | white crystal |

TABLE 1-continued

Structure and properties of compounds of examples

| Example | Structure | Steric | ¹H-NMR (400 MHz) | MS (FAB) m/z: | Aspect |
|---|---|---|---|---|---|
| 19 | 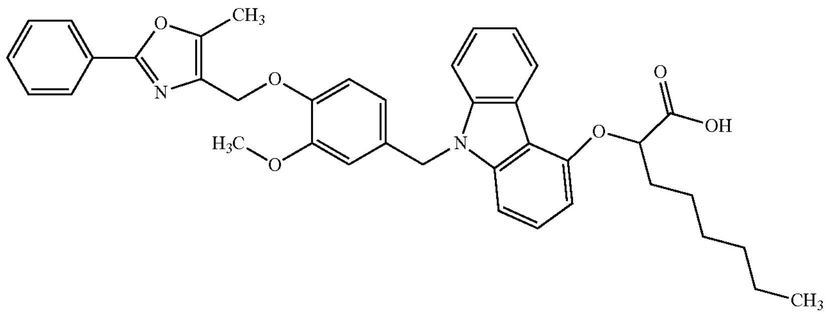 | (±) | DMSO-d₆: 0.86 (3H, t) 1.25-1.34 (4H, m) 1.36-1.45 (2H, m) 1.56-1.64 (2H, m) 2.01-2.12 (2H, m) 2.37 (3H, s) 3.68 (3H, s) 4.87 (2H, s) 4.94 (1H, t) 5.56 (2H, s) 6.54 (1H, dd) 6.56 (1H, d) 6.94 (1H, d) 7.05 (1H, d) 7.21 (1H, dd) 7.26 (1H, d) 7.32 (1H, dd) 7.41 (1H, dd) 7.46-7.54 (3H, m) 7.64 (1H, d) 7.88-7.95 (2H, m), 8.25 (1H, d) 13.09 (1H, br) | 633 (M + H)⁺ 655 (M + Na)⁺ | pale yellow crystal |
| 20 | 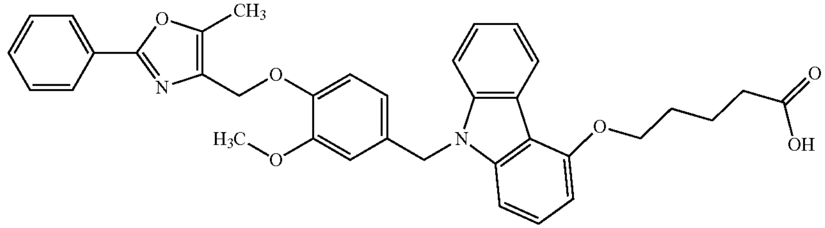 | | DMSO-d₆: 1.77-1.87 (2H, m) 1.90-1.99 (2H, m) 2.37 (3H, s) 2.38 (2H, t) 3.67 (3H, s) 4.23 (2H, t) 4.87 (2H, s) 5.56 (2H, s) 6.52 (1H, dd) 6.76 (1H, d) 6.94 (1H, d) 7.02 (1H, d) 7.20 (1H, dd) 7.24 (1H, d) 7.33-7.41 (2H, m) 7.49-7.52 (3H, m) 7.62 (1H, d) 7.90-7.92 (2H, m) 8.22 (1H, d) 12.09 (1H, s) | 591 (M + H)⁺ | white crystal |
| 21 | 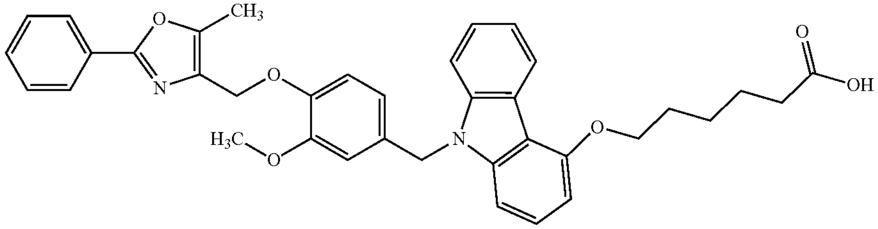 | | DMSO-d₆: 1.57-1.70 (4H, m) 1.89-1.96 (2H, m) 2.29 (2H, t) 2.37 (3H, s) 3.67 (3H, s) 4.22 (2H, t) 4.87 (2H, s) 5.55 (2H, s) 6.52 (1H, dd) 6.76 (1H, d) 6.94 (1H, d) 7.02 (1H, d) 7.21 (1H, dd) 7.24 (1H, d) 7.33-7.41 (2H, m) 7.49-7.52 (3H, m) 7.62 (1H, d) 7.90-7.92 (2H, m) 8.20 (1H, d) 12.01 (1H, s) | 605 (M + H)⁺ | pale brown crystal |

TABLE 1-continued

Structure and properties of compounds of examples

| Example | Structure | Steric | ¹H-NMR (400 MHz) | MS (FAB) m/z: | Aspect |
|---|---|---|---|---|---|
| 22 | 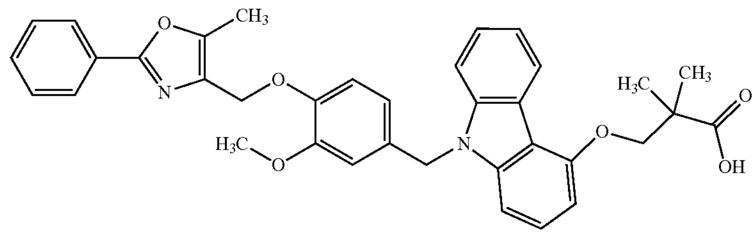 | | DMSO-d₆: 1.39 (6H, s) 2.37 (3H, s) 3.67 (3H, s) 4.21 (2H, s) 4.86 (2H, s) 5.56 (2H, s) 6.52 (1H, dd) 6.76 (1H, d) 6.93 (1H, d) 7.03 (1H, d) 7.18 (1H, dd) 7.26 (1H, d) 7.34-7.41 (2H, m) 7.48-7.54 (3H, m) 7.62 (1H, d) 7.89-7.92 (2H, m) 8.19 (1H, d) 12.48 (1H, s) | 591 (M + H)⁺ | pale brown powder |
| 23 | 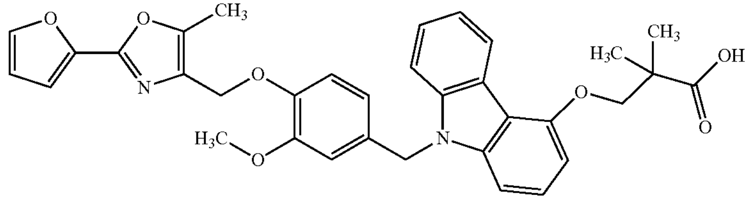 | | CDCl₃: 1.51 (6H, s) 2.34 (3H, s) 3.69 (3H, s) 4.26 (2H, s) 4.96 (2H, s) 5.40 (2H, s) 6.49 (1H, dd) 6.60 (1H, dd) 6.67 (1H, d) 6.71 (1H, d) 6.84 (1H, d) 6.94 (1H, d) 6.99 (1H, d) 7.21-7.37 (5H, m) 7.51 (1H, d) 8.32 (1H, d) caroxylic acid (not observed) | 581 (M + H)⁺ | pale yellow powder |
| 24 | 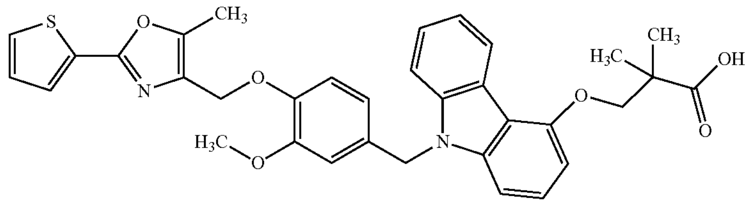 | | CDCl₃: 1.50 (6H, s) 2.32 (3H, s) 3.69 (3H, s) 4.25 (2H, s) 4.93 (2H, s) 5.39 (2H, s) 6.59 (1H, dd) 6.66 (1H, d) 6.71 (1H, d) 6.82 (1H, d) 6.98 (1H, d) 7.06 (1H, dd) 7.20-7.25 (1H, m) 7.28-7.37 (4H, m) 7.60 (1H, dd) 8.32 (1H, d) caroxylic acid (not observed) | 597 (M + H)⁺ | white powder |
| 25 | 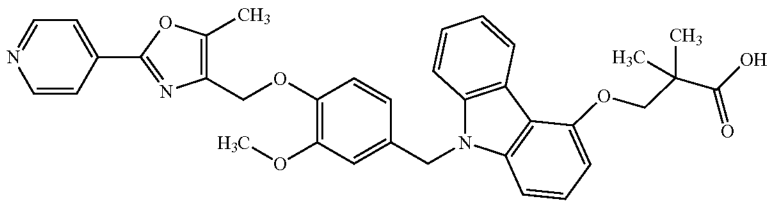 | | CDCl₃: 1.52 (6H, s) 2.38 (3H, s) 3.70 (3H, s) 4.27 (2H, s) 4.96 (2H, s) 5.41 (2H, s) 6.60 (1H, dd) 6.67 (1H, d) 6.74 (1H, d) 6.86 (1H, d) 6.99 (1H, d) 7.19-7.25 (1H, m) 7.28-7.37 (3H, m) 7.75-7.79 (2H, m) 8.34 (1H, d) 8.64-8.68 (2H, m) caroxylic acid (not observed) | 592 (M + H)⁺ | white powder |

TABLE 1-continued

Structure and properties of compounds of examples

| Example | Structure | Steric | $^1$H-NMR (400 MHz) | MS (FAB) m/z: | Aspect |
|---|---|---|---|---|---|
| 26 | 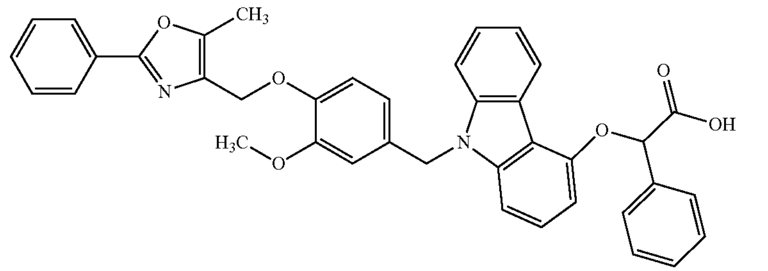 | (±) | DMSO-d$_6$: 2.37 (3H, s) 3.67 (3H, s) 4.86 (2H, d) 5.56 (2H, s) 6.11 (1H, s) 6.54 (1H, dd) 6.70 (1H, d) 7.20-7.35 (3H, m) 7.03 (1H, d) 7.39-7.55 (7H, m) 7.65 (1H, d) 7.70-7.75 (2H, m) 7.88-7.97 (2H, d) 8.37 (1H, d) 13.30 (1H, br) | 625 (M + H)$^+$ | pale yellow crystal |
| 27 | 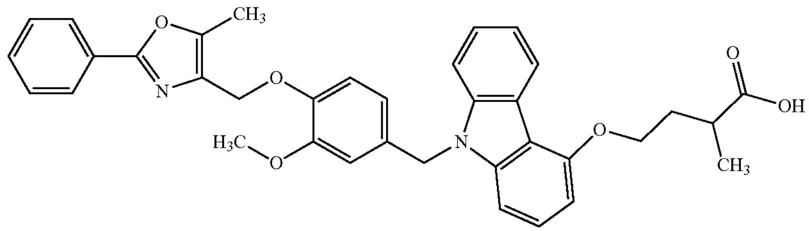 | (±) | DMSO-d$_6$: 1.22 (3H, d) 1.93-2.03 (1H, m) 2.20-2.30 (1H, m) 2.36 (3H, s) 2.70-2.80 (1H, m) 3.67 (3H, s) 4.21-4.31 (2H, m) 4.87 (2H, s) 5.55 (2H, s) 6.53 (1H, dd) 6.76 (1H, d) 6.94 (1H, d) 7.03 (1H, d) 7.18-7.27 (2H, m) 7.33-7.42 (2H, m) 7.48-7.54 (3H, m) 7.62 (1H, d) 7.88-7.94 (2H, m) 8.20 (1H, d) 12.24 (1H, s) | 591 (M + H)$^+$ | white crystal |
| 28 | 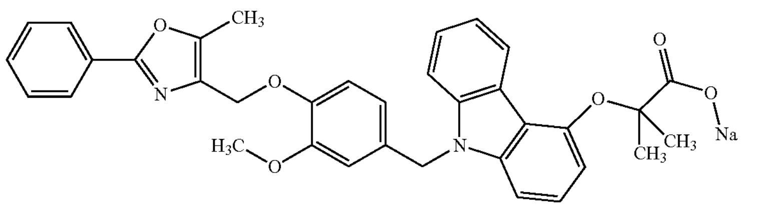 | | DMSO-d$_6$: 1.59 (6H, s) 2.37 (3H, s) 3.67 (3H, s) 4.86 (2H, s) 5.52 (2H, s) 6.52 (1H, dd) 6.65 (1H, d) 6.93 (1H, d) 7.02 (1H, d) 7.07(1H, d) 7.14-7.22 (2H, m) 7.35 (1H, dd) 7.48-7.55 (3H, m) 7.56 (1H, d) 7.88-7.95(2H, m) 8.26 (1H, d) | 599 (M + H)$^+$ 621 (M + Na)$^+$ | white crystal |
| 29 | 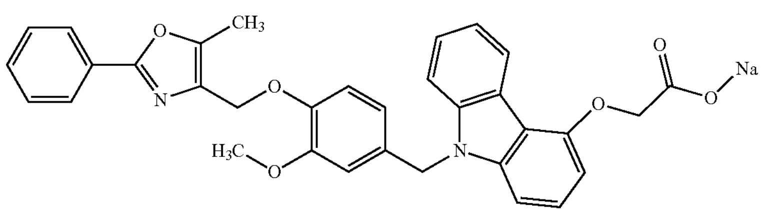 | | DMSO-d$_6$: 2.36 (3H, s) 3.67 (3H, s) 4.33 (2H, d) 4.86 (2H, s) 5.53 (2H, s) 6.53 (1H, dd) 6.57 (1H, d) 6.94 (1H, d) 7.01 (1H, d) 7.13-7.19 (2H, m) 7.27 (1H, dd) 7.34-7.38 (1H, m) 7.48-7.58 (4H, m) 7.89-7.93 (2H, m) 8.39 (1H, d) | 571 (M + H)$^+$ | white crystal |

TABLE 1-continued

Structure and properties of compounds of examples

| Example | Structure | Steric | $^1$H-NMR (400 MHz) | MS (FAB) m/z: | Aspect |
|---|---|---|---|---|---|
| 30 | 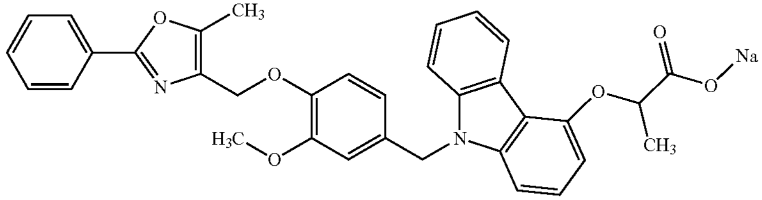 | (±) | DMSO-d$_6$: 1.56 (3H, d) 2.36 (3H, s) 3.67 (3H, s) 4.49 (2H, q) 4.86 (2H, s) 5.53 (2H, s) 6.51 (1H, d) 6.58 (1H, d) 6.93 (1H, d) 7.01 (1H, d) 7.10 (1H, d) 7.18 (1H, dd) 7.23 (1H, d) 7.35 (1H, dd) 7.48-7.53 (2H, m) 7.56 (1H, d) 7.88-7.94 (2H, m) 8.30 (1H, d) | 585 (M + H)$^+$ | white crystal |
| 31 | 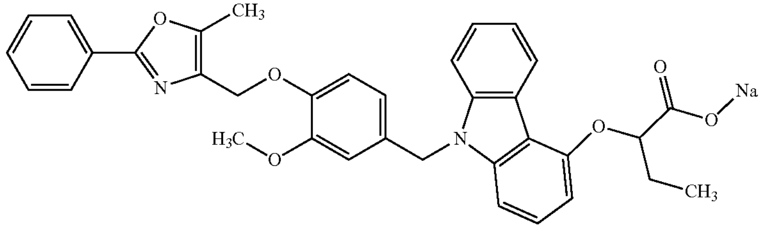 | | DMSO-d$_6$: 1.10 (3H, t, 3H) 1.90-1.99 (2H, m) 2.36 (s, 3H) 3.67 (3H, s) 4.25 (1H, t) 4.86 (2H, s) 5.53 (2H, s) 6.51 (1H, dd) 6.55 (1H, d) 6.93 (1H, d) 7.02 (1H, d) 7.08 (1H, d) 7.15-7.25 (2H, m) 7.36 (1H, dd) 7.47-7.53 (3H, m) 7.56 (1H, d) 7.88-7.95 (2H, m) 8.28 (1H, d) | 599 (M + H)$^+$ | white crystal |
| 32 | 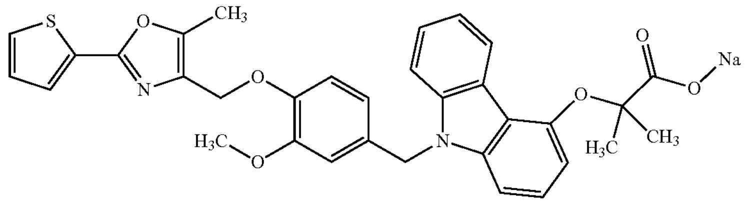 | | DMSO-d$_6$: 1.58 (6H, s) 2.34 (3H, s) 3.67 (3H, s) 4.83 (2H, s) 5.51 (2H, s) 6.52 (1H, dd) 6.70 (1H, d) 6.91 (1H, d) 7.01 (1H, d) 7.04 (1H, d) 7.14-7.20 (3H, m) 7.32-7.36 (1H, m) 7.55 (1H, d) 7.62 (1H, dd) 7.74 (1H, dd) 8.27 (1H, d) | 605 (M + H)$^+$ 627 (M + Na)$^+$ | pale yellow powder |
| 33 | 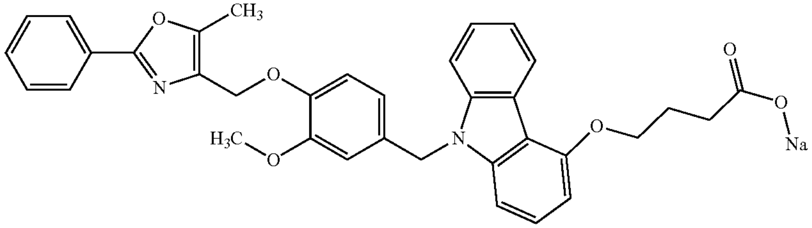 | | DMSO-d$_6$: 2.00-2.14 (4H, m) 2.37 (3H, s) 3.67 (3H, s) 4.21 (2H, t) 4.87 (2H, s) 5.55 (2H, s) 6.52 (1H, dd) 6.75 (1H, d) 6.94 (1H, dd) 7.02 (1H, d) 7.18-7.24 (2H, m) 7.30-7.42 (2H, m) 7.47-7.54 (3H, m) 7.61 (1H, d) 7.88-7.94 (2H, m) 8.21 (1H, d) | 599 (M + H)$^+$ 621 (M + Na)$^+$ | white crystal |

TABLE 1-continued

Structure and properties of compounds of examples

| Example | Structure | Steric | ¹H-NMR (400 MHz) | MS (FAB) m/z: | Aspect |
|---|---|---|---|---|---|
| 34 | (oxazole-carbazole-Na carboxylate structure) | | DMSO-d₆: 1.26 (6H, s) 2.37 (3H, s) 3.67 (3H, s) 4.12 (2H, s) 4.86 (2H, s) 5.55 (2H, s) 6.51 (1H, dd) 6.69 (1H, d) 6.93 (1H, d) 7.02 (1H, d), 7.17-7.21 (2H, m) 7.31-7.39 (2H, m) 7.49-7.52 (3H, m) 7.60 (1H, d) 7.90-7.92 (2H, m) 8.30 (1H, d) | 613 (M + H)⁺ 635 (M + Na)⁺ | pale yellow crystal |
| 35 | (oxazole-pyridine-carbazole-Na carboxylate structure) | | DMSO-d₆: 1.27 (6H, s) 2.40 (3H, s) 3.67 (3H, s) 4.13 (2H, s) 4.90 (2H, s) 5.55 (2H, s) 6.52 (1H, dd) 6.69 (1H, d) 6.93 (1H, d) 7.03 (1H, d) 7.18-7.21 (2H, m) 7.31-7.39 (2H, m) 7.60 (1H, d) 7.82 (2H, dd) 8.30 (1H, d) 8.72 (2H, dd) | 614 (M + H)⁺ 636 (M + Na)⁺ | white powder |
| 36 | (oxazole-carbazole-phenyl-Na carboxylate structure) | (±) | DMSO-d₆: 2.36 (3H, s) 3.67 (3H, s) 4.86 (2H, d) 5.39 (1H, s) 5.54 (2H, s) 6.52 (1H, dd) 6.65 (1H, d) 6.93 (1H, d) 7.02 (1H, d) 7.13 (1H, d) 7.18 (1H, dd) 7.21-7.28 (2H, m) 7.31-7.39 (3H, m) 7.45-7.55 (3H, m) 7.58 (1H, d) 7.68 (2H, d) 7.88-7.95 (2H, m) 8.40 (1H, d) | 647 (M + H)⁺ 669 (M + Na)⁺ | white powder |

TABLE 1-continued

Structure and properties of compounds of examples

| Example | Structure | Steric | ¹H-NMR (400 MHz) | MS (FAB) m/z: | Aspect |
|---|---|---|---|---|---|
| 37 | 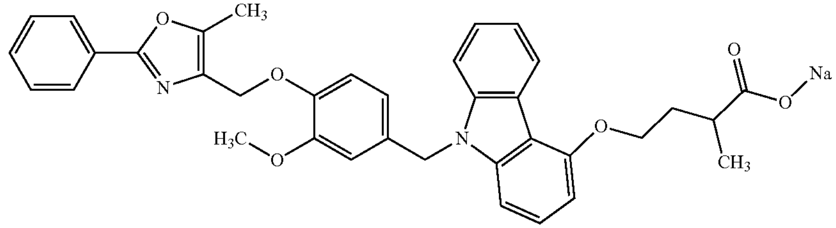 | (±) | DMSO-d₆: 1.07 (3H, d) 1.75-1.83 (1H, m) 2.13-2.21 (1H, m) 2.22-2.31 (1H, m) 2.37 (3H, s) 3.67 (3H, s) 4.17-4.27 (2H, m) 4.86 (2H, s) 5.55 (2H, s) 6.52 (1H, dd) 6.74 (1H, d) 6.94 (1H, d) 7.02 (1H, d) 7.18-7.22 (2H, m) 7.31-7.40 (2H, m) 7.47-7.53 (3H, m) 7.60 (1H, d) 7.90-7.92 (2H, m) 8.21 (1H, d) | 613 (M + H)⁺ 635 (M + Na)⁺ | white powder |
| 38 | 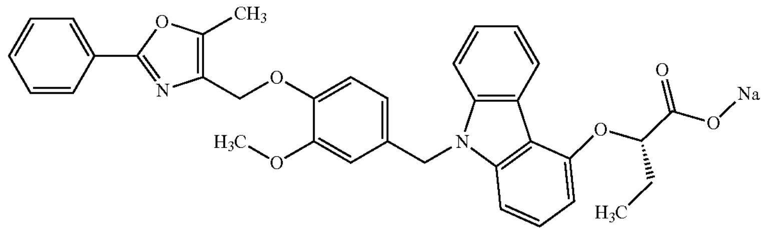 | S | DMSO-d₆: 1.10 (3H, t, 3H) 1.90-1.99 (2H, m) 2.36 (s, 3H) 3.67 (3H, s) 4.25 (1H, t) 4.86 (2H, s) 5.53 (2H, s) 6.51 (1H, dd) 6.55 (1H, d) 6.93 (1H, d) 7.02 (1H, d) 7.08 (1H, d) 7.15-7.25 (2H, m) 7.36 (1H, dd) 7.47-7.53 (3H, m) 7.56 (1H, d) 7.88-7.95 (2H, m) 8.28 (1H, d) | 599 (M + H)⁺ 621 (M + Na)⁺ | white powder |
| 39 | 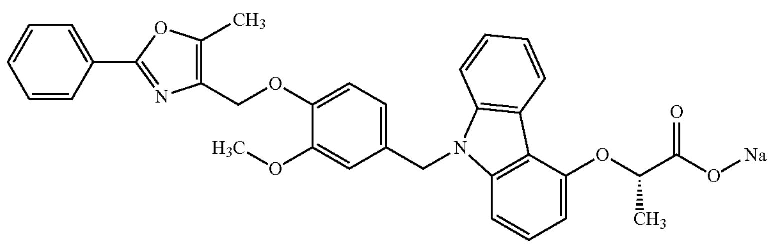 | S | DMSO-d₆: 1.56 (3H, d) 2.36 (3H, s) 3.67 (3H, s) 4.49 (2H, q) 4.86 (2H, s) 5.53 (2H, s) 6.51 (1H, dd) 6.58 (1H, d) 6.93 (1H, d) 7.01 (1H, d) 7.10 (1H, d) 7.18 (1H, dd) 7.23 (1H, d) 7.35 (1H, dd) 7.48-7.53 (2H, m) 7.56 (1H, d) 7.88-7.94 (2H, m) 8.30 (1H, d) | 585 (M + H)⁺ 607 (M + Na)⁺ | white powder |

TABLE 1-continued

Structure and properties of compounds of examples

| Example | Structure | Steric | ¹H-NMR (400 MHz) | MS (FAB) m/z: | Aspect |
|---|---|---|---|---|---|
| 40 | 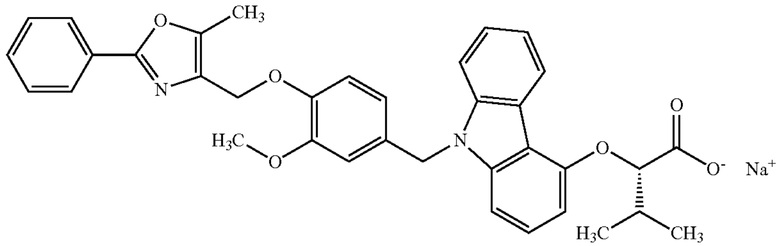 | S | DMSO-d₆: 1.09 (3H, d) 1.17 (3H, d) 2.28-2.37 (1H, m) 2.37 (3H, s) 3.68 (3H, s) 4.17 (1H, d) 4.86 (2H, s) 5.53 (2H, s) 6.52 (1H, dd) 6.56 (1H, d) 6.93 (1H, d) 7.02 (1H, d) 7.09 (1H, d) 7.18-7.24 (2H, m) 7.34-7.38 (1H, m) 7.47-7.53 (3H, m) 7.58 (1H, d) 7.89-7.93 (2H, m) 8.31 (1H, d) | 613 (M + H)⁺ 635 (M + Na)⁺ | white powder |
| 41 | 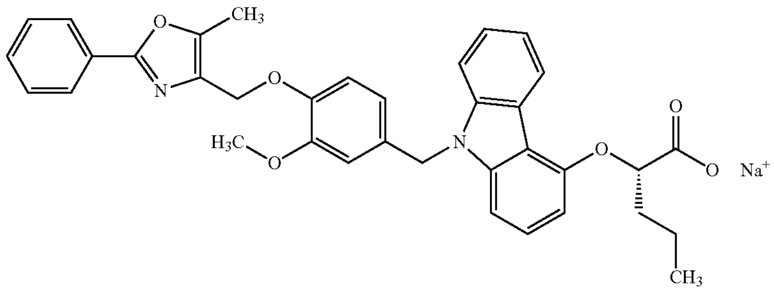 | S | DMSO-d₆: 0.96 (3H, t) 1.53-1.67 (2H, m) 1.86-1.99 (2H, m) 2.37 (3H, s) 3.67 (3H, s) 4.35 (1H, dd) 4.86 (2H, s) 5.53 (2H, s) 6.52 (1H, d) 6.56 (1H, d) 6.93 (1H, d) 7.02 (1H, d) 7.09 (1H, d) 7.17-7.24 (2H, m) 7.33-7.37 (1H, m) 7.49-7.53 (3H, m) 7.57 (1H, d) 7.89-7.93 (2H, m) 8.27 (1H, d) | 613 (M + H)⁺ 635 (M + Na)⁺ | white powder |
| 42 | 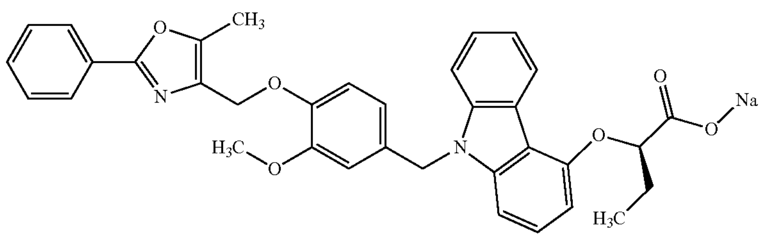 | R | DMSO-d₆: 1.10 (3H, t, 3H) 1.90-1.99 (2H, m) 2.36 (s, 3H) 3.67 (3H, s) 4.25 (1H, t) 4.86 (2H, s) 5.53 (2H, s) 6.51 (1H, dd) 6.55 (1H, d) 6.93 (1H, d) 7.02 (1H, d) 7.08 (1H, d) 7.15-7.25 (2H, m) 7.36 (1H, dd) 7.47-7.53 (3H, m) 7.56 (1H, d) 7.88-7.95 (2H, m) 8.28 (1H, d) | 599 (M + H)⁺ 621 (M + Na)⁺ | white powder |

TABLE 1-continued

Structure and properties of compounds of examples

| Example | Structure | Steric | ¹H-NMR (400 MHz) | MS (FAB) m/z: | Aspect |
|---|---|---|---|---|---|
| 43 | 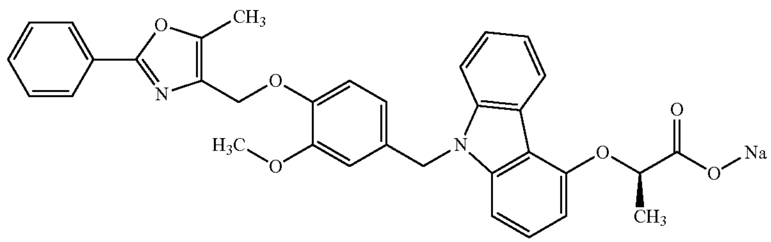 | R | DMSO-d₆: 1.56 (3H, d) 2.36 (3H, s) 3.67 (3H, s) 4.49 (2H, q) 4.86 (2H, s) 5.53 (2H, s) 6.51 (1H, dd) 6.58 (1H, d) 6.93 (1H, d) 7.01 (1H, d) 7.10 (1H, d) 7.18 (1H, dd) 7.23 (1H, d) 7.35 (1H, dd) 7.48-7.53 (2H, m) 7.56 (1H, d) 7.88-7.94 (2H, m) 8.30 (1H, d) | 585 (M + H)⁺ 607 (M + Na)⁺ | white powder |
| 44 | 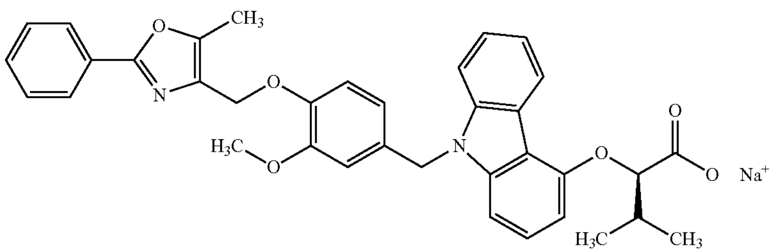 | R | DMSO-d₆: 1.09 (3H, d) 1.17 (3H, d) 2.28-2.37 (1H, m) 2.37 (3H, s) 3.68 (3H, s) 4.17 (1H, d) 4.86 (2H, s) 5.53 (2H, s) 6.52 (1H, dd) 6.56 (1H, d) 6.93 (1H, d) 7.02 (1H, d) 7.09 (1H, d) 7.18-7.24 (2H, m) 7.34-7.38 (1H, m) 7.47-7.53 (3H, m) 7.58 (1H, d) 7.89-7.93 (2H, m) 8.31 (1H, d) | 613 (M + H)⁺ 635 (M + Na)⁺ | white powder |
| 45 | 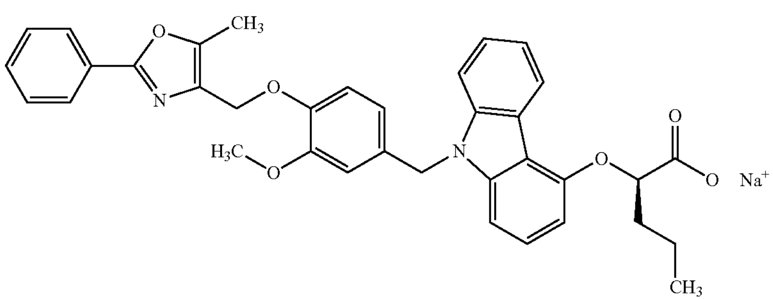 | R | DMSO-d₆: 0.96 (3H, t) 1.53-1.67 (2H, m) 1.86-1.99 (2H, m) 2.37 (3H, s) 3.67 (3H, s) 4.35 (1H, dd) 4.86 (2H, s) 5.53 (2H, s) 6.52 (1H, dd) 6.56 (1H, d) 6.93 (1H, d) 7.02 (1H, d) 7.09 (1H, d) 7.17-7.24 (2H, m) 7.33-7.37 (1H, m) 7.49-7.53 (3H, m) 7.57 (1H, d) 7.89-7.93 (2H, m) 8.27 (1H, d) | 613 (M + H)⁺ 635 (M + Na)⁺ | white powder |

TABLE 1-continued

Structure and properties of compounds of examples

| Example | Structure | Steric | ¹H-NMR (400 MHz) | MS (FAB) m/z: | Aspect |
|---|---|---|---|---|---|
| 46 | 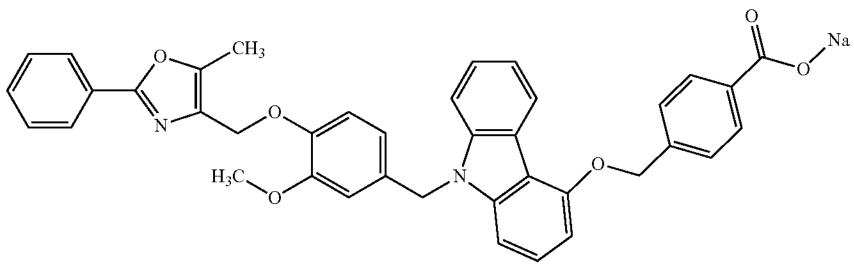 | | DMSO-d₆: 2.37 (3H, s) 3.67 (3H, s) 4.86 (2H, s) 5.34 (2H, s) 5.57 (2H, s) 6.53 (1H, dd) 6.88 (1H, d) 6.94 (1H, d) 7.03 (1H, d) 7.18 (1H, dd) 7.26 (1H, d) 7.34-7.40 (2H, m) 7.45-7.52 (5H, m) 7.62 (1H, d) 7.87-7.94 (4H, m) 8.16 (1H, d) | 647 (M + H)⁺ | white powder |
| 47 | 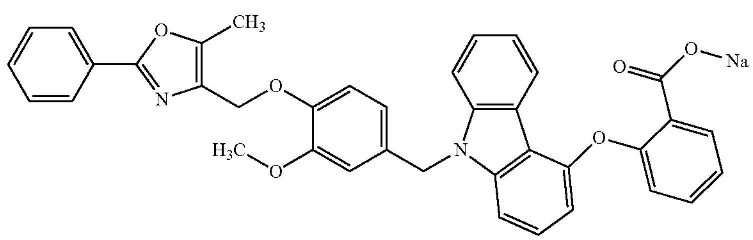 | | DMSO-d₆: 2.37 (3H, s) 3.68 (3H, s) 4.88 (2H, s) 5.59 (2H, s) 6.55 (1H, dd) 6.60 (1H, dd) 6.72 (1H, dd) 6.96-7.14 (5H, m) 7.29-7.53 (7H, m) 7.63 (1H, d) 7.91-7.93 (2H, m) 8.31 (1H, d) | 633 (M + H)⁺ | white powder |
| 48 | 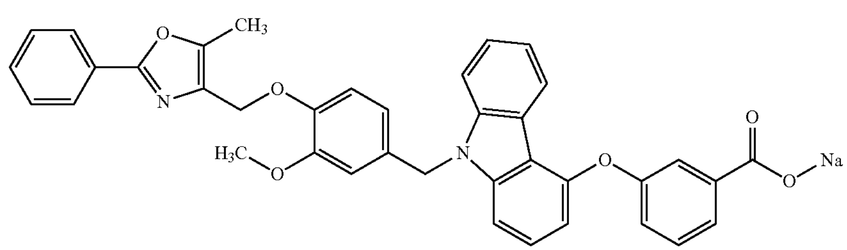 | | DMSO-d₆: 2.38 (3H, s) 3.69 (3H, s) 4.88 (2H, s) 5.62 (2H, s) 6.61 (1H, dd) 6.69 (1H, d) 6.98 (1H, d) 7.07 (1H, d) 7.09 (1H, dd) 7.14 (1H, dd) 7.29 (1H, dd) 7.39-7.54 (7H, m) 7.61 (1H, d) 7.68 (1H, d) 7.90-7.93 (2H, m) 7.99 (1H, d) | 633 (M + H)⁺ | white powder |

TABLE 1-continued
Structure and properties of compounds of examples
| Example | Structure | Steric | ¹H-NMR (400 MHz) | MS (FAB) m/z: | Aspect |
|---|---|---|---|---|---|
| 49 | 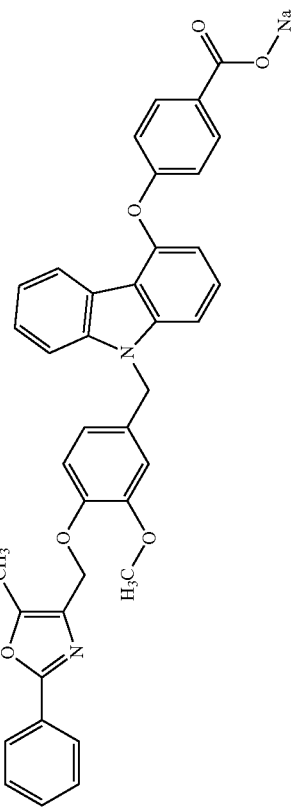 | | MeOD: 2.21 (3H, s) 3.57 (3H, s) 4.83 (2H, s) 5.47 (2H, s) 6.57 (1H, dd) 6.66 (1H, d) 6.74 (1H, d) 6.82 (1H, d) 6.89-6.93 (2H, m) 6.97-7.01 (1H, m) 7.21 (1H, d) 7.25-7.30 (2H, m) 7.34-7.38 (4H, m) 7.83-7.89 (5H, m) | 633 (M + H)⁺ | white powder |
| 50 | 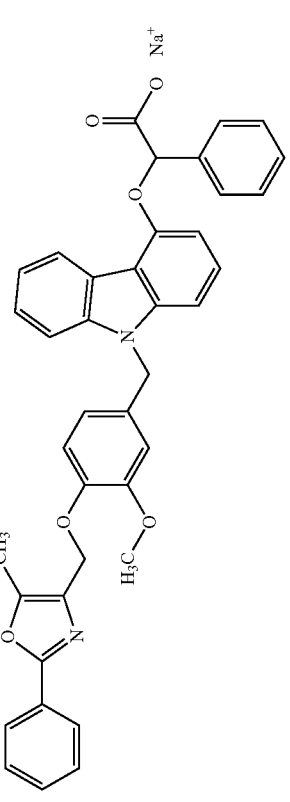 | (+) | DMSO-d₆: 2.36 (3H, s) 3.67 (3H, s) 4.86 (2H, d) 5.39 (1H, s) 5.54 (2H, s) 6.52 (1H, dd) 6.65 (1H, d) 6.93 (1H, d) 7.02 (1H, d) 7.13 (1H, d) 7.18 (1H, dd) 7.21-7.28 (2H, m) 7.31-7.39 (3H, m) 7.45-7.55 (3H, m) 7.58 (1H, d) 7.68 (2H, d) 7.88-7.95 (2H, m) 8.40 (1H, d) | 647 (M + H)⁺ 669 (M + Na)⁺ | pale brown powder |
| 51 | 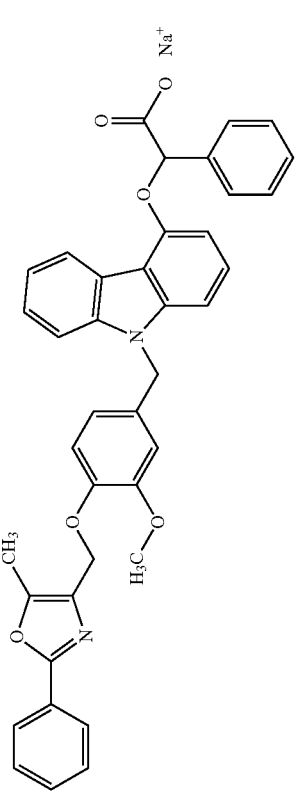 | (−) | DMSO-d₆: 2.36 (3H, s) 3.67 (3H, s) 4.86 (2H, d) 5.39 (1H, s) 5.54 (2H, s) 6.52 (1H, dd) 6.65 (1H, d) 6.93 (1H, d) 7.02 (1H, d) 7.13 (1H, d) 7.18 (1H, dd) 7.21-7.28 (2H, m) 7.31-7.39 (3H, m) 7.45-7.55 (3H, m) 7.58 (1H, d) 7.68 (2H, d) 7.88-7.95 (2H, m) 8.40 (1H, d) | 647 (M + H)⁺ 669 (M + Na)⁺ | pale brown powder |

TABLE 1-continued

Structure and properties of compounds of examples

| Example | Structure | Steric | ¹H-NMR (400 MHz) | MS (FAB) m/z: | Aspect |
|---|---|---|---|---|---|
| 52 | (carbazole structure with oxazole, methoxyphenyl, and sodium carboxylate substituents) | (−) | DMSO-d₆: 1.11 (3H, d) 1.78-1.87 (1H, m) 2.15-2.24 (1H, m) 2.36 (3H, s) 2.36-2.43 (1H, m) 3.67 (3H, s) 4.18-4.28 (2H, m) 4.86 (2H, s) 5.55 (2H, s) 6.52 (1H, dd) 6.74 (1H, d) 6.93 (1H, d) 7.02 (1H, d) 7.17-7.23 (2H, m) 7.33 (1H, dd) 7.38 (1H, dd) 7.47-7.54 (3H, m) 7.60 (1H, d) 7.88-7.94 (2H, m) 8.21 (1H, d) | 613 (M + H)⁺ 635 (M + Na)⁺ | white powder |
| 53 | (carbazole structure with oxazole, methoxyphenyl, and sodium carboxylate substituents) | (+) | DMSO-d₆: 1.11 (3H, d) 1.78-1.87 (1H, m) 2.15-2.24 (1H, m) 2.36 (3H, s) 2.36-2.43 (1H, m) 3.67 (3H, s) 4.18-4.28 (2H, m) 4.86 (2H, s) 5.55 (2H, s) 6.52 (1H, dd) 6.74 (1H, d) 6.93 (1H, d) 7.02 (1H, d) 7.17-7.23 (2H, m) 7.33 (1H, dd) 7.38 (1H, dd) 7.47-7.54 (3H, m) 7.60 (1H, d) 7.88-7.94 (2H, m) 8.21 (1H, d) | 613 (M + H)⁺ 635 (M + Na)⁺ | white powder |

Hereinafter, methods of evaluating pharmacological activities of the compounds of the present invention and pharmacological effects of the compounds of the present invention will be described.

Test Example 1 Compound Evaluation by Human PPARγ Antagonist and Agonist Assay

CV-1 cells (96 well plate), where human PPARγ and RXRα has expressed in the transient transfection of reporter plasmid (see reference 5a) were washed once with PBS (100 μL/well), and then supplemented with 100 μL/well of DMEM medium including 10% of fetal bovine serum to which test compounds at final concentrations of 10 nM, 30 nM, 100 nM, 300 nM, 1 μM, and 3 μM, as well as pioglitazone (not limited to pioglitazone shown as an example, but may be any PPARγ agonist) at a final concentration of 1 μM as a stimulant were added, and incubated in a 5% $CO_2$ incubator at 37° C. for 24 hours. After removing the medium, the CV-1 cells were washed once with PBS (100 μL/well), and supplemented with 60 μL/well of 1× Passive Lysis Buffer (manufactured by Promega Corporation). The CV-1 cells were incubated at room temperature for 30 minutes, stirred, and then by using Dual-Luciferase Reporter Assay System (manufactured by Promega Corporation), luciferase activities of firefly and renilla were measured using 1420 ARVO Multilabel Counter (manufactured by Wallac Oy). Also, the same experiments as that described above were respectively carried out for the cases where only the above-mentioned stimulants (100 nM, 1 μM, 10 μM) were used, where only the above-mentioned test compounds were used, or where neither was used (nonsupplemented), and luciferase activities of firefly and renilla were measured. Values corrected by dividing the firefly luciferase activities by the renilla luciferase activities were calculated as specific activities and used for evaluations.

Human PPARγ2 antagonist activities of the test compounds were evaluated by using a percentage (inhibition) where the specific activity in case only 1 stimulant was added is regarded as 0% and the specific activity in case the test compound and the stimulant were not added is regarded as 100%. Moreover, the concentration of the test compound indicating the inhibition rate of 50% was calculated as the $IC_{50}$ value. The results are shown in Table 2. Also, human PPARγ2 agonist activities of the test compounds were evaluated by using a percentage (activity) where the specific activity when nonsupplemented is regarded as 0% and the specific activity in case only 10 μM stimulant was added is regarded as 100%, from the specific activity in case only the test compound is used.

TABLE 2

Human PPARγ antagonist activities

| Test compound example | Inhibition $IC_{50}$(nM) |
|---|---|
| 1 | 3150 |
| 2 | 47.4% (at 10 μM) |
| 3 | 420 |
| 4 | 939 |
| 5 | 353 |
| 6 | 905 |
| 7 | 1905 |
| 8 | 545 |
| 9 | 5139 |
| 10 | 400 |
| 11 | 281 |
| 12 | 725 |
| 13 | 5870 |

TABLE 2-continued

Human PPARγ antagonist activities

| Test compound example | Inhibition $IC_{50}$(nM) |
|---|---|
| 14 | — |
| 15 | 5975 |
| 16 | 38.2% (at 10 μM) |
| 17 | 320 |
| 18 | 829 |
| 19 | 882 |
| 20 | 1604 |
| 21 | 5065 |
| 22 | 122 |
| 23 | 93 |
| 24 | 71 |
| 25 | 430 |
| 26 | 546 |
| 27 | 688 |
| 28 | 398 |
| 29 | 2463 |
| 30 | 983 |
| 31 | 406 |
| 32 | 422 |
| 33 | 1385 |
| 34 | 85 |
| 35 | 509 |
| 36 | 596 |
| 37 | 354 |
| 38 | 330 |
| 39 | 617 |
| 40 | 308 |
| 41 | 220 |
| 42 | 484 |
| 43 | 1116 |
| 44 | 462 |
| 15 | 596 |
| 46 | 992 |
| 47 | 30 |
| 48 | 2489 |
| 49 | 1051 |
| 50 | 471 |
| 51 | 2192 |
| 52 | 173 |
| 53 | 382 |

As seen from Table. 2, the compounds of the present invention have excellent PPARγ antagonist activities.

Test Example 2 Compound Evaluation by Human PPARα Antagonist and Agonist Assay

CV-1 cells (96 well plate), where human PPARα and RXRα has expressed in the transient transfection of reporter plasmid (see reference 6a) were washed once with PBS (100 μL/well), and then supplemented with 100 μL/well of DMEM medium including 10% of fetal bovine serum to which test compounds at final concentrations of 10 nM, 30 nM, 100 nM, 300 nM, 1 μM, and 3 μM, as well as GW7647 (not limited to GW7647 shown as an example, but may be any PPARα agonist) at a final concentration of 1 nM as a stimulant were added, and incubated in a 5% $CO_2$ incubator at 37° C. for 24 hours. After removing the medium, the CV-1 cells were washed once with PBS (100 μL/well), and supplemented with 60 μL/well of 1× Passive Lysis Buffer (manufactured by Promega Corporation). The CV-1 cells were incubated at room temperature for 30 minutes, stirred, and then by using Dual-Luciferase Reporter Assay System (manufactured by Promega Corporation), luciferase activities of firefly and renilla were measured using 1420 ARVO Multilabel Counter (manufactured by Wallac Oy). Also, the same experiments as that described above were respectively carried out for the cases where only the above-mentioned stimulant (10 nM, 100 nM, 1 μM) were used, where only the above-mentioned test compounds were used, or where neither was used (non-supplemented), and luciferase activities of firefly and renilla were measured. Values corrected by dividing the firefly luciferase activities by the renilla luciferase activities were calculated as specific activities and used for evaluations.

Human PPARα antagonist activities of the test compounds were evaluated by using a percentage (inhibition) where the specific activity in case only 100 nM stimulant was added is regarded as 0% and the specific activity in case the test compound and the stimulant were not added is regarded as 100%.

Also, human PPARα agonist activities of the test compounds were evaluated by using a percentage (activity) where the specific activity when nonsupplemented is regarded as 0% and the specific activity in case only 1 μM stimulant was added is regarded as 100%, from the specific activity in case only the test compound is used. The results are shown in Table 3.

TABLE 3

Human PPARα agonist activities

| Test compound example | Activity % (at 1 μM) |
| --- | --- |
| 3 | 43 |
| 4 | 21 |
| 5 | 27 |
| 7 | 39 |
| 8 | 60 |
| 9 | 27 |
| 13 | 37 |
| 15 | 73 |
| 16 | 56 |
| 22 | 40 |
| 23 | 69 |
| 24 | 64 |
| 25 | 47 |
| 27 | 23 |
| 28 | 56 |
| 30 | 35 |
| 31 | 21 |
| 32 | 66 |
| 34 | 41 |
| 37 | 20 |
| 38 | 32 |
| 43 | 35 |

From Table 3, it is seen that at least some of the compounds of the present invention have PPARα agonist effect.

Reference 1a (Cloning of Human PPARγ Gene)

Cloning of human PPARγ gene was carried out by PCR method using primer sets:

```
                                    (Sequence number: 1)
hPPARg2-F1: 5'-TTC TCG AGG CAA ACC CCT ATT CCA TGC
TGT-3';
and
                                    (Sequence number: 2)
hPPARg2-R1: 5'-GAA ATG TTG GCA GTG GCT CAG-3';
``` that were designed based on human PPARγ2 gene sequence (Genbank accession No. U79012) with human stomach cDNA library (manufactured by Takara Shuzo) used as template.

For PCR reaction, TaKaRa LA Taq polymerase (manufactured by Takara Shuzo) was used. First, 10 μl of 10×LA PCR Buffer, 10 μl of 1.5 mM MgCl$_2$ solution, 16 μl of 2.5 mM dNTP solution, 1 μl of human stomach cDNA library as a template, 5 μl each of 10 μM primer solutions, 1 μl of TaKaRa LA Taq polymerase, and 52 μl of sterile distilled water were mixed to obtain reaction mixture.

A tube including the above-mentioned reaction mixture was set in the iCycler™ Thermal Cycler (manufactured by BIO-RAD Laboratories, Inc.), and then processed at 95° C. for 2 minutes. Moreover, after repeating 35 cycles of 20 seconds at 95° C. and 2 minutes at 68° C., the process was carried out at 72° C. for 5 minutes.

The PCR product prepared by the PCR reaction was linked to pGEM-T vector (manufactured by Promega Corporation) by TA cloning, and a plasmid pGEMT-hPPARg2 was prepared. 1.6 kb of fragment of the prepared plasmid pGEMT-hPPARg2 including human PPARγ gene was cut with SpiII, smoothed, and further cut with SalI was inserted into SalI-SmaI site of pCI-neo vector (manufactured by Promega Corporation), whereby plasmid pCI-hPPARg 2 was prepared.

Reference 2a (Cloning of human PPARα gene)

Cloning of human PPARα gene was carried out by PCR method using primer sets:

```
                                    (Sequence number: 3)
hPPARa-F1: 5'-TTG CTA GCC GTG CTT CCT GCT TCA TAG
AT-3';
and
                                    (Sequence number: 4)
hPPARa-R1: 5'-TTG TCG ACT CCT GGA AAA GGT GTG GCT
GATG-3';
``` that were designed based on human PPARα gene sequence (Genbank accession No. S74349) with human liver cDNA library (manufactured by Takara Shuzo) used as template.

For PCR reaction, TaKaRa LA Taq polymerase (manufactured by Takara Shuzo) was used. First, 10 μl of 10×LA PCR Buffer, 10 μl of 1.5 mM Mg Cl$_2$ solution, 16 μl of 2.5 mM dNTP solution, 1 μl of human liver cDNA library as a template, 5 μl each of 10 μM primer solutions, 1 μl of TaKaRa LA Taq polymerase, and 52 μl of sterile distilled water were mixed to obtain reaction mixture.

A tube including above-mentioned reaction mixture was set in the iCycler™ Thermal Cycler (manufactured by BIO-RAD Laboratories, Inc.), and then processed at 95° C. for 2 minutes. Moreover, after repeating a 35 cycles of 20 seconds at 95° C. and 2 minutes at 68° C., the process was carried out at 72° C. for 5 minutes.

The PCR product prepared by the PCR reaction was provided with an agarose gel (1%) electrophoresis, 1.6 kb of DNA fragment including human PPARα gene was collected from the gel by using a PCR purification system (manufactured by Promega Corporation). Thereafter, the DNA fragment was processed with 2 kinds of restriction enzymes, NheI and SalI, and inserted into NheI-SalI site of pCI-neo vector (manufactured by Promega Corporation), whereby plasmid pCI-hPPARa was prepared.

Reference 3a (Cloning of RXRα Gene)

Cloning of human PPARα gene was carried out by PCR method using primer sets:

```
                                    (Sequence number: 5)
hRXRa-F1: 5'-ACG AAT TCA GTT AGT CGC AGA CAT GGA
C-3';
and
                                    (Sequence number: 6)
hRXRa-R1: 5'-GTT CTA GAG CAG GCC TAA GTC ATT TGG
T-3';
``` that were designed based on human RXRα gene sequence (Genbank accession No. NM_002957) with human liver cDNA library (manufactured by Takara Shuzo) used as template.

For PCR reaction, TaKaRa LA Taq polymerase (manufactured by Takara Shuzo) was used. First, 10 μl of 10×LA PCR Buffer, 10 μl of 1.5 mM Mg $Cl_2$ solution, 16 μl of 2.5 mM dNTP solution, 1 μl of human liver cDNA library as a template, 5 μl each of 10 μM primer solutions, 1 μl of TaKaRa LA Taq polymerase, and 52 μl of sterile distilled water were mixed to obtain reaction mixture.

A tube including above-mentioned reaction mixture was set in the iCycler™ Thermal Cycler (manufactured by BIO-RAD Laboratories, Inc.), and then processed at 95° C. for 2 minutes. Moreover, after repeating 35 cycles of 20 seconds at 95° C. and 2 minutes at 68° C., the process was carried out at 72° C. for 5 minutes.

The PCR product prepared by the PCR reaction was provided with an agarose gel (1%) electrophoresis, 1.4 kb of DNA fragment including human RXRα gene was collected from the gel by using a PCR purification system (manufactured by Promega Corporation). Thereafter, the DNA fragment was processed with 2 kinds of restriction enzymes, EcoRI and XbaI, and inserted into EcoRI-XbaI site of pCI-neo vector (manufactured by Promega Corporation), whereby plasmid pCI-hRXRa was prepared.

Reference 4a (Preparation of Reporter Plasmid)

A DNA fraction including PPAR responsive element (PPRE) of rat Acyl-CoA oxidase was prepared using the following DNA:

```
                                   (Sequence number: 7)
PPRE-F1: 5'-TCG ACA GGG GAC CAG GAC AAA GGT CAC
GTT CGG GAG-3'
and
                                   (Sequence number: 8)
PPRE-R1: 5'-TCG ACT CCC GAA CGT GAC CTT TGT CCT
GGT CCC CTG-3'.
```

First, PPRE-F1 and PPRE-R1, after annealing, were inserted into SalI site of a plasmid pUC18 (manufactured by Takara Shuzo). By determining the base sequence of the inserted fraction, a plasmid pUC-PPRE3 in which 3 PPREs are tandem-linked is selected.

Subsequently, pRL-TK vector (manufactured by Promega Corporation) was cut with restriction enzymes, BglII and HindIII, provided with an agarose gel (1%) electrophoresis, 760 by of DNA fragment including herpes simplex virus-thymidine kinase (HSV TK) promoter was collected from the gel by using the PCR purification system (manufactured by Promega Corporation). This DNA fragment was inserted into BglII-HindIII site of plasmid pGL3-Basic vector (manufactured by Promega Corporation), and the plasmid pGL3-TK was prepared.

5.6 kb of a fragment of the prepared plasmid pGL3-TK cut with NheI, smoothed and further cut with BglII and 120 by of a fragment of the plasmid pUC-PPRE3 cut with HindIII, smoothed and further cut with BamHI were linked, and a reporter plasmid pGL3-PPRE3-TK was prepared.

Reference 5a (Transfection of Plasmids for Human PPARγ and RXRα Expression as Well as Reporter Plasmid into CV-1 Cells and Acquisition of Transient Expression Cells)

CV-1 cells were cultured in DMEM medium (manufactured by Invitrogen Corporation) including 10% fetal bovine serum (manufactured by Dainippon Pharmaceutical Co., Ltd.) in 225T-Flask (manufactured by Corning Costar). The cells were detached by 0.5 g/L trypsin-0.2 g/L EDTA (ethylene diamine tetra-acetic acid) (manufactured by Invitrogen Corporation), and then suspended in the DMEM medium including 10% fetal bovine serum to a cell concentration of $2 \times 10^5$ cells/mL. Thereafter, the cells were seeded into 96 well plate at $2 \times 10^4$ cells/0.1 mL/well, incubated in the 5% $CO_2$ incubator at 37° C. overnight, and then the plasmids prepared by the above-mentioned reference 1a, reference 3a, and reference 4a were transfected into cells by using a lipofectamine reagent (manufactured by Invitrogen Corporation) according to the attached manual.

Namely, after CV-1 cells were cultured overnight, the cells were washed with PBS (100 μL/well). Thereafter the cells were incubated for 5 hours at 37° C./5% $CO_2$ in the MEM medium (manufactured by Invitrogen Corporation) including 430 ng/mL of human PPARγ expression plasmid (pCI-hPPARg2) prepared by the reference 1a, 430 ng/mL of human RXRα expression plasmid (pCI-hRXRa) prepared by the reference 3a, and 140 ng/mL of the reporter plasmid (pGL3-PPRE3-TK) prepared by the reference 4a, 10 ng/mL of phRL-TK vector (manufactured by Promega Corporation) and 2 μL/mL of lipofectamine.

Reference 6a (Transfection of Plasmids for Human PPARα and RXRα Expression as Well as Reporter Plasmid into CV-1 Cells and Acquisition of Transient Expression Cells)

CV-1 cells were cultured in DMEM medium (manufactured by Invitrogen Corporation) including 10% fetal bovine serum (manufactured by Dainippon Pharmaceutical Co., Ltd.) in 225T-Flask (manufactured by Corning Costar). The cells were detached by 0.5 g/L trypsin-0.2 g/L EDTA (ethylene diamine tetra-acetic acid) (manufactured by Invitrogen Corporation), and then suspended in the DMEM medium including 10% fetal bovine serum to a cell concentration of $2 \times 10^5$ cells/mL. Thereafter, the cells were seeded into 96 well plate at $2 \times 10^4$ cells/0.1 mL/well, incubated in the $CO_2$ incubator at 37° C. overnight, and then the plasmids prepared by the above-mentioned reference 2a, reference 3a, and reference 4a were transfected into cells by using a lipofectamine reagent (manufactured by Invitrogen Corporation) according to the attached manual.

Namely, after CV-1 cells were cultured overnight, the cells were washed with PBS (100 μL/well). Thereafter the cells were incubated for 5 hours at 37° C./5% $CO_2$ in the MEM medium (manufactured by Invitrogen Corporation) including 430 ng/mL of human PPARα expression plasmid (pCI-hPPARa) prepared by the reference 2a, 430 ng/mL of human RXRα expression plasmid (pCI-hRXRa) prepared by the reference 3a, and 140 ng/mL of the reporter plasmid (pGL3-PPRE3-TK) prepared by the reference 4a, 10 ng/mL of phRL-TK vector (manufactured by Promega Corporation) and 2 μL/mL of lipofectamine.

Formulation Example 1

20 g of the compound of the example 1, 315 g of lactose, 125 g of cornstarch, and 25 g of crystalline cellulose were mixed evenly, 200 ml of 7.5% hydroxypropylcellulose solution was added thereto, granulated by extruding granulating machine using a screen of 0.5 mm diameter, and immediately rounded with a marmelizer, and dried to prepare granules.

Formulation Example 2

The granules prepared by the above-mentioned formulation example 1 were coated with 1.9 kg of the film coating solution of the following composition by using a fluent granulating machine to prepare enteric granules. The composition of the coating solution is: 5.0% of hydroxypropyl methylcellulose phthalate, 0.25% of stearate, 50.0% of methylene chloride, and 44.75% of ethanol.

Formulation Example 3

20 g of the compound of the example 1, 100 g of lactose, 36 g of cornstarch, 30 g of crystalline cellulose, 10 g of carboxymethylcellulose calcium, and 4 g of magnesium stearate are mixed evenly and made into tablets of 200 mg per tablet with pestle of 7.5 mm in diameter by a single stroke tabletting machine.

Formulation Example 4

The tablets prepared by the above-mentioned formulation example 3 were spray coated, providing coating of 10 mg per tablet to prepare enteric film coating granules. The composition of the coating solution is: 8.0% of hydroxypropyl methylcellulose phthalate, 0.4% of Myvacet, 50.0% of methylene chloride, 0.1% of bleached bee's wax, and 41.5% of isopropanol.

Formulation Example 5

200 g of the compound of the example 1, 20 g of polysorbate80, and 1780 g of medium-chain triglyceride were mixed, and after complete dissolution, soft capsules including 200 mg of drug solution per capsule were prepared using coating solution for soft capsule composed of 100 units of gelatin, 30 units of concentrated glycerin, 0.4 unit of ethylparaben, and 0.2 unit of propylparaben by rotary method.

Formulation Example 6

100 mg of the compound of the example 1, 2 mg of sodium acetate, proper quantity of acetic acid (for adjustment to pH5.8), and remaining amount of distilled water (total of 10 ml/vial) were used to prepare injectable solution by common procedure for the above-mentioned prescription.

INDUSTRIAL APPLICABILITY

The compounds of the present invention have the above-mentioned effects, and therefore can be used for prevention or treatment of fatty liver, obesity, lipid metabolism abnormality, visceral adiposity, diabetes, hyperlipemia, impaired glucose tolerance, or hypertension. Moreover, the compounds of the present invention can be used in producing preventive agent or therapeutic agent for fatty liver, obesity, lipid metabolism abnormality, visceral adiposity, diabetes, hyperlipemia, impaired glucose tolerance, or hypertension.

[Array Table]

What is claimed is:

1. A carbazole derivative, hydrate thereof, or pharmaceutically acceptable salt thereof, the carbazole derivative represented by the following general formula (I):

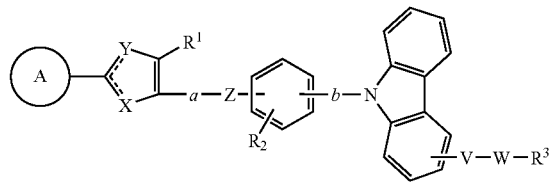

(I)

wherein a ring A represents a $C_6$-$C_{10}$ aryl group which may have 1 to 3 substituent groups selected from a group A of substituent groups, or a 5- to 7-membered aromatic heterocyclic group which may have 1 to 3 substituent groups selected from the group A of substituent groups;

X represents =N—, =CH—, —O—, or —S—;

Y represents =N—, —O—, or —S—;

a and b may be same or different, and represent a $C_1$-$C_4$ alkylene group which may have a substituent group selected from the group A of substituent groups, a $C_2$-$C_4$ alkenylene group which may have a substituent group selected from the group A of substituent groups, or a $C_2$-$C_4$ alkynylene group which may have a substituent group selected from the group A of substituent groups;

V and Z may be same or different, and represent a methylene group, =N—, —NH—, —O—, —S—, —S(=O)—, —S(=O)$_2$—, —C(=O)—, —C(=O)NH—, or —NHC(=O)—;

W represents a $C_1$-$C_{10}$ alkylene group which may have a substituent group selected from the group A of substituent groups, a $C_2$-$C_{10}$ alkenylene group which may have a substituent group selected from the group A of substituent groups, a $C_2$-$C_{10}$ alkynylene group which may have a substituent group selected from the group A of substituent groups, a $C_3$-$C_7$ cycloaliphatic hydrocarbon group which may have 1 to 3 substituent groups selected from the group A of substituent groups, or a $C_6$-$C_{10}$ arylene group which may have 1 to 3 substituent groups selected from the group A of substituent groups;

$R^1$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, or a $C_1$-$C_4$ alkoxy group which may have a substituent group selected from the group A of substituent groups;

$R^2$ represents, a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups;

$R^3$ represents a hydrogen atom, a hydroxy group, a cyano group, —C(=O)$R^4$ ($R^4$ represents a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups), or —C(=O)NR$^5$R$^6$ ($R^5$ and $R^6$ may be same or different, and represent a hydrogen atom, a hydroxy group, a $C_1$-$C_4$ alkyl group which may have a substituent group selected from the group A of substituent groups, a $C_1$-$C_4$ alkoxy group which may have a substituent group selected from the group A of substituent groups, a $C_1$-$C_4$ alkylsulfonyl group which may have a substituent group selected from the group A of substituent groups, or a $C_6$-$C_{12}$ arylsulfonyl group which may have a substituent group selected from the group A of substituent groups), the group A of substituent groups represents a group including:

halogen;

a hydroxy group;

a carboxy group;

a cyano group;

a $C_1$-$C_6$ alkyl group whose 1 to 3 hydrogen atoms may be substituted by halogen, a hydroxy group, a carboxy group, or a carbamoyl group;

a $C_2$-$C_6$ alkenyl group whose 1 to 3 hydrogen atoms may be substituted by halogen, a hydroxy group, a carboxy group, or a carbamoyl group;

a $C_2$-$C_6$ alkynyl group whose 1 to 3 hydrogen atoms may be substituted by halogen, a hydroxy group, a carboxy group, or a carbamoyl group;

a $C_1$-$C_6$ alkoxy group whose 1 to 3 hydrogen atoms may be substituted by halogen, a hydroxy group, a carboxy group, or a carbamoyl group;

a $C_1$-$C_6$ alkylthio group whose 1 to 3 hydrogen atoms may be substituted by halogen, a hydroxy group, a carboxy group, or a carbamoyl group;

a $C_3$-$C_7$ cycloaliphatic hydrocarbon group whose 1 to 3 hydrogen atoms may be substituted by halogen, a hydroxy group, a carboxy group, or a carbamoyl group;

a $C_7$-$C_{16}$ aralkyl group whose 1 to 3 hydrogen atoms may be substituted by halogen, a hydroxy group, a carboxy group, or a carbamoyl group;

a carbamoyl group which may be monosubstituted or disubstituted by a substituent group selected from a $C_1$-$C_4$ alkoxycarbonyl group, a $C_1$-$C_4$ alkyl group, a $C_1$-$C_4$ alkylsulfonyl group, and a $C_6$-$C_{10}$ arylsulfonyl group;

a $C_6$-$C_{10}$ aryl group whose 1 to 3 hydrogen atoms may be substituted by halogen, a hydroxy group, a carboxy group, or a carbamoyl group; and a 5- to 7-membered aromatic heterocyclic group whose 1 to 3 hydrogen atoms may be substituted by halogen, a hydroxy group, a carboxy group, or a carbamoyl group.

2. The carbazole derivative, hydrate thereof, or pharmaceutically acceptable salt thereof according to claim 1, wherein the carbazole derivative is represented by the following general formula (I'):

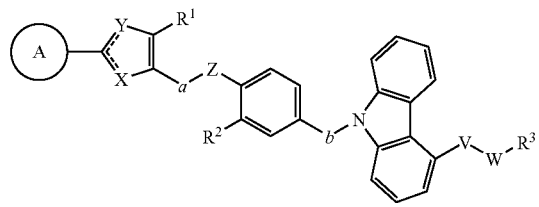

(I')

wherein the ring A, X, Y, a, b, V, Z, W, $R^1$, $R^2$, and $R^3$ respectively represent synonymous definition with those of claim 1.

3. The carbazole derivative, hydrate thereof, or pharmaceutically acceptable salt thereof according to claim 1, wherein in the formula (I):

the ring A represents {a phenyl group, an indenyl group, a 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups;

X represents =N—, —O—, or —S—;

Y represents =N—, —O—, or —S—;

a and b may be same or different, and represent a $C_1$-$C_4$ alkylene group whose 1 or 2 hydrogens are substituted by {halogen, a $C_1$-$C_4$ alkyl group, or a $C_1$-$C_4$ alkoxy group};

V and Z may be same or different, and represent a methylene group, —NH—, —O—, —S—, or —S(=O)—;

W represents a $C_1$-$C_{10}$ alkylene group which may have a substituent group selected from a group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by a substituent group selected from a group C of substituent groups, a $C_1$-$C_4$ alkoxy group whose 1 to 3 hydrogens may be substituted by a substituent group selected from the group C of substituent groups, or a $C_1$-$C_4$ alkylthio group whose 1 to 3 hydrogens may be substituted by a substituent group selected from the group C of substituent groups, where the group C of substituent groups represents a group including halogen, a $C_1$-$C_4$ alkyl group, a $C_1$-$C_4$ alkoxy group, and a $C_1$-$C_4$ haloalkyl group; and $R^3$ represents a hydrogen atom, a hydroxy group, a cyano group, or —C(=O)$R^4$ ($R^4$ represents a hydrogen atom, a hydroxy group, a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}).

4. The carbazole derivative, hydrate thereof, or pharmaceutically acceptable salt thereof according to claim 1, wherein in the formula (I):

the ring A represents {a phenyl group, an indenyl group, a 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups;

X represents =N—, —O—, or —S—;

Y represents =N—, —O—, or —S—;

a and b may be same or different, and represent a $C_1$-$C_4$ alkylene group whose 1 or 2 hydrogens may be substituted by {halogen, a $C_1$-$C_4$ alkyl group, or a $C_1$-$C_4$ alkoxy group};

V and Z may be same or different, and represent a methylene group, —NH—, —O—, —S—, or —S(=O)—;

W represents a $C_1$-$C_{10}$ alkylene group which may have a substituent group selected from the group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by {a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {a $C_1$-$C_4$ alkyl group, a $C_1$-$C_4$ alkoxy group, or a $C_1$-$C_4$ haloalkyl group}, or a $C_1$-$C_4$ alkylthio group whose 1 to 3 hydrogens may be substituted by {a $C_1$-$C_4$ alkyl group, a $C_1$-$C_4$ alkoxy group, or a $C_1$-$C_4$ haloalkyl group}; and $R^3$ represents a hydrogen atom, a hydroxy group, a cyano group, —C(=O)$R^4$ ($R^4$ represents a hydrogen atom, hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}), or —C(=O)NR$^5$R$^6$ ($R^5$ and $R^6$ may be same or different, and represent a hydrogen atom, a hydroxy group, a $C_1$-$C_4$ alkyl group, a $C_1$-$C_4$ alkoxy group, a $C_1$-$C_4$ alkylsulfonyl group, or a $C_6$-$C_{12}$ arylsulfonyl group).

5. The carbazole derivative, hydrate thereof, or pharmaceutically acceptable salt thereof according to claim 1, wherein in the formula (I):

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X represents =N—, —O—, or —S—;

Y represents =N—, —O—, or —S—;

a and b may be same or different, and represent a $C_1$-$C_4$ alkylene group; V and Z may be same or different, and represent a methylene group, —NH—, —O—, —S—, or —S(=O)—;

W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group};

$R^1$ represents a $C_1$-$C_4$ alkyl group, or a $C_1$-$C_4$ alkoxy group;

$R^2$ represents a hydrogen atom, a $C_1$-$C_4$ alkoxy group, or a $C_1$-$C_4$ alkylthio group; and $R^3$ represents a hydroxy group, or —C(=O)$R^4$ ($R^4$ represents a hydrogen atom, a hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}.

6. The carbazole derivative, hydrate thereof, or pharmaceutically acceptable salt thereof according to claim 1, wherein in the formula (I):
the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};
X and Y represent any one of: (i) X representing —O— and Y representing =N—, (ii) X representing =N— and Y representing —O— or —S—, and (iii) X representing —S— and Y representing =N—;
a and b may be same or different, and represent a $C_1$-$C_4$ alkylene group;
V and Z may be same or different, and represent —NH—, —O—, —S—, or —S(=O)—;
W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group};
$R^1$ represents a $C_1$-$C_4$ alkyl group, or a $C_1$-$C_4$ alkoxy group;
$R^2$ represents, a hydrogen atom, a $C_1$-$C_4$ alkoxy group, or a $C_1$-$C_4$ alkylthio group; and
$R^3$ represents —C(=O)$R^4$ ($R^4$ represents a hydroxy group, a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group}).

7. The carbazole derivative, hydrate thereof, or pharmaceutically acceptable salt thereof according to claim 1, wherein in the formula (I):
the ring A represents a phenyl group, a 2-furyl group, a 2-thienyl group, or a 4-pyridyl group;
X and Y represent any one of: (i) X representing —O— and Y representing (ii) X representing =N— and Y representing —O— or —S—, and (iii) X representing —S— and Y representing =N—;
both a and b represent a methylene group;
both V and Z represent —O—;
W represents a $C_1$-$C_{10}$ alkylene group whose 1 or 2 hydrogens may be substituted by a phenyl group or a $C_1$-$C_6$ alkyl group; a 1,2-phenylene group; or a 1,3-cyclohexyl group;
$R^1$ represents a methyl group;
$R^2$ represents a methoxy group; and
$R^3$ represents a carboxy group.

8. The carbazole derivative, hydrate thereof, or pharmaceutically acceptable salt thereof according to claim 1, wherein in the formula (I):
the ring A represents a phenyl group;
X represents —O—;
Y represents =N—;
both a and b represent a methylene group;
both V and Z represent —O—;
W represents a $C_1$-$C_4$ alkylene group whose 1 or 2 hydrogens may be substituted by a $C_1$-$C_4$ alkyl group;
$R^1$ represents a methyl group;
$R^2$ represents a methoxy group; and
$R^3$ represents a carboxy group.

9. The carbazole derivative, hydrate thereof, or pharmaceutically acceptable salt thereof according to claim 1, wherein in the formula (I):
the ring A represents a phenyl group;
X represents —O—;
Y represents
both a and b represent a methylene group;
both V and Z represent —O—;
W represents a methylene group, a methylmethylene group, a dimethylmethylene group, an ethylmethylene group, an isopropylmethylene group, an ethylene group, a methylethylene group, or an isopropylethylene group;
$R^1$ represents a methyl group;
$R^2$ represents a methoxy group; and
$R^3$ represents a carboxy group.

10. The carbazole derivative, hydrate thereof, or pharmaceutically acceptable salt thereof according to claim 1, wherein in the formula (I):
the ring A represents a phenyl group;
X represents =N—;
Y represents —O—;
a and b may be same or different, and represent a methylene group or an ethylene group;
both V and Z represent —O—;
W represents a $C_1$-$C_4$ alkylene group whose 1 or 2 hydrogens may be substituted by a $C_1$-$C_4$ alkyl group;
$R^1$ represents a methyl group;
$R^2$ represents a methoxy group; and
$R^3$ represents a carboxy group.

11. The carbazole derivative, hydrate thereof, or pharmaceutically acceptable salt thereof according to claim 1, wherein the carbazole derivative represented by the formula (I) is one of:
{9-[3-methoxy-4-((5-methyl-2-phenyl-oxazole-4-yl)methoxy)-benzyl]-9H-carbazole-4-yloxy}acetic acid,
{9-[4-((2-(furan-2-yl)-5-methyl-oxazole-4-yl)methoxy)-3-methoxy-benzyl]-9H-carbazole-4-yloxy}acetic acid,
2-{9-[3-methoxy-4-((5-methyl-2-phenyl-oxazole-4-yl)methoxy)-benzyl]-9H-carbazole-4-yloxy}-2-methyl-propionic acid,
(±)-2-{9-[3-methoxy-4-((5-methyl-2-phenyl-oxazole-4-yl)methoxy)-benzyl]-9H-carbazole-4-yloxy}propionic acid,
(±)-2-{9-[3-methoxy-4-((5-methyl-2-phenyl-oxazole-4-yl)methoxy)-benzyl]-9H-carbazole-4-yloxy}butyric acid,
(±)-2-{9-[4-((2-(furan-2-yl)-5-methyl-oxazole-4-yl)methoxy)-3-methoxy-benzyl]-9H-carbazole-4-yloxy}-2-phenylacetic acid,
2-{9-[4-((2-furan-2-yl-5-methyl-oxazole-4-yl)methoxy)-3-methoxy-benzyl]-9H-carbazole-4-yloxy}-2-methyl-propionic acid,
2-{9-[3-methoxy-4-((5-methyl-2-thiophene-2-yl-oxazole-4-yl)methoxy)-benzyl]-9H-carbazole-4-yloxy}-2-methyl-propionic acid,
2-{9-[3-methoxy-4-((5-methyl-2-pyridine-4-yl-oxazole-4-yl)methoxy)-benzyl]-9H-carbazole-4-yloxy}-2-methyl-propionic acid,
(±)-2-{9-[3-methoxy-4-((5-methyl-2-phenyl-oxazole-4-yl)methoxy)-benzyl]-9H-carbazole-4-yloxy}-3-methyl-butyric acid,
(±)-2-{9-[3-methoxy-4-((5-methyl-2-phenyl-oxazole-4-yl)methoxy)-benzyl]-9H-carbazole-4-yloxy}valeric acid, 4-{9-[3-methoxy-4-((5-methyl-2-phenyl-oxazole-4-yl)methoxy)-benzyl]-9H-carbazole-4-yloxy}butyric acid, 2-methyl-2-{9-[4-((5-methyl-2-phenyl-oxazole-4-yl)methoxy)-benzyl]-9H-carbazole-4-yloxy}propionic acid, 2-{9-[3-(2-(furan-2-yl)-5-methyl-oxazole-4-ylmethoxy)-4-methoxy-benzyl]-9H-carbazole-4-yloxy}-2-methyl-propionic acid, 2-{9-[3-methoxy-4-((5-methyl-2-phenyl-thiazole-4-yl)methoxy)-benzyl]-9H-carbazole-4-yloxy}-2-methyl-propionic acid, 2-{9-[3-methoxy-4-((4-methyl-2-phenyl-thiazole-5-yl)methoxy)-benzyl]-9H-carbazole-4-yloxy}-2-methyl-propionic acid, (±)-2-{9-[3-methoxy-4-((5-methyl-2-phenyl-oxazole-4-yl)methoxy)-benzyl]-9H-carbazole-4-yloxy}caproic acid, (±)-2-{9-[3-methoxy-4-((5-methyl-2-phenyl-oxazole-4-yl)methoxy)-benzyl]-9H-carbazole-4-yloxy}heptane acid, (±)-2-{9-[3-methoxy-4-((5-methyl-2-phenyl-oxazole-4-yl)methoxy)-benzyl]-9H-carbazole-4-yloxy}caprylic acid, 5-{9-[3-methoxy-4-((5-methyl-2-phenyl-oxazole-4-yl)methoxy)-benzyl]-9H-carbazole-4-yloxy}valeric acid, 6-{9-[3-methoxy-4-((5-methyl-2-phenyl-oxazole-4-yl)methoxy)-benzyl]-9H-carbazole-4-yloxy}caproic acid, 3-{9-[3-methoxy-4-((5-methyl-2-phenyl-oxazole-4-yl)methoxy)-benzyl]-9H-carbazole-4-yloxy}-2,2-dimethyl-propionic acid, 3-{9-[4-((2-(furan-2-yl)-5-methyl-oxazole-4-yl)methoxy)-3-methoxy-benzyl]-9H-carbazole-4-yloxy}-2,2-dimethyl-propionic acid, 3-{9-[3-methoxy-4-((5-methyl-2-(thiophene-2-yl)-oxazole-4-yl)methoxy)-benzyl]-9H-carbazole-4-yloxy}-2,2-dimethyl-propionic acid, 3-{9-[3-methoxy-4-((5-methyl-2-pyridine-4-yl-oxazole-4-yl)methoxy)-benzyl]-9H-carbazole-4-yloxy}-2,2-dimethyl-propionic acid, (±)-{9-[3-methoxy-4-((5-methyl-2-phenyl-oxazole-4-yl)methoxy)-benzyl]-9H-carbazole-4-yloxy}phenylacetic acid, (±)-4-{9-[3-methoxy-4-((5-methyl-2-phenyl-oxazole-4-yl)methoxy)-benzyl]-9H-carbazole-4-yloxy}-2-methyl-butyric acid, (S)-(+)-2-{9-[3-methoxy-4-((5-methyl-2-phenyl-oxazole-4-yl)methoxy)-benzyl]-9H-carbazole-4-yloxy}butyric acid, (S)-2-{9-[3-methoxy-4-((5-methyl-2-phenyl-oxazole-4-yl)methoxy)-benzyl]-9H-carbazole-4-yloxy}propionic acid, (S)-2-{9-[3-methoxy-4-((5-methyl-2-phenyl-oxazole-4-yl)methoxy)-benzyl]-9H-carbazole-4-yloxy}-3-methyl-butyric acid, (S)-2-{9-[3-methoxy-4-((5-methyl-2-phenyl-oxazole-4-yl)methoxy)-benzyl]-9H-carbazole-4-yloxy}valeric acid, (R)-2-{9-[3-methoxy-4-((5-methyl-2-phenyl-oxazole-4-yl)methoxy)-benzyl]-9H-carbazole-4-yloxy}butyric acid, (R)-2-{9-[3-methoxy-4-((5-methyl-2-phenyl-oxazole-4-yl)methoxy)-benzyl]-9H-carbazole-4-yloxy}propionic acid, (R)-2-{9-[3-methoxy-4-((5-methyl-2-phenyl-oxazole-4-yl)methoxy)-benzyl]-9H-carbazole-4-yloxy}-3-methyl-butyric acid, (R)-2-{9-[3-methoxy-4-((5-methyl-2-phenyl-oxazole-4-yl)methoxy)-benzyl]-9H-carbazole-4-yloxy}valeric acid, 4-((9-(4-((5-methyl-2-phenyloxazole-4-yl)methoxy)-3-methoxybenzyl)-9H-carbazole-5-yloxy)methyl)benzoic acid, 2-{9-[3-methoxy-4-((5-methyl-2-phenyl-oxazole-4-yl)methoxy)-benzyl]-9H-carbazole-4-yloxy}benzoic acid, 3-{9-[3-methoxy-4-((5-methyl-2-phenyloxazole-4-yl)methoxy)-benzyl]-9H-carbazole-4-yloxy}benzoic acid, 4-{9-[3-methoxy-4-((5-methyl-2-phenyl-oxazole-4-yl)methoxy)-benzyl]-9H-carbazole-4-yloxy}benzoic acid, (+)-2-{9-[3-methoxy-4-((5-methyl-2-phenyl-oxazole-4-yl)methoxy)-benzyl]-9H-carbazole-4-yloxy}-2-phenylacetic acid, (−)-2-{9-[3-methoxy-4-((5-methyl-2-phenyl-oxazole-4-yl)methoxy)-benzyl]-9H-carbazole-4-yloxy}-2-phenylacetic acid, (−)-4-{9-[3-methoxy-4-((5-methyl-2-phenyl-oxazole-4-yl)methoxy)-benzyl]-9H-carbazole-4-yloxy}-2-methyl-butyric acid, and (+)-4-{9-[3-methoxy-4-(5-methyl-2-phenyl-oxazole-4-ylmethoxy)-benzyl]-9H-carbazole-4-yloxy}-2-methyl-butyric acid.

12. A medical composition including:
the carbazole derivative, hydrate thereof, or pharmaceutically acceptable salt thereof according to claim 1; and
a pharmaceutically acceptable carrier.

13. A therapeutic agent for peroxisome proliferator-activated receptor-γ (PPARγ)-associated metabolic syndrome including the carbazole derivative, hydrate thereof, or pharmaceutically acceptable salt thereof according to claim 1 as an active ingredient.

14. A therapeutic agent for fatty liver, obesity, lipid metabolism abnormality, visceral adiposity, diabetes, hyperlipemia, impaired glucose tolerance, hypertension, non-alcoholic fatty liver disease, or non-alcoholic steatohepatitis, the agent including the carbazole derivative, hydrate thereof, or pharmaceutically acceptable salt thereof according to claim 1 as an active ingredient.

15. A therapeutic agent for fatty liver or obesity including the carbazole derivative, hydrate thereof, or pharmaceutically acceptable salt thereof according to claim 1 as an active ingredient.

16. A PPAR modulator including the carbazole derivative, hydrate thereof, or pharmaceutically acceptable salt thereof according to claim 1 as an active ingredient.

17. A PPARγ antagonist including the carbazole derivative, hydrate thereof, or pharmaceutically acceptable salt thereof according to claim 1 as an active ingredient.

18. A method for treating fatty liver, obesity, lipid metabolism abnormality, visceral adiposity, diabetes, hyperlipemia, impaired glucose tolerance, hypertension, non-alcoholic fatty liver disease, or non-alcoholic steatohepatitis, the method comprising administering to a subject a therapeutically effective amount of the carbazole derivative, hydrate thereof, or pharmaceutically acceptable salt thereof according to claim 1.

19. A carbazole derivative, hydrate thereof, or pharmaceutically acceptable salt thereof, the carbazole derivative represented by the following general formula (I"):

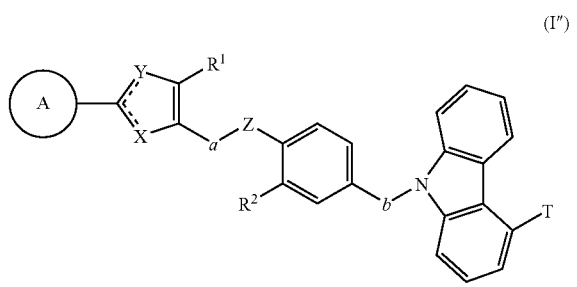
(I″)

wherein a ring A represents a $C_6$-$C_{10}$ aryl group which may have 1 to 3 substituent groups selected from the group A of substituent groups, or a 5- to 7-membered aromatic heterocyclic group which may have 1 to 3 substituent groups selected from the group A of substituent groups;
X represents =N—, =CH—, —O—, or —S—;
Y represents =N—, —O—, or —S—;
a and b may be same or different, and represent a $C_1$-$C_4$ alkylene group which may have a substituent group selected from the group A of substituent groups, a $C_2$-$C_4$ alkenylene group which may have a substituent group selected from the group A of substituent groups, or a $C_2$-$C_4$ alkynylene group which may have a substituent group selected from the group A of substituent groups;
Z represents a methylene group, =N—, —NH—, —O—, —S—, —S(=O)—, —S(=O)$_2$—, —C(=O)—, —C(=O)NH—, or —NHC(=O)—;
$R^1$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, or a $C_1$-$C_4$ alkoxy group which may have a substituent group selected from the group A of substituent groups;
$R^2$ represents a hydrogen atom, a $C_1$-$C_4$ alkyl group which may have a substituent group selected from the group A of substituent groups, a $C_2$-$C_4$ alkenyl group which may have a substituent group selected from the group A of substituent groups, a $C_2$-$C_4$ alkynyl group which may have a substituent group selected from the group A of substituent groups, a $C_1$-$C_4$ alkoxy group which may have a substituent group selected from the group A of substituent groups, or a $C_1$-$C_4$ alkylthio group which may have a substituent group selected from the group A of substituent groups;
T represents —OH, —OP, or —V—W—P';
P represents a $C_1$-$C_4$ alkyl group which may have a substituent group selected from the group A of substituent groups, a $C_1$-$C_4$ aliphatic acyl group which may have a substituent group selected from the group A of substituent groups, or a $C_7$-$C_{11}$ aromatic acyl group which may have a substituent group selected from the group A of substituent groups;
V represents a methylene group, =N—, —NH—, —O—, —S—, —S(=O)—, —S(=O)$_2$—, —C(=O)—, —C(=O)NH—, or —NHC(=O)—;
W represents a $C_1$-$C_{10}$ alkylene group which may have a substituent group selected from the group A of substituent groups, a $C_2$-$C_{10}$ alkenylene group which may have a substituent group selected from the group A of substituent groups, a $C_2$-$C_{10}$ alkynylene group which may have a substituent group selected from the group A of substituent groups, $C_3$-$C_7$ cycloaliphatic hydrocarbon group which may have 1 to 3 substituent groups selected from the group A of substituent groups, a $C_6$-$C_{10}$ arylene group which may have 1 to 3 substituent groups selected from the group A of substituent groups;
P' represents a $C_1$-$C_4$ alkyl group which may have a substituent group selected from the group A of substituent groups, a $C_1$-$C_4$ aliphatic acyl group which may have a substituent group selected from the group A of substituent groups, or a $C_7$-$C_{11}$ aromatic acyl group which may have a substituent group selected from the group A of substituent groups;
the group A of substituent groups represents a group including:
halogen;
a hydroxy group;
a carboxy group;
a cyano group;
a $C_1$-$C_6$ alkyl group whose 1 to 3 hydrogen atoms may be substituted by halogen, a hydroxy group, a carboxy group, or a carbamoyl group;
a $C_2$-$C_6$ alkenyl group whose 1 to 3 hydrogen atoms may be substituted by halogen, a hydroxy group, a carboxy group, or a carbamoyl group;
a $C_2$-$C_6$ alkynyl group whose 1 to 3 hydrogen atoms may be substituted by halogen, a hydroxy group, a carboxy group, or a carbamoyl group;
a $C_1$-$C_6$ alkoxy group whose 1 to 3 hydrogen atoms may be substituted by halogen, a hydroxy group, a carboxy group, or a carbamoyl group;
a $C_1$-$C_6$ alkylthio group whose 1 to 3 hydrogen atoms may be substituted by halogen, a hydroxy group, a carboxy group, or a carbamoyl group;
a $C_3$-$C_7$ cycloaliphatic hydrocarbon group whose 1 to 3 hydrogen atoms may be substituted by halogen, a hydroxy group, a carboxy group, or a carbamoyl group;
a $C_7$-$C_{16}$ aralkyl group whose 1 to 3 hydrogen atoms may be substituted by halogen, a hydroxy group, a carboxy group, or a carbamoyl group;
a carbamoyl group which may be monosubstituted or disubstituted by a substituent group selected from a $C_1$-$C_4$ alkoxycarbonyl group, a $C_1$-$C_4$ alkyl group, a $C_1$-$C_4$ alkylsulfonyl group, or a $C_6$-$C_{10}$ arylsulfonyl group;
a $C_6$-$C_{10}$ aryl group whose 1 to 3 hydrogen atoms may be substituted by halogen, a hydroxy group, a carboxy group, or a carbamoyl group; and
a 5- to 7-membered aromatic heterocyclic group whose 1 to 3 hydrogen atoms may be substituted by halogen, a hydroxy group, a carboxy group, or a carbamoyl group.

20. The carbazole derivative, hydrate thereof, or pharmaceutically acceptable salt thereof according to claim 19, wherein in the formula (I″):
the ring A represents {phenyl group, indenyl group, 1-naphthyl group, or 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or a azepinyl group} which may have 1 to 3 substituent groups selected from the group A of substituent groups;
X represents =N—, —O—, or —S—;
Y represents =N—, —O—, or —S—;

a and b may be same or different, and represent a $C_1$-$C_4$ alkylene group whose 1 or 2 hydrogens may be substituted by {halogen, a $C_1$-$C_4$ alkyl group, or a $C_1$-$C_4$ alkoxy group};

Z represents a methylene group, —NH—, —O—, —S—, or —S(=O)—;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by a substituent group selected from the group C of substituent groups, a $C_1$-$C_4$ alkoxy group whose 1 to 3 hydrogens may be substituted by a substituent group selected from the group C of substituent groups, or a $C_1$-$C_4$ alkylthio group whose 1 to 3 hydrogens may be substituted by a substituent group selected from the group C of substituent groups, where the group C of substituent groups represents a group including halogen, a $C_1$-$C_4$ alkyl group, a $C_1$-$C_4$ alkoxy group, and a $C_1$-$C_4$ haloalkyl group;

T represents —OH, —OP, or —V—W—P'

P represents a $C_1$-$C_4$ alkyl group, a $C_1$-$C_4$ aliphatic acyl group, or a $C_7$-$C_{11}$ aromatic acyl group;

V represents a methylene group, —NH—, —O—, —S—, or —S(=O)—;

W represents a $C_1$-$C_{10}$ alkylene group which may have a substituent group selected from the group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group;

P' represents a $C_1$-$C_4$ alkyl group, a $C_1$-$C_4$ aliphatic acyl group, or a $C_7$-$C_{11}$ aromatic acyl group.

21. The carbazole derivative, hydrate thereof, or pharmaceutically acceptable salt thereof according to claim 19, wherein in the formula (I"):

the ring A represents {a phenyl group, an indenyl group, a 1-naphthyl group, or a 2-naphthyl group} which may have 1 to 3 substituent groups selected from the group A of substituent groups, or {a furyl group, a thienyl group, a pyrrolyl group, a pyrazoryl group, an imidazolyl group, an oxazolyl group, an isooxazoyl group, a thiazolyl group, an isothiazolyl group, a 1,2,3-oxadiazolyl group, a triazolyl group, a thiadiazolyl group, a pyranyl group, a pyridyl group, a pyridazinyl group, a pyrimidinyl group, a pyrazinyl group, or an azepinyl group} which may have 1 to 3 substituent groups selected from the group A of substituent groups;

X represents =N—, —O—, or —S—;

Y represents =N—, —O—, or —S—;

a and b may be same or different, and represent a $C_1$-$C_4$ alkylene group whose 1 or 2 hydrogens may be substituted by {halogen, a $C_1$-$C_4$ alkyl group, or a $C_1$-$C_4$ alkoxy group};

Z represents a methylene group, —NH—, —O—, —S—, or —S(=O)—;

$R^1$ represents a $C_1$-$C_4$ alkyl group whose 1 to 3 hydrogens may be substituted by {halogen, a $C_1$-$C_4$ alkyl group, a $C_1$-$C_4$ alkoxy group, or a $C_1$-$C_4$ haloalkyl group}, or a $C_1$-$C_4$ alkoxy group whose 1 to 3 hydrogens may be substituted by {halogen, a $C_1$-$C_4$ alkyl group, a $C_1$-$C_4$ alkoxy group, or a $C_1$-$C_4$ haloalkyl group};

$R^2$ represents a hydrogen atom, a $C_1$-$C_4$ alkyl group whose 1 to 3 hydrogens may be substituted by {a $C_1$-$C_4$ alkyl group, a $C_1$-$C_4$ alkoxy group, or a $C_1$-$C_4$ haloalkyl group}, a $C_1$-$C_4$ alkoxy group whose 1 to 3 hydrogens may be substituted by {a $C_1$-$C_4$ alkyl group, a $C_1$-$C_4$ alkoxy group, or a $C_1$-$C_4$ haloalkyl group}, or a $C_1$-$C_4$ alkylthio group whose 1 to 3 hydrogens may be substituted by {a $C_1$-$C_4$ alkyl group, a $C_1$-$C_4$ alkoxy group, or a $C_1$-$C_4$ haloalkyl group};

T represents —OH, —OP, or —V—W—P';

P represents a $C_1$-$C_4$ alkyl group, a $C_1$-$C_4$ aliphatic acyl group, or a $C_7$-$C_{11}$ aromatic acyl group;

V represents a methylene group, —NH—, —O—, —S—, or —S(=O)—;

W represents a $C_1$-$C_{10}$ alkylene group which may have a substituent group selected from the group B of substituent groups, a $C_2$-$C_6$ alkenylene group which may have a substituent group selected from the group B of substituent groups, a $C_2$-$C_6$ alkynylene group which may have a substituent group selected from the group B of substituent groups, a $C_3$-$C_7$ cycloalkylene group which may have 1 to 3 substituent groups selected from the group B of substituent groups, a $C_3$-$C_7$ cycloalkenylene group which may have 1 to 3 substituent groups selected from the group B of substituent groups, a $C_5$-$C_{10}$ arylene group which may have 1 to 3 substituent groups selected from the group B of substituent groups, where the group B of substituent groups represents a group including halogen, a $C_1$-$C_6$ alkyl group, a $C_1$-$C_6$ alkoxy group, a $C_1$-$C_6$ alkylthio group, a $C_1$-$C_6$ halogenoalkyl group, and a $C_6$-$C_{10}$ aryl group; and P' represents a $C_1$-$C_4$ alkyl group, a $C_1$-$C_4$ aliphatic acyl group, or a $C_7$-$C_{11}$ aromatic acyl group.

22. The carbazole derivative, hydrate thereof, or pharmaceutically acceptable salt thereof according to claim 19, wherein in the formula (I"):

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, an thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X represents =N—, —O—, or —S—;

Y represents =N—, —O—, or —S—;

a and b may be same or different, and represent a $C_1$-$C_4$ alkylene group;

Z represents a methylene group, —NH—, —O—, —S—, or —S(=O)—;

R¹ represents a $C_1$-$C_4$ alkyl group, or a $C_1$-$C_4$ alkoxy group;

R² represents a hydrogen atom, a $C_1$-$C_4$ alkoxy group, or a $C_1$-$C_4$ alkylthio group;

T represents —OH, —OP, or —V—W—P';

P represents an allyl group, a benzyl group, a methoxymethyl group, or a t-butyl group;

V represents a methylene group, —NH—, —O—, —S—, or —S(=O)—;

W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, or {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group}; and P' represents a $C_1$-$C_4$ alkyl group, an allyl group, a benzyl group, or a methoxymethyl group.

23. The carbazole derivative, hydrate thereof, or pharmaceutically acceptable salt thereof according to claim 19, wherein in the formula (I"):

the ring A represents {a phenyl group, a 1-naphthyl group, or a 2-naphthyl group} whose 1 or 2 hydrogens may be substituted by {halogen, a $C_1$-$C_4$ alkyl group, or a $C_1$-$C_4$ alkoxy group}, or represents {a furyl group, a thienyl group, a pyrrolyl group, an imidazolyl group, an oxazolyl group, an isooxazoyl group, a thiazolyl group, an isothiazolyl group, a pyranyl group, or a pyridyl group} whose 1 or 2 hydrogens may be substituted by {halogen, a $C_1$-$C_4$ alkyl group, or a $C_1$-$C_4$ alkoxy group};

X and Y represent any one of: (i) X representing —O— and Y representing =N—, (ii) X representing =N— and Y representing —O— or —S—, and (iii) X representing —S— and Y representing =N—;

a and b may be same or different, and represent a $C_1$-$C_4$ alkylene group;

Z represents —NH—, —O—, —S—, or —S(=O)—;

R¹ represents a $C_1$-$C_4$ alkyl group, or a $C_1$-$C_4$ alkoxy group;

R² represents a hydrogen atom, a $C_1$-$C_4$ alkoxy group, or a $C_1$-$C_4$ alkylthio group;

T represents —OH, —OP, or —V—W—P';

P represents an allyl group, a benzyl group, a methoxymethyl group, or a t-butyl group;

V represents —NH—, —O—, —S—, or —S(=O)—;

W represents {a $C_1$-$C_{10}$ alkylene group, a $C_2$-$C_6$ alkenylene group, or a $C_2$-$C_6$ alkynylene group} whose 1 or 2 hydrogens may be substituted by {halogen, a $C_1$-$C_6$ alkyl group, or a phenyl group}, or {a $C_3$-$C_7$ cycloalkylene group, a $C_3$-$C_7$ cycloalkenylene group, or a $C_6$-$C_{10}$ arylene group} whose 1 to 3 hydrogens may be substituted by {halogen, a $C_1$-$C_6$ alkyl group, or a phenyl group}; and P' represents a $C_1$-$C_4$ alkyl group, an allyl group, a benzyl group, or a methoxymethyl group.

* * * * *

```
SEQUENCE LISTING

<160> NUMBER OF SEQ ID NOS: 8

<210> SEQ ID NO 1
<211> LENGTH: 30
<212> TYPE: DNA
<213> ORGANISM: Artificial
<220> FEATURE:
<223> OTHER INFORMATION: Primer

<400> SEQUENCE: 1
ttctcgaggc aaacccctat tccatgctgt                                        30

<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
gaaatgttgg cagtggctca g                                                 21

<210> SEQ ID NO 3
<211> LENGTH: 29
<212> TYPE: DNA
<213> ORGANISM: Artificial
<220> FEATURE:
<223> OTHER INFORMATION: Primer

<400> SEQUENCE: 3
ttgctagccg tgcttcctgc ttcatagat                                         29

<210> SEQ ID NO 4
<211> LENGTH: 31
<212> TYPE: DNA
<213> ORGANISM: Artificial
```

```
<220> FEATURE:
<223> OTHER INFORMATION: Primer

<400> SEQUENCE: 4
ttgtcgactc ctggaaaagg tgtggctgat g                              31

<210> SEQ ID NO 5
<211> LENGTH: 28
<212> TYPE: DNA
<213> ORGANISM: Artificial
<220> FEATURE:
<223> OTHER INFORMATION: Primer

<400> SEQUENCE: 5
acgaattcag ttagtcgcag acatggac                                  28

<210> SEQ ID NO 6
<211> LENGTH: 28
<212> TYPE: DNA
<213> ORGANISM: Artificial
<220> FEATURE:
<223> OTHER INFORMATION: Primer

<400> SEQUENCE: 6
gttctagagc aggcctaagt catttggt                                  28

<210> SEQ ID NO 7
<211> LENGTH: 36
<212> TYPE: DNA
<213> ORGANISM: Artificial
<220> FEATURE:
<223> OTHER INFORMATION: Primer

<400> SEQUENCE: 7
tcgacagggg accaggacaa aggtcacgtt cgggag                         36

<210> SEQ ID NO 8
<211> LENGTH: 36
<212> TYPE: DNA
<213> ORGANISM: Artificial
<220> FEATURE:
<223> OTHER INFORMATION: Primer

<400> SEQUENCE: 8
tcgactcccg aacgtgacct ttgtcctggt cccctg                         36
```